United States Patent
Shibata et al.

(10) Patent No.: US 6,987,112 B2
(45) Date of Patent: Jan. 17, 2006

(54) ORGANIC COMPOUND HAVING CYANO GROUP AND INSECTICIDES/MITICIDES

(75) Inventors: Yasushi Shibata, Kanagawa (JP); Renpei Hatano, Kanagawa (JP); Takao Iwasa, Kanagawa (JP); Satoru Makita, Kanagawa (JP); Daisuke Hanai, Kanagawa (JP); Masao Yamaguchi, Kanagawa (JP); Naomi Ichikawa, Kanagawa (JP)

(73) Assignee: Nippon Soda Co., Ltd., Palm Harbor, FL (US)

( * ) Notice: Subject to any disclaimer, the term of this patent is extended or adjusted under 35 U.S.C. 154(b) by 0 days.

(21) Appl. No.: 10/415,797

(22) PCT Filed: Nov. 1, 2001

(86) PCT No.: PCT/JP01/09581

§ 371 (c)(1),
(2), (4) Date: Oct. 8, 2003

(87) PCT Pub. No.: WO02/36550

PCT Pub. Date: May 10, 2002

(65) Prior Publication Data

US 2004/0072826 A1 Apr. 15, 2004

(30) Foreign Application Priority Data

Nov. 2, 2000 (JP) ........................ 2000-335827

(51) Int. Cl.
*A61K 31/54* (2006.01)
*A61K 31/496* (2006.01)
*A61K 31/4172* (2006.01)
*A61K 31/277* (2006.01)
*C07C 327/00* (2006.01)

(52) U.S. Cl. .................. 514/256; 514/277.5; 514/365; 514/374; 514/378; 514/381; 514/400; 514/252.1; 548/129; 548/205; 548/214; 548/236; 548/267.2; 548/268.2; 548/375.1; 546/257; 546/258; 549/77; 549/491

(58) Field of Classification Search ................ 544/238, 544/335; 548/129, 205, 214, 236, 267.2, 548/268.2, 335.2, 252, 375.1, 376; 546/257, 546/258; 549/77, 491; 514/256, 252.12, 277, 514/365, 374, 378, 381, 274, 385, 400; 558/257, 558/258
See application file for complete search history.

(56) References Cited

FOREIGN PATENT DOCUMENTS

| | | |
|---|---|---|
| EP | 189960 A2 | 8/1986 |
| EP | 0913392 A1 | 5/1999 |
| JP | 60011401 | 1/1985 |
| JP | 8295663 A2 | 11/1996 |
| WO | WO 9740009 A1 | 10/1997 |
| WO | WO 9835935 A1 | 8/1998 |
| WO | WO 9842683 A1 | 10/1998 |
| WO | WO 9937603 A1 | 7/1999 |
| WO | WO 9944993 A1 | 9/1999 |

OTHER PUBLICATIONS

K. Takahashi et al., "Syntheses of 3(5)-Substituted-4-(N-methylanilino)-5(3)-aminopyrazoles by Reaction of B-Hydroxy-x-cyano-enamines with Hydrazines", 1985, No. 8, pp. 794–796.

D. Knittel, "Reactions of a-Ketoazides with N,N-Dimethylamino-nitrosobenzol", Anrog. Chem., Org. Chem., 1983, No. 6).

K. Takahashi et al., "An Efficient Synthesis of a-Keto Amides via Reaction of a-(N-Methylanilino)-Acetonitrile with Esters Followed by Hydrolysis Using Copper (II) Acetate", Chem. Letters, 1983, No. 6, pp. 859–862.

*Primary Examiner*—Johann Richter
*Assistant Examiner*—Ebenezer Sackey
(74) *Attorney, Agent, or Firm*—Dennis G. LaPointe

(57) ABSTRACT

The present invention is directed to compounds represented by Formula (1);

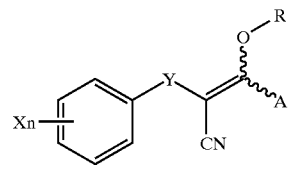

wherein A, R, X, Y and n are as defined in the description, the salts thereof, and insecticide/acaricide compositions characterized by comprising one or more of said compounds and/or said salts as the active ingredients.

2 Claims, No Drawings

ORGANIC COMPOUND HAVING CYANO GROUP AND INSECTICIDES/MITICIDES

FIELD OF INVENTION

The present invention relates to novel compounds and insecticidal/acaricidal compositions containing said compounds as active ingredients.

BACKGROUND ART

Until now, a large number of pest controlling agents, such as insecticides and acaricides, have been used. However, many of them are scarcely satisfactory as pest controlling agents for a number of reasons: insufficient efficacy, restrictions on their use due to pesticide resistance problems, phytotoxicity or pollution on plants, or strong toxicity on humans, domestic animals and fishes. Therefore, there has been a desire for the development of pest controlling agents that are applicable safely and have fewer of the above-mentioned drawbacks.

Acrylonitrile derivatives similar to the compounds of the present invention are disclosed in EP 189960, WO97/40009, WO98/42683, WO98/35935, WO99/44993, etc.

Further, WO98/35935 has disclosed compounds represented by the following chemical structure that is shown in the Table I-d thereof. However, there is no description in this reference on their insecticidal and/or acaricidal activities.

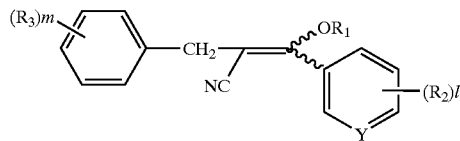

DISCLOSURE OF THE INVENTION

It is an object of the present invention to provide novel compounds which can be used as the active ingredients of insecticides and acaricides capable of being easily manufactured in an industrial scale, providing firm efficacy, and being applicable safely.

The present invention is directed to compounds represented by Formula (1) and insecticidal/acaricidal compositions characterized by comprising one or more of the compounds represented by said Formula (1) as the active ingredient(s).

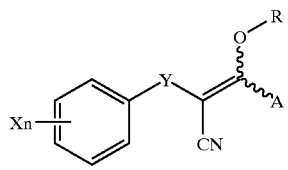

In the above Formula (1);

A is phenyl substituted by W or a heterocyclic group substituted by W;

wherein W is nitro, cyano, halogeno, $C_{1-6}$ alkyl, $C_{3-8}$ cycloalkyl, $C_{1-6}$ haloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, $C_{1-6}$ alkylamino, di-$C_{1-6}$ alkylamino, $C_{1-6}$ alkylcarbonyl, $C_{1-6}$ alkoxycarbonyl, phenyl optionally substituted by $G_1$, or phenoxy optionally substituted by $G_1$;

wherein $G_1$ is nitro, cyano, halogeno, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, $C_{1-6}$ alkylamino, di-$C_{1-6}$ alkylamino, $C_{1-6}$ alkylcarbonyl, or $C_{1-6}$ alkoxycarbonyl;

said heterocyclic group is a 5- or 6-membered heterocyclic group that contains at least one heteroatom selected from a group consisting of oxygen, sulfur and nitrogen;

when either of said phenyl or said heterocyclic group contains 2 or more substituents W, W may be the same or different from each other;

R is hydrogen, $C_{1-6}$ alkyl, $C_{1-6}$ alkoxy $C_{1-6}$ alkyl, $C_{1-6}$ alkylcarbonyloxy $C_{1-6}$ alkyl, $C_{3-6}$ cycloalkylcarbonyloxy $C_{1-6}$ alkyl, $C_{1-6}$ alkoxycarbonyloxy $C_{1-6}$ alkyl, optionally substituted phenylcarbonyloxy $C_{1-6}$ alkyl, $C_{1-6}$ alkylthio $C_{1-6}$ alkyl, $C_{1-6}$ alkylcarbonylthio $C_{1-6}$ alkyl, $C_{3-6}$ cycloalkylcarbonylthio $C_{1-6}$ alkyl, $C_{1-6}$ alkoxycarbonylthio $C_{1-6}$ alkyl, optionally substituted phenylcarbonylthio $C_{1-6}$ alkyl, optionally substituted phenyl $C_{1-6}$ alkyl, a group represented by a formula of $COR_1$, a group represented by a formula of $CSR_1$, or a group represented by a formula of $SO_2R_2$;

wherein $R_1$ is $C_{1-12}$ alkyl, $C_{3-6}$ cycloalkyl, $C_{1-6}$ haloalkyl, $C_{1-6}$ alkoxy, $C_{1-6}$ alkylthio, $C_{1-6}$ alkylamino, di-$C_{1-6}$ alkylamino, optionally substituted phenyl $C_{1-6}$ alkyl, optionally substituted phenyl $C_{1-6}$ alkoxy, or optionally substituted phenyl, and $R_2$ is $C_{1-12}$ alkyl or optionally substituted phenyl;

X is nitro, cyano, halogeno, $C_{1-6}$ alkyl, $C_{2-6}$ alkenyl, $C_{2-6}$ alkynyl, $C_{3-8}$ cycloalkyl, $C_{1-6}$ haloalkyl, $C_{2-6}$ haloalkenyl, $C_{1-6}$ alkoxy, $C_{1-6}$ haloalkoxy, $C_{2-6}$ alkenyloxy, $C_{2-6}$ haloalkenyloxy, $C_{2-6}$ alkynyloxy, $C_{1-6}$ alkylthio, $C_{1-6}$ alkylsulfinyl, $C_{1-6}$ alkylsulfonyl, $C_{1-6}$ alkylamino, di-$C_{1-6}$ alkylamino, tri-$C_{1-6}$ alkylsilyl, $C_{1-6}$ alkoxy $C_{1-6}$ alkyl, $C_{1-6}$ alkylthio $C_{1-6}$ alkyl, $C_{1-6}$ alkylsulfinyl $C_{1-6}$ alkyl, $C_{1-6}$ alkylsulfonyl $C_{1-6}$ alkyl, $C_{1-6}$ alkylcarbonyl, $C_{1-6}$ alkoxycarbonyl, phenyl $C_{1-6}$ alkyl optionally substituted by $G_2$, phenyl $C_{1-6}$ alkoxy optionally substituted by $G_2$, thienyl optionally substituted by $G_3$, pyridyl optionally substituted by $G_2$, pyridyloxy optionally substituted by $G_2$, phenyl optionally substituted by $G_4$, or phenoxy optionally substituted by $G_4$;

wherein $G_2$ is $C_{1-6}$ alkyl, halogeno, $C_{1-6}$ haloalkyl, or $C_{1-6}$ haloalkoxy, $G_3$ is $C_{1-6}$ alkyl or halogeno, and $G_4$ is nitro, cyano, halogeno, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, $C_{1-6}$ alkylamino, di-$C_{1-6}$ alkylamino, $C_{1-6}$ alkylcarbonyl, or $C_{1-6}$ alkoxycarbonyl;

n is 0, or an integer of 1 to 5, and when n is 2 or more, the above X may be same or different from each other; and Y is oxygen, sulfur, or nitrogen substituted by either hydrogen or $C_{1-6}$ alkyl.

MODE FOR CARRYING OUT THE INVENTION

In the above Formula (1),

A is phenyl substituted by W, or a heterocyclic group substituted by W;

W is nitro, cyano, halogeno, such as fluoro, chloro, bromo and iodo, $C_{1-6}$ alkyl, such as methyl, ethyl, n-propyl, isopropyl, n-butyl, sec-butyl, isobutyl, t-butyl, n-pentyl and isomers thereof, and n-hexyl and isomers thereof, $C_{3-6}$ cycloalkyl, such as cyclopropyl, cyclobutyl, cyclopentyl, and cyclohexyl, $C_{1-6}$ haloalkyl, such as chloromethyl, fluoromethyl, bromomethyl, dichloromethyl, difluoromethyl, dibromomethyl, trichloromethyl, trifluoromethyl, tribromomethyl, 2,2,2-trichloroethyl, 2,2,2-trifluoroethyl, and pentafluoroethyl, $C_{1-6}$ alkoxy, such as methoxy, ethoxy, n-propoxy, isopropoxy, n-butoxy, sec-butoxy, isobutoxy, and t-butoxy, $C_{1-6}$ haloalkoxy, such as chloromethoxy, dichloromethoxy, trichloromethoxy, trifluoromethoxy, 1-fluoroethoxy, and 1,1-difluoroethoxy, $C_{1-6}$ alkylthio, such as methylthio, ethylthio, n-propylthio, isopropylthio, n-butylthio, isobutylthio, sec-butylthio, and t-butylthio, $C_{1-6}$ alkylsulfinyl, such as methylsulfinyl, ethylsulfinyl, propylsulfinyl, and butylsulfinyl, $C_{1-6}$ alkylsulfonyl, such as methylsulfonyl, ethylsulfonyl, n-propylsulfonyl, and n-butylsulfonyl, $C_{1-6}$ alkylamino, such as methylamino, ethylamino, n-propylamino, isopropylamino, n-butylamino, isobutylamino, sec-butylamino, t-butylamino, 1-methylbutylamino, and n-pentylamino, di-$C_{1-6}$ alkylamino, such as dimethylamino, diethylamino, dipropylamino, dibutylamino, ethylisopropylamino, and methylpropylamino, $C_{1-6}$ alkylcarbonyl, such as methylcarbonyl, ethylcarbonyl, n-propylcarbonyl, and n-butylcarbonyl, $C_{1-6}$ alkoxycarbonyl, such as methoxycarbonyl, ethoxycarbonyl, n-propoxycarbonyl, isopropoxycarbonyl, n-butoxycarbonyl, and t-butoxycarbonyl, phenyl optionally substituted by $G_1$, or phenoxy optionally substituted by $G_1$;

wherein $G_1$ is nitro, cyano, halogeno, such as fluoro, chloro, bromo and iodo, $C_{1-6}$ alkyl, such as methyl, ethyl, n-propyl, isopropyl, n-butyl, sec-butyl, isobutyl, and t-butyl, $C_{1-6}$ haloalkyl, such as chloromethyl, fluoromethyl, bromomethyl, dichloromethyl, difluoromethyl, dibromomethyl, trichloromethyl, trifluoromethyl, tribromomethyl, trichloroethyl, trifluoroethyl, and pentafluoroethyl, $C_{1-6}$ alkoxy, such as methoxy, ethoxy, n-propoxy, isopropoxy, n-butoxy, sec-butoxy, isobutoxy, and t-butoxy, $C_{1-6}$ haloalkoxy, such as chloromethoxy, dichloromethoxy, trichloromethoxy, trifluoromethoxy, 1-fluoroethoxy, and 1,1-difluoroethoxy, $C_{1-6}$ alkylthio, such as methylthio, ethylthioethyl, n-propylthio, isopropylthio, n-butylthio, isobutylthio, sec-butylthio, and t-butylthio, $C_{1-6}$ alkylsulfinyl, such as methylsulfinyl, ethylsulfinyl, propylsulfinyl, and butylsulfinyl, $C_{1-6}$ alkylsulfonyl, such as methylsulfonyl, ethylsulfonyl, propylsulfonyl, and butylsulfonyl, $C_{1-6}$ alkylamino, such as methylamino, ethylamino, n-propylamino, isopropylamino, n-butylamino, isobutylamino, sec-butylamino, t-butylamino, 1-methylbutylamino, and n-pentylamino, di-$C_{1-6}$ alkylamino, such as dimethylamino, diethylamino, dipropylamino, dibutylamino, ethylisopropylamino, methylpropylamino, and methylbutylamino, $C_{1-6}$ alkylcarbonyl, such as methylcarbonyl, ethylcarbonyl, propylcarbonyl and butylcarbonyl, or $C_{1-6}$ alkoxycarbonyl, such as methoxycarbonyl, ethoxycarbonyl, n-propoxycarbonyl, isopropoxycarbonyl, n-butoxycarbonyl, and t-butoxycarbonyl.

In the above Formula (1), said heterocyclic group optionally substituted by W is a 5- or 6-membered heterocyclic group containing 1 to 4 atoms of nitrogen, oxygen or sulfur, which is, for example, triazolyl, thiazolyl, oxazolyl, isoxazolyl, isothiazolyl, pyrazolyl, imidazolyl, triazolyl, tetrazolyl, oxadiazolyl, thiadiazolyl, thienyl, furyl, pyrrolyl, pyridyl, pyridazinyl, pyrimidinyl, or the like. More specifically, the examples of said heterocyclic group optionally substituted by W include 2-furyl, 3-furyl, 2-thienyl, 3-thienyl, pyrrol-2-yl, pyrrol-3-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, pyrazol-3-yl, pyrazol-4-yl, imidazol-2-yl, imidazol-4-yl, imidazol-5-yl, 1,2,4-triazol-3-yl, 1,2,3-triazol-4-yl, tetrazolyl, 1,2,4-oxadiazol-3-yl, 1,2,4-oxadiazol-5-yl, 1,3,4-oxadiazol-2-yl, 1,3,4-oxadiazol-5-yl, 1,2,4-thiadiazol-3-yl, 1,2,4-thiadiazol-5-yl, 1,3,4-thiadiazol-2-yl, 1,3,4-thiadiazole-5-yl, 2-pyridyl, 3-pyridyl, 4-pyridyl, 5-pyridyl, 3-pyridazinyl, 4-pyridazinyl, 2-pyrimidinyl, 4-pyrimidinyl, 2-pyrazinyl, and the like.

Note that, when said phenyl or said heterocyclic group contains 2 or more substituents W, W may be the same or different from each other.

In the above Formula (1),

R is hydrogen, $C_{1-6}$ alkyl, such as methyl, ethyl, n-propyl, isopropyl, n-butyl, sec-butyl, isobutyl, t-butyl, pentyl and isomers thereof, and hexyl and isomers thereof, $C_{1-6}$ alkoxy $C_{1-6}$ alkyl, such as methoxymethyl, methoxyethyl, ethoxymethyl, propoxymethyl, and butoxymethyl, $C_{1-6}$ alkylcarbonyloxy $C_{1-6}$ alkyl, such as acetoxymethyl, pivaloyloxymethyl, heptanoyloxymethyl, acetoxyethyl, and acetoxyhexyl, $C_{3-6}$ cycloalkylcarbonyloxy $C_{1-6}$ alkyl, such as cyclopropylcarbonyloxymethyl, cyclopentylcarbonyloxymethyl, cyclohexylcarbonyloxymethyl, cyclopropylcarbonyloxyethyl, and cyclopropylcarbonyloxyhexane, $C_{1-6}$ alkoxycarbonyloxy $C_{1-6}$ alkyl, such as methoxycarbonyloxymethyl, 1-(methoxycarbonyloxy)ethyl, ethoxycarbonyloxymethyl, propoxycarbonyloxymethyl, isopropoxycarbonyloxymethyl, butoxycarbonyloxymethyl, and t-butoxycarbonyloxymethyl, phenylcarbonyloxy $C_{1-6}$ alkyl, such as optionally substituted benzoyloxymethyl and 1-(benzoyloxy)ethyl, $C_{1-6}$ alkylthio $C_{1-6}$ alkyl, such as methylthiomethyl, methylthioethyl, ethylthioethyl, ethylthiomethyl, propylthiomethyl, and butylthiomethyl, $C_{1-6}$ alkylcarbonylthio $C_{1-6}$ alkyl, such as methylcarbonylthiomethyl, methylcarbonylthioethyl, 1-(methylcarbonylthio)ethyl, ethylcarbonylthiomethyl, propylcarbonylthiomethyl, and butylcarbonylthiomethyl, $C_{3-6}$ cycloalkylcarbonylthio $C_{1-6}$ alkyl, such as cyclopropylcarbonylthiomethyl, cyclopropylcarbonylthioethyl, 1-(cyclopropylcarbonylthio) ethyl, cyclobutylcarbonylthiomethyl, cyclopentylcarbonylthiomethyl, and cyclohexylcarbonylthiomethyl, $C_{1-6}$ alkoxycarbonylthio $C_{1-6}$ alkyl, such as methoxycarbonylthiomethyl, 1-methoxycarbonylthioethyl, ethoxycarbonylthiomethyl, propoxycarbonylthiomethyl, isopropoxycarbonylthiomethyl, butoxycarbonylthiomethyl, and t-butoxycarbonylthiomethyl, phenylcarbonylthio $C_{1-6}$ alkyl, such as optionally substituted benzoylthiomethyl, and benzoylthioethyl, phenyl $C_{1-6}$ alkyl, such as optionally substituted benzyl and phenetyl, a group represented by a formula of $COR_1$, a group represented by a formula of $CSR_1$, or a group represented by a formula of $SO_2R_2$;

wherein $R_1$ is $C_{1-12}$ alkyl, such as methyl, ethyl, n-propyl, isopropyl, n-butyl, isobutyl, sec-butyl, t-butyl, n-pentyl and isomers thereof, n-hexyl and isomers thereof, n-heptyl and isomers thereof, n-nonyl and isomers thereof, and dodecyl, $C_{3-6}$ cycloalkyl, such as cyclopropyl, cyclobutyl, cyclopentyl, and cyclohexyl, $C_{1-6}$ haloalkyl, such as chloromethyl, fluoromethyl, bromomethyl, dichloromethyl, difluoromethyl, dibromomethyl, trichloromethyl, trifluoromethyl, tribromomethyl, trichloroethyl, trifluoroethyl, and pentafluoroethyl, $C_{1-6}$ alkoxy, such as methoxy, ethoxy, propoxy, isopropoxy, butoxy, sec-butoxy, isobutoxy, and t-butoxy, $C_{1-6}$ alkylthio, such as methylthio, ethylthio, n-propylthio, isopropylthio, n-butylthio, isobutylthio, sec-butylthio, and t-butylthio, $C_{1-6}$ alkylamino, such as methylamino, ethylamino, n-propylamino, isopropylamino, n-butylamino, isobutylamino, sec-butylamino, t-butylamino, 1-methylbutylamino, and n-pentylamino, di-$C_{1-6}$ alkylamino, such as dimethylamino, diethylamino, dipropylamino, dibutylamino, ethylisopropylamino, methylpropylamino, and methylbutylamino, optionally substituted phenyl $C_{1-6}$ alkyl, optionally substituted phenyl $C_{1-6}$ alkoxy, or optionally substituted phenyl; and $R_2$ is $C_{1-12}$ alkyl, such as methyl, ethyl, n-propyl, isopropyl, n-butyl, isobutyl, sec-butyl, t-butyl, n-pentyl and isomers thereof, n-hexyl and isomers thereof, n-heptyl and isomers thereof, n-nonyl and isomers thereof, and n-dodecyl, or optionally substituted phenyl, said substituent for substituting said phenyl respectively contained in said R, $R_1$ and $R_2$ is, for example, halogeno, such as fluoro, chloro, bromo and iodo, $C_{1-6}$ alkyl, such as methyl, ethyl, n-propyl, isopropyl, n-butyl, sec-butyl, isobutyl, and t-butyl, $C_{1-6}$ haloalkyl, such as chloromethyl, fluoromethyl, bromomethyl, dichloromethyl, difluoromethyl, dibromomethyl, trichloromethyl, trifluoromethyl, tribromomethyl, and trichloroethyl, or $C_{1-6}$ alkoxy, such as methoxy, ethoxy, n-propoxy, isopropoxy, n-butoxy, sec-butoxy, isobutoxy and t-butoxy;

said phenyl $C_{1-6}$ alkyl of said optionally substituted phenyl $C_{1-6}$ alkyl examped for said $R_1$ is, for example, benzyl, 1-phenylethyl, 2-phenylethyl, 1-phenyl-1-methylethyl, 1-phenylpropyl, 2-phenylpropyl, 3-phenylpropyl, and the like, and said phenyl $C_{1-6}$ alkoxy of said optionally substituted phenyl $C_{1-6}$ alkoxy examped for said $R_1$ is, for example, benzyloxy, 1-phenylethoxy, 2-phenylethoxy, 1-phenyl-1-methylethoxy, 1-phenylpropoxy, 2-phenylpropoxy, 3-phenylpropoxy and the like;

X is nitro, cyano, halogeno, such as fluoro, chloro, bromo, and iodo, $C_{1-6}$ alkyl, such as methyl, ethyl, n-propyl, isopropyl, n-butyl, sec-butyl, isobutyl, t-butyl, n-pentyl and isomers thereof, and n-hexyl and isomers thereof, $C_{2-6}$ alkenyl, such as ethenyl, 1-propenyl, 2-propenyl, 1-butenyl, 2-butenyl, 3-butenyl, 1-methyl-2-propenyl, 2-methyl-2-propenyl, 1-pentenyl, 2-pentenyl, 3-pentenyl, 4-pentenyl, 1-methyl-2-butenyl, 2-methyl-2-butenyl, 1-hexenyl, 2-hexenyl, 3-hexenyl, 4-hexenyl, and 5-hexenyl, $C_{2-6}$ alkynyl, such as ethynyl, 1-propynyl, 2-propynyl, 1-butynyl, 2-butynyl, 3-butynyl, 1-methyl-2-propynyl, 2-methyl-3-butynyl, 1-pentynyl, 2-pentynyl, 3-pentynyl, 4-pentynyl, 1-methyl-2-butynyl, 2-methyl-3-pentynyl, 1-hexynyl, and 1,1-dimethyl-2-butynyl, $C_{3-8}$ cycloalkyl, such as cyclopropyl, cyclobutyl, cyclopentyl and cyclohexyl, $C_{1-6}$ haloalkyl, such as chloromethyl, fluoromethyl, bromomethyl, dichloromethyl, difluoromethyl, dibromomethyl, trichloromethyl, trifluoromethyl, tribromomethyl, trichloroethyl, trifluoroethyl, and pentafluoroethyl, $C_{2-6}$ haloalkenyl, such as 3-chloro-2-propenyl, 4-chloro-2-butenyl, 4,4-dichloro-3-butenyl, 4,4-difluoro-3-butenyl, and 3,3,-dichloro-2-propenyl, $C_{1-6}$ alkoxy, such as methoxy, ethoxy, n-propoxy, isopropoxy, n-butoxy, sec-butoxy, isobutoxy, and t-butoxy, $C_{1-6}$ haloalkoxy, such as chloromethoxy, dichloromethoxy, trichloromethoxy, trifluoromethoxy, 1-fluoroethoxy, 1,1-difluoroethoxy, 2,2,2-trifluoroethoxy, and pentafluoroethoxy, $C_{2-6}$ alkenyloxy, such as allyloxy, 2-propenyloxy, 2-butenyloxy, and 2-methyl-3-propenyloxy, $C_{2-6}$ haloalkenyloxy, such as 3-chloro-2-propenyloxy, 3,3-dichloro-2-propenyloxy, 4-chloro-2-butenyloxy, 4,4-dichloro-3-butenyloxy, and 4,4-difluoro-3-butenyloxy, $C_{2-6}$ alkynyloxy, such as 2-propynyloxy, 2-butynyloxy, and 1-methyl-2-propynyloxy, $C_{1-6}$ alkylthio, such as methylthio, ethylthio, n-propylthio, isopropylthio, n-butylthio, isobutylthio, sec-butylthio, and t-butylthio, $C_{1-6}$ alkylsulfinyl, such as methylsulfinyl, ethylsulfinyl, propylsulfinyl, and butylsulfinyl, $C_{1-6}$ alkylsulfonyl, such as methylsulfonyl, ethylsulfonyl, propylsulfonyl, and butylsulfonyl, $C_{1-6}$ alkylamino, such as methylamino, ethylamino, n-propylamino, isopropylamino, n-butylamino, isobutylamino, sec-butylamino, t-butylamino, 1-methylbutylamino, and n-pentylamino, di-$C_{1-6}$ alkylamino, such as dimethylamino, diethylamino, dipropylamino, dibutylamino, ethylisopropylamino, and methylpropylamino, $C_{1-6}$ alkylsilyl such as trimethylsilyl, $C_{1-6}$ alkoxy $C_{1-6}$ alkyl, such as methoxymethyl, methoxyethyl, ethoxymethyl, propoxymethyl, and butoxymethyl, $C_{1-6}$ alkylthio $C_{1-6}$ alkyl, such as methylthiomethyl, methylthioethyl, ethylthioethyl, ethylthiomethyl, propylthiomethyl, and butylthiomethyl, $C_{1-6}$ alkylsulfinyl $C_{1-6}$ alkyl, such as methylsulfinylmethyl, methylsulfinylethyl, ethylsulfinylethyl, ethylsulfinylmethyl, propylsulfinylmethyl, and butylsulfinylmethyl, $C_{1-6}$ alkylsulfonyl $C_{1-6}$ alkyl, such as methylsulfonylmethyl, methylsulfonylethyl, ethylsulfonylethyl, ethylsulfonylmethyl, propylsulfonylmethyl, and butylsulfonylmethyl, $C_{1-6}$ alkylcarbonyl, such as methylcarbonyl, ethylcarbonyl, propylcarbonyl, and butylcarbonyl, C$_{1-6}$ alkoxycarbonyl, such as methoxycarbonyl, ethoxycarbonyl, propoxycarbonyl, isopropoxycarbonyl, butoxycarbonyl, and t-butoxycarbonyl, phenyl C$_{1-6}$ alkyl optionally substituted by G$_2$, phenyl C$_{1-6}$ alkoxy optionally substituted by G$_2$, optionally substituted thienyl by G$_3$, optionally substituted pyridyl by G$_2$, pyridyloxy optionally substituted by G$_2$, phenyl optionally substituted by G4, or phenoxy optionally substituted by G$_4$;

wherein G$_2$ is C$_{1-6}$ alkyl, such as methyl, ethyl, n-propyl, isopropyl, n-butyl, sec-butyl, isobutyl, t-butyl, n-pentyl and isomers thereof, and n-hexyl and isomers thereof, halogeno, such as fluoro, chloro, bromo, and iodo, C$_{1-6}$ haloalkyl, such as chloromethyl, fluoromethyl, bromomethyl, dichloromethyl, difluoromethyl, dibromomethyl, trichloromethyl, trifluoromethyl, tribromomethyl, trichloroethyl, trifluoroethyl, and pentafluoroethyl, or C$_{1-6}$ haloalkoxy, such as chloromethoxy, fluoromethoxy, bromomethoxy, dichloromethoxy, difluoromethoxy, dibromomethoxy, trichloromethoxy, trifluoromethoxy, tribromomethoxy, 2,2,2-trichloroethoxy, 2,2,2-trifluoroethoxy, pentafluoroethoxy, and perfluoropropoxy, G$_3$ is C$_{1-6}$ alkyl, such as methyl, ethyl, n-propyl, isopropyl, n-butyl, sec-butyl, isobutyl, t-butyl, n-pentyl and isomers thereof, and n-hexyl and isomers thereof, or halogeno, such as fluoro, chloro, bromo, and iodo, G$_4$ is nitro, cyano, C$_{1-6}$ alkyl, such as methyl, ethyl, n-propyl, isopropyl, n-butyl, sec-butyl, isobutyl, t-butyl, n-pentyl and isomers thereof, and n-hexyl and isomers thereof, C$_{1-6}$ haloalkyl, such as chloromethyl, fluoromethyl, bromomethyl, dichloromethyl, difluoromethyl, dibromomethyl, trichloromethyl, trifluoromethyl, tribromomethyl, 2,2,2-trichloroethyl, 2,2,2-trifluoroethyl, and pentafluoroethyl, C$_{1-6}$ alkoxy, such as methoxy, ethoxy, n-propoxy, isopropoxy, n-butoxy, sec-butoxy, isobutoxy, and t-butoxy, C$_{1-6}$ haloalkoxy, such as chloromethoxy, dichloromethoxy, trichloromethoxy, trifluoromethoxy, 1-fluoroethoxy, and 1,1-difluoroethoxy, C$_{1-6}$ alkylthio, such as methylthio, ethylthioethyl, n-propylthio, isopropylthio, n-butylthio, isobutylthio, sec-butylthio, and t-butylthio, C$_{1-6}$ alkylsulfinyl, such as methylsulfinyl, ethylsulfinyl, n-propylsulfinyl, and n-butylsulfinyl, C$_{1-6}$ alkylsulfonyl, such as methylsulfonyl, ethylsulfonyl, n-propylsulfonyl, and n-butylsulfonyl, C$_{1-6}$ alkylamino, such as methylamino, ethylamino, n-propylamino, isopropylamino, n-butylamino, isobutylamino, sec-butylamino, t-butylamino, 1-methylbutylamino, and n-pentylamino, di-C$_{1-6}$ alkylamino, such as dimethylamino, diethylamino, dipropylamino, dibutylamino, ethylisopropylamino, and methylpropylamino, C$_{1-6}$ alkylcarbonyl, such as methylcarbonyl, ethylcarbonyl, n-propylcarbonyl, and n-butylcarbonyl, or C$_{1-6}$ alkoxycarbonyl, such as methoxycarbonyl, ethoxycarbonyl, n-propoxycarbonyl, isopropoxycarbonyl, n-butoxycarbonyl, and t-butoxycarbonyl;

n is 0 or an integer of 1 to 5, and when n is 2 or more, X may be same or different from each other, and Y is oxygen, sulfur, or nitrogen substituted by either hydrogen or C$_{1-6}$ alkyl, such as methyl, ethyl, n-propyl, isopropyl, n-butyl, sec-butyl, isobutyl and t-butyl.

The compounds of the present invention can be prerared, for example, according to the following process. Process for preparing a compound represented by the Formula (1) wherein R is hydrogen:

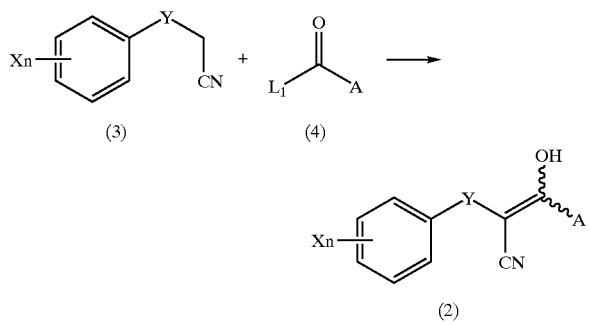

In the above reaction formula, A, X, Y and n are as defined above, and L$_1$ is halogeno, C$_{1-6}$ alkoxy, phenoxy, 1-imidazolyl, 1-pyrazolyl, p-toluenesulfonyloxy, methanesulfonyloxy, or an eliminating group, such as trifluoromethanesulfonyl.

A compound represented by the above Formula (2) is obtainable by causing a compound represented by the above Formula (3) to react with a compound represented by the above Formula (4) in the presence of a base. Examples of the base to be used in this reaction include sodium hydroxide, potassium hydroxide, sodium carbonate, potassium carbonate, n-butyl lithium, lithium diisopropylamide (LDA), sodium hydride, potassium hydride, triethylamine, diisopropylamine, pyridine, etc. Further, N,N-dimethylformamide (DMF), dimethylsulfoxide (DMSO), tetrahydrofuran (THF), acetonitrile, hexamethylphosphoric triamide (HMPT), benzene, toluene, dichloromethane, chloroform, carbon tetrachloride and the like may be used as the solvent to be used in the above reaction. The reaction temperature for the above reaction is preferably set at a temperature in a range of from −78° C. to the boiling point of the solvent used.

Note that the compounds represented by the above Formula (2) exist in tautomers of two forms, that is, the keto-form (2') and the enol-form (2), and all of these tautomers fall within the scope of the compounds of the present invention.

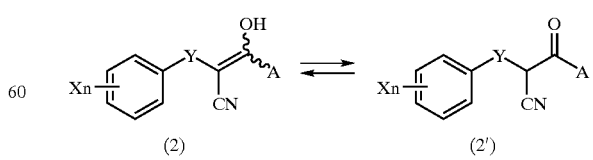

Process for producing a compound represented by the Formula (1) wherein R is a group other than hydrogen:

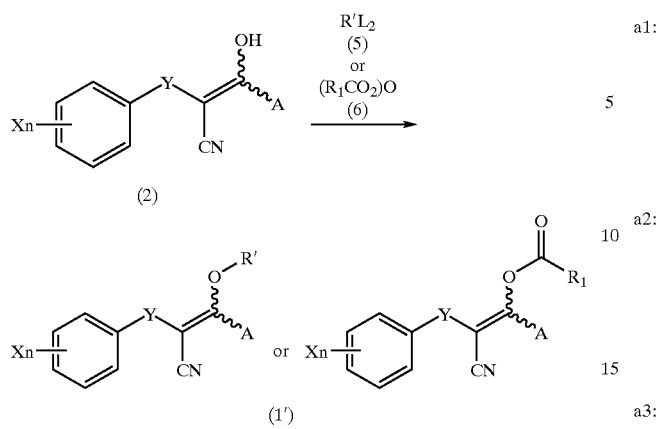

In the above reaction formula, A, $R_1$, X, Y and n are as defined above, R' is as defined above for R except hydrogen, and $L_2$ is halogeno, $C_{1-6}$ alkoxy, phenoxy, 1-imidazolyl, 1-pyrazolyl, p-toluenesulfonyloxy, methanesulfonyloxy, or an eliminating group such as trifluoromethanesulfonyloxy.

A compound represented by the above Formula (1') is obtainable by causing a compound represented by the above Formula (2) to react with a compound represented by the above Formula (5) or (6) in the presence of a base.

Examples of said base used for this reaction include alkali metal hydroxides, such as sodium hydroxide and potassium hydroxide, carbonates, such as sodium carbonate and potassium carbonate, organic metals, such as n-butyl lithium, LDA, metal hydrides, such as sodium hydride and potassium hydride, and organic bases, such as triethylamine, diisopropylamine and pyridine.

Further, solvents able to be used in the above reaction include DMF, DMSO, THF, acetonitrile, HMPT, benzene, toluene, dichloromethane, chloroform, carbon tetrachloride, and the like. Preferred reaction temperature are from −78° C. to the boiling point of solvent used.

Note that there are stereoisomers having the structural formula represented by Formula (1") in the compounds represented by the Formula (1) of the present invention. Depending on the reaction conditions and the purification process, either one of the isomers may be obtained, or the mixture of the isomers may be obtained, and it should be noted that all of these isomers fall within the scope of the compounds of the present invention.

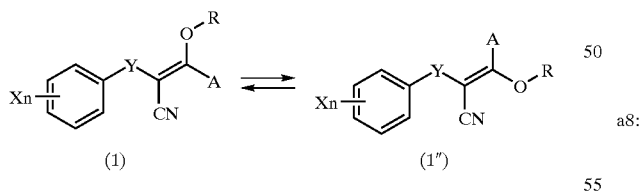

A target compound is obtained with usual post-treatments after the completion of the reaction.

The structures of the compounds of the present invention were determined by IR, MNR, MS and other means.

Representative examples of the compounds of the present invention, that can be prepared according to the above processes, are shown in Tables 1 and 2.

Note that the symbols used in the tables have the following meanings:
Me: methyl, Et: ethyl, Pr: propyl, Bu: butyl, Pen: pentyl, Hex: hexyl, Ph: phenyl, n: normal, i: iso, t: tertiary, c: cyclo a1: 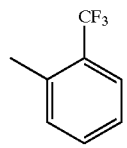

a2: 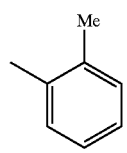

a3: 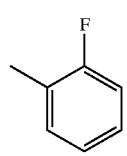

a4: 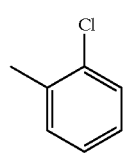

a5: 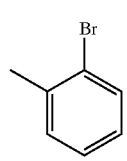

a6: 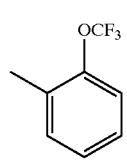

a7: 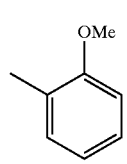

a8: 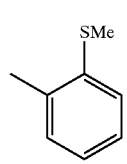

a9: 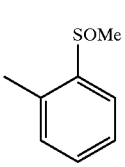

-continued
a10: 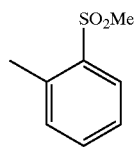
a11: 
a12: 
a13: 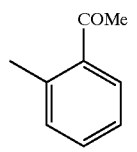
a14: 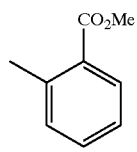
a15: 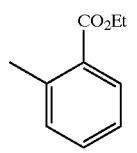
a16: 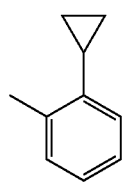
a17: 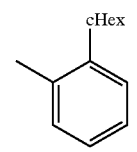
a18: 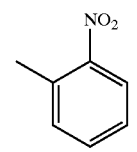
-continued
a19: 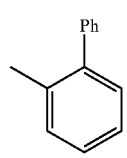
a20: 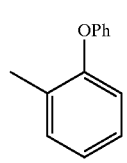
a21: 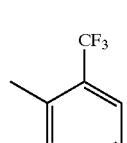
a22: 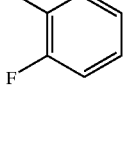
a23: 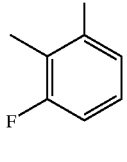
a24: 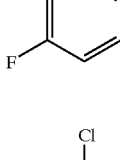
a25: 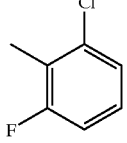
a26: 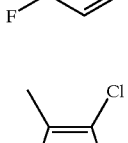
a27: 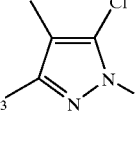

-continued a28: [4-methyl-5-fluoro-1,3-dimethylpyrazole]

a29: [3,4,5-trimethyl-1-methylpyrazole]

a30: [3,5-dichloro-4-methyl-1-methylpyrazole]

a31: [3-chloro-4-methyl-1-methylpyrazole]

a32: [5-chloro-1-methylpyrazole]

a33: [4,5-dimethyl-1-methylpyrazole]

a34: [1,3,5-trimethylpyrazole]

a35: [1,3,4,5-tetramethylpyrazole]

a36: [4-chloro-1,3,5-trimethylpyrazole]

a37: [1,3,5-trimethyl-1,2,4-triazole]

a38: [2,5-dimethyl-4-trifluoromethylthiazole]

a39: [2,5-dimethyl-4-trifluoromethyloxazole]

a40: [3,4,5-trimethylisoxazole]

a41: [3,4,5-trimethylisothiazole]

a42: [1,2,4,5-tetramethylimidazole]

a43: [1,5-dimethyltetrazole]

a44: [3,5-dimethyl-1,2,4-oxadiazole]

a45: [3,5-dimethyl-1,2,4-thiadiazole]

a46: [3,4,5-trimethylisoxazole]

a47: [3,4,5-trimethylisothiazole]

-continued
a48: 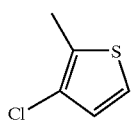
a49: 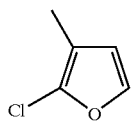
a50: 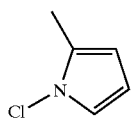
a51: 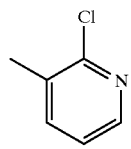
a52: 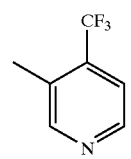
a53: 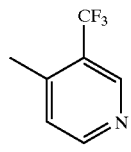
a54: 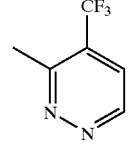
a56: 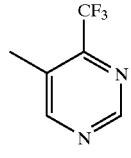
a57: 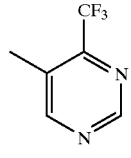
-continued
a58: 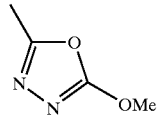
a59: 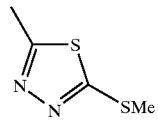
a60; 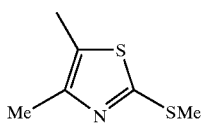
r1; 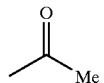
r2; 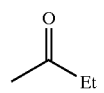
r3; 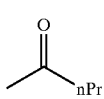
r4; 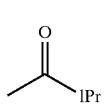
r5; 
r6; 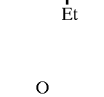
r7; 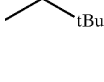
r8; 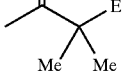
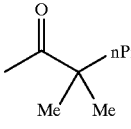

-continued
r9; 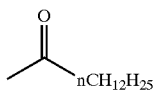
r10; 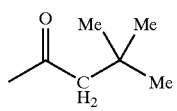
r11; 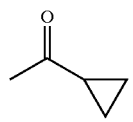
r12; 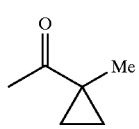
r13; 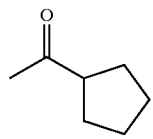
r14; 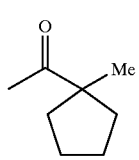
r15; 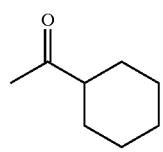
r16; 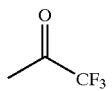
r17; 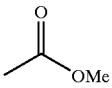
r18; 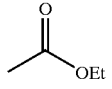
r19; 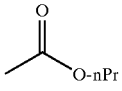
-continued
r20; 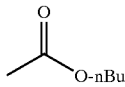
r21; 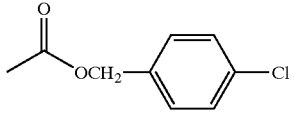
r22; 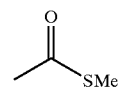
r23; 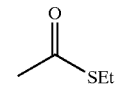
r24; 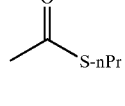
r25; 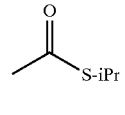
r26; 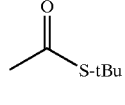
r27; 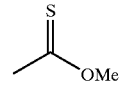
r28; 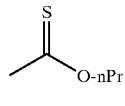
r29; 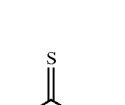
r30; 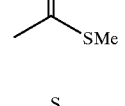
r31; 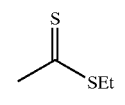
r32; 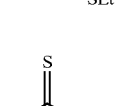

-continued
r33; 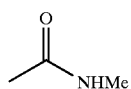
r34; 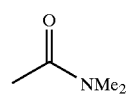
r35; 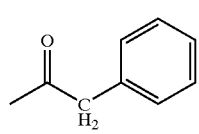
r36; 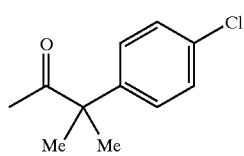
r37; 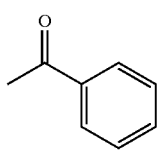
r38; 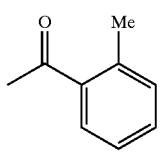
r39; 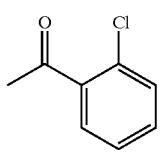
r40; 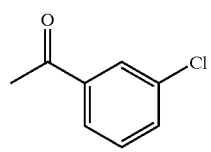
r41; 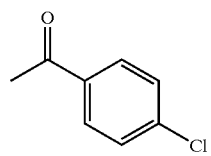
-continued
r42; 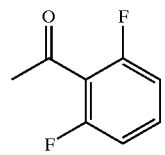
r43; 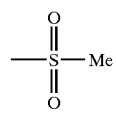
r44; 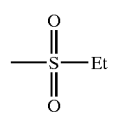
r45; 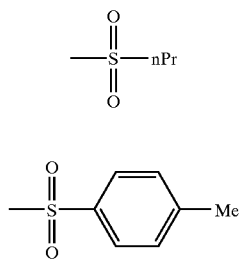
r46; 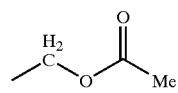
r47; 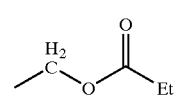
r48; 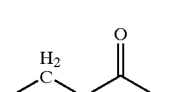
r49; 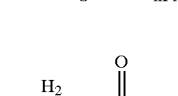
r50; 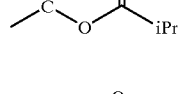
r51; 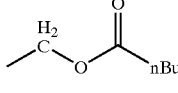
r52; 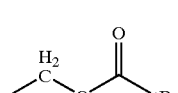
r53; 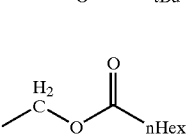

-continued
r54; 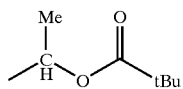
r55; 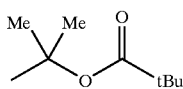
r56; 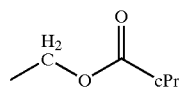
r57; 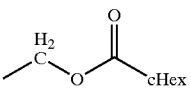
r58; 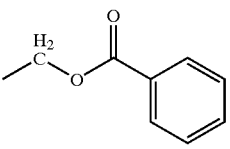
r59; 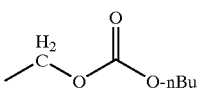
r60; 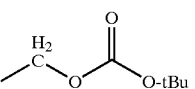
r61; 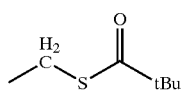
-continued
r62; 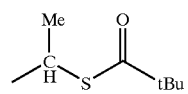
r63; 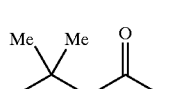
r64; 
r65; 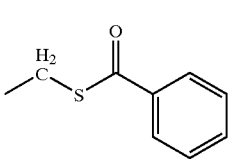
r66; 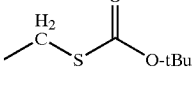
r67; 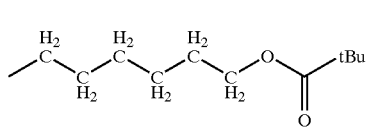
TABLE 1

TABLE 1-continued

Combinations of A, R and Xn of all compounds represented in the above formula 1-1 through 1-8 are exemplified in the following tables.

| A | R | Xn | A | R | Xn | A | R | Xn |
|---|---|---|---|---|---|---|---|---|
| a1 | r6 | — | a26 | r6 | 4-CN | a7 | r6 | 4-F |
| a2 | r6 | — | a35 | r6 | 4-CN | a8 | r6 | 4-F |
| a4 | r6 | — | a1 | r1 | 4-F | a9 | r6 | 4-F |
| a23 | r6 | — | a1 | r6 | 4-F | a10 | r6 | 4-F |
| a25 | r6 | — | a1 | r22 | 4-F | a11 | r6 | 4-F |
| a26 | r6 | — | a1 | r43 | 4-F | a12 | r6 | 4-F |
| a35 | r6 | — | a1 | r52 | 4-F | a13 | r6 | 4-F |
| a1 | r6 | 4-NO$_2$ | a2 | r1 | 4-F | a14 | r6 | 4-F |
| a2 | r6 | 4-NO$_2$ | a2 | r6 | 4-F | a15 | r6 | 4-F |
| a4 | r6 | 4-NO$_2$ | a2 | r22 | 4-F | a16 | r6 | 4-F |
| a23 | r6 | 4-NO$_2$ | a2 | r43 | 4-F | a17 | r6 | 4-F |
| a25 | r6 | 4-NO$_2$ | a2 | r52 | 4-F | a18 | r6 | 4-F |
| a26 | r6 | 4-NO$_2$ | a3 | r6 | 4-F | a19 | r6 | 4-F |
| a35 | r6 | 4-NO$_2$ | a3 | r22 | 4-F | a20 | r6 | 4-F |
| a1 | r6 | 4-CN | a4 | r6 | 4-F | a21 | r6 | 4-F |
| a2 | r6 | 4-CN | a4 | r22 | 4-F | a22 | r6 | 4-F |
| a4 | r6 | 4-CN | a5 | r6 | 4-F | a23 | r1 | 4-F |
| a23 | r6 | 4-CN | a5 | r22 | 4-F | a23 | r6 | 4-F |
| a25 | r6 | 4-CN | a6 | r6 | 4-F | a23 | r22 | 4-F |
| a23 | r43 | 4-F | a25 | r25 | 4-F | a25 | r56 | 4-F |
| a23 | r52 | 4-F | a25 | r26 | 4-F | a25 | r57 | 4-F |
| a24 | r1 | 4-F | a25 | r27 | 4-F | a25 | r58 | 4-F |
| a24 | r6 | 4-F | a25 | r28 | 4-F | a25 | r59 | 4-F |
| a24 | r22 | 4-F | a25 | r29 | 4-F | a25 | r60 | 4-F |
| a24 | r43 | 4-F | a25 | r30 | 4-F | a25 | r61 | 4-F |
| a24 | r52 | 4-F | a25 | r31 | 4-F | a25 | r62 | 4-F |
| a25 | r1 | 4-F | a25 | r32 | 4-F | a25 | r63 | 4-F |
| a25 | r2 | 4-F | a25 | r33 | 4-F | a25 | r64 | 4-F |
| a25 | r3 | 4-F | a25 | r34 | 4-F | a25 | r65 | 4-F |
| a25 | r4 | 4-F | a25 | r35 | 4-F | a25 | r66 | 4-F |
| a25 | r5 | 4-F | a25 | r36 | 4-F | a25 | r67 | 4-F |
| a25 | r6 | 4-F | a25 | r37 | 4-F | a25 | CH$_2$OEt | 4-F |
| a25 | r7 | 4-F | a25 | r38 | 4-F | a25 | CH$_2$SEt | 4-F |
| a25 | r8 | 4-F | a25 | r39 | 4-F | a25 | CH$_2$Ph | 4-F |
| a25 | r9 | 4-F | a25 | r40 | 4-F | a25 | Me | 4-F |
| a25 | r10 | 4-F | a25 | r41 | 4-F | a25 | nHex | 4-F |
| a25 | r11 | 4-F | a25 | r42 | 4-F | a26 | r1 | 4-F |
| a25 | r12 | 4-F | a25 | r43 | 4-F | a26 | r6 | 4-F |
| a25 | r13 | 4-F | a25 | r44 | 4-F | a26 | r22 | 4-F |
| a25 | r14 | 4-F | a25 | r45 | 4-F | a26 | r43 | 4-F |
| a25 | r15 | 4-F | a25 | r46 | 4-F | a26 | r52 | 4-F |
| a25 | r16 | 4-F | a25 | r47 | 4-F | a27 | r1 | 4-F |
| a25 | r17 | 4-F | a25 | r48 | 4-F | a27 | r6 | 4-F |
| a25 | r18 | 4-F | a25 | r49 | 4-F | a27 | r22 | 4-F |
| a25 | r19 | 4-F | a25 | r50 | 4-F | a27 | r43 | 4-F |
| a25 | r20 | 4-F | a25 | r51 | 4-F | a27 | r52 | 4-F |
| a25 | r21 | 4-F | a25 | r52 | 4-F | a28 | r1 | 4-F |
| a25 | r22 | 4-F | a25 | r53 | 4-F | a28 | r6 | 4-F |
| a25 | r23 | 4-F | a25 | r54 | 4-F | a28 | r22 | 4-F |
| a25 | r24 | 4-F | a25 | r55 | 4-F | a28 | r43 | 4-F |
| a28 | r52 | 4-F | a35 | r6 | 4-F | a44 | r6 | 4-F |
| a29 | r1 | 4-F | a35 | r22 | 4-F | a45 | r6 | 4-F |
| a29 | r6 | 4-F | a35 | r43 | 4-F | a46 | r6 | 4-F |
| a29 | r22 | 4-F | a35 | r52 | 4-F | a47 | r6 | 4-F |
| a29 | r43 | 4-F | a36 | r1 | 4-F | a48 | r6 | 4-F |
| a29 | r52 | 4-F | a36 | r6 | 4-F | a49 | r6 | 4-F |
| a30 | r1 | 4-F | a36 | r22 | 4-F | a50 | r6 | 4-F |
| a30 | r6 | 4-F | a36 | r43 | 4-F | a51 | r6 | 4-F |
| a30 | r22 | 4-F | a36 | r52 | 4-F | a52 | r6 | 4-F |
| a30 | r43 | 4-F | a37 | r6 | 4-F | a53 | r6 | 4-F |
| a30 | r52 | 4-F | a38 | r1 | 4-F | a54 | r6 | 4-F |
| a31 | r1 | 4-F | a38 | r6 | 4-F | a55 | r6 | 4-F |
| a31 | r6 | 4-F | a38 | r22 | 4-F | a56 | r6 | 4-F |
| a31 | r22 | 4-F | a38 | r43 | 4-F | a57 | r6 | 4-F |
| a31 | r43 | 4-F | a38 | r52 | 4-F | a58 | r6 | 4-F |
| a31 | r52 | 4-F | a39 | r1 | 4-F | a59 | r6 | 4-F |
| a32 | r1 | 4-F | a39 | r6 | 4-F | a1 | r1 | 4-Cl |
| a32 | r6 | 4-F | a39 | r22 | 4-F | a1 | r6 | 4-Cl |
| a32 | r22 | 4-F | a39 | r43 | 4-F | a1 | 22 | 4-Cl |
| a32 | r43 | 4-F | a39 | r52 | 4-F | a1 | r43 | 4-Cl |
| a32 | r52 | 4-F | a40 | r1 | 4-F | a1 | r52 | 4-Cl |
| a33 | r1 | 4-F | a40 | r6 | 4-F | a2 | r1 | 4-Cl |
| a33 | r6 | 4-F | a40 | r22 | 4-F | a2 | r6 | 4-Cl |

TABLE 1-continued

| | | | | | | | | |
|---|---|---|---|---|---|---|---|---|
| a33 | r22 | 4-F | a40 | r43 | 4-F | a2 | r22 | 4-Cl |
| a33 | r43 | 4-F | a40 | r52 | 4-F | a2 | r43 | 4-Cl |
| a33 | r52 | 4-F | a41 | r1 | 4-F | a2 | r52 | 4-Cl |
| a34 | r1 | 4-F | a41 | r6 | 4-F | a3 | r6 | 4-Cl |
| a34 | r6 | 4-F | a41 | r22 | 4-F | a3 | r22 | 4-Cl |
| a34 | r22 | 4-F | a41 | r43 | 4-F | a4 | r6 | 4-Cl |
| a34 | r43 | 4-F | a41 | r52 | 4-F | a4 | r22 | 4-Cl |
| a34 | r52 | 4-F | a42 | r6 | 4-F | a5 | r6 | 4-Cl |
| a35 | r1 | 4-F | a43 | r6 | 4-F | a5 | r22 | 4-Cl |
| a6 | r6 | 4-Cl | a25 | r5 | 4-Cl | a25 | r36 | 4-Cl |
| a7 | r6 | 4-Cl | a25 | r6 | 4-Cl | a25 | r37 | 4-Cl |
| a8 | r6 | 4-Cl | a25 | r7 | 4-Cl | a25 | r38 | 4-Cl |
| a9 | r6 | 4-Cl | a25 | r8 | 4-Cl | a25 | r39 | 4-Cl |
| a10 | r6 | 4-Cl | a25 | r9 | 4-Cl | a25 | r40 | 4-Cl |
| a11 | r6 | 4-Cl | a25 | r10 | 4-Cl | a25 | r41 | 4-Cl |
| a12 | r6 | 4-Cl | a25 | r1 | 4-Cl | a25 | r42 | 4-Cl |
| a13 | r6 | 4-Cl | a25 | r12 | 4-Cl | a25 | r43 | 4-Cl |
| a14 | r6 | 4-Cl | a25 | r13 | 4-Cl | a25 | r44 | 4-Cl |
| a15 | r6 | 4-Cl | a25 | r14 | 4-Cl | a25 | r45 | 4-Cl |
| a16 | r6 | 4-Cl | a25 | r15 | 4-Cl | a25 | r46 | 4-Cl |
| a17 | r6 | 4-Cl | a25 | r16 | 4-Cl | a25 | r47 | 4-Cl |
| a18 | r6 | 4-Cl | a25 | r17 | 4-Cl | a25 | r48 | 4-Cl |
| a19 | r6 | 4-Cl | a25 | r18 | 4-Cl | a25 | r49 | 4-Cl |
| a20 | r6 | 4-Cl | a25 | r19 | 4-Cl | a25 | r50 | 4-Cl |
| a21 | r6 | 4-Cl | a25 | r20 | 4-Cl | a25 | r51 | 4-Cl |
| a22 | r6 | 4-Cl | a25 | r21 | 4-Cl | a25 | r52 | 4-Cl |
| a23 | r1 | 4-Cl | a25 | r22 | 4-Cl | a25 | r53 | 4-Cl |
| a23 | r6 | 4-Cl | a25 | r23 | 4-Cl | a25 | r54 | 4-Cl |
| a23 | r22 | 4-Cl | a25 | r24 | 4-Cl | a25 | r55 | 4-Cl |
| a23 | r43 | 4-Cl | a25 | r25 | 4-Cl | a25 | r56 | 4-Cl |
| a23 | r52 | 4-Cl | a25 | r26 | 4-Cl | a26 | r57 | 4-Cl |
| a24 | r1 | 4-Cl | a25 | r27 | 4-Cl | a25 | r58 | 4-Cl |
| a24 | r6 | 4-Cl | a25 | r28 | 4-Cl | a25 | r59 | 4-Cl |
| a24 | r22 | 4-Cl | a25 | r29 | 4-Cl | a25 | r60 | 4-Cl |
| a24 | r43 | 4-Cl | a25 | r30 | 4-Cl | a25 | r61 | 4-Cl |
| a24 | r52 | 4-Cl | a25 | r31 | 4-Cl | a25 | r62 | 4-Cl |
| a25 | r1 | 4-Cl | a25 | r32 | 4-Cl | a25 | r63 | 4-Cl |
| a25 | r2 | 4-Cl | a25 | r33 | 4-Cl | a25 | r64 | 4-Cl |
| a25 | r3 | 4-Cl | a25 | r34 | 4-Cl | a25 | r65 | 4-Cl |
| a25 | r4 | 4-Cl | a25 | r35 | 4-Cl | a26 | r66 | 4-Cl |
| a25 | r67 | 4-Cl | a31 | r6 | 4-Cl | a38 | r22 | 4-Cl |
| a25 | $CH_2OEt$ | 4-Cl | a31 | r22 | 4-Cl | a38 | r43 | 4-Cl |
| a25 | $CH_2SEt$ | 4-Cl | a31 | r43 | 4-Cl | a38 | r52 | 4-Cl |
| a25 | $CH_2Ph$ | 4-Cl | a31 | r52 | 4-Cl | a39 | r1 | 4-Cl |
| a25 | Me | 4-Cl | a32 | r1 | 4-Cl | a39 | r6 | 4-Cl |
| a25 | nHex | 4-Cl | a32 | r6 | 4-Cl | a39 | r22 | 4-Cl |
| a26 | r1 | 4-Cl | a32 | r22 | 4-Cl | a39 | r43 | 4-Cl |
| a26 | r6 | 4-Cl | a32 | r43 | 4-Cl | a39 | r52 | 4-Cl |
| a26 | r22 | 4-Cl | a32 | r52 | 4-Cl | a40 | r1 | 4-Cl |
| a26 | r43 | 4-Cl | a33 | r1 | 4-Cl | a40 | r6 | 4-Cl |
| a26 | r52 | 4-Cl | a33 | r6 | 4-Cl | a40 | r22 | 4-Cl |
| a27 | r1 | 4-Cl | a33 | r22 | 4-Cl | a40 | r43 | 4-Cl |
| a27 | r6 | 4-Cl | a33 | r43 | 4-Cl | a40 | r52 | 4-Cl |
| a27 | r22 | 4-Cl | a33 | r52 | 4-Cl | a41 | r1 | 4-Cl |
| a27 | r43 | 4-Cl | a34 | r1 | 4-Cl | a41 | r6 | 4-Cl |
| a27 | r52 | 4-Cl | a34 | r6 | 4-Cl | a41 | r22 | 4-Cl |
| a28 | r1 | 4-Cl | a34 | r22 | 4-Cl | a41 | r43 | 4-Cl |
| a28 | r6 | 4-Cl | a34 | r43 | 4-Cl | a41 | r52 | 4-Cl |
| a28 | r22 | 4-Cl | a34 | r52 | 4-Cl | a42 | r6 | 4-Cl |
| a28 | r43 | 4-Cl | a35 | r1 | 4-Cl | a43 | r6 | 4-Cl |
| a28 | r52 | 4-Cl | a35 | r6 | 4-Cl | a44 | r6 | 4-Cl |
| a29 | r1 | 4-Cl | a35 | r22 | 4-Cl | a45 | r6 | 4-Cl |
| a29 | r6 | 4-Cl | a35 | r43 | 4-Cl | a46 | r6 | 4-Cl |
| a29 | r22 | 4-Cl | a35 | r52 | 4-Cl | a47 | r6 | 4-Cl |
| a29 | r43 | 4-Cl | a36 | r1 | 4-Cl | a48 | r6 | 4-Cl |
| a29 | r52 | 4-Cl | a36 | r6 | 4-Cl | a49 | r6 | 4-Cl |
| a30 | r1 | 4-Cl | a36 | r22 | 4-Cl | a50 | r6 | 4-Cl |
| a30 | r6 | 4-Cl | a36 | r43 | 4-Cl | a51 | r6 | 4-Cl |
| a30 | r22 | 4-Cl | a36 | r52 | 4-Cl | a52 | r6 | 4-Cl |
| a30 | r43 | 4-Cl | a37 | r6 | 4-Cl | a53 | r6 | 4-Cl |
| a30 | r52 | 4-Cl | a38 | r1 | 4-Cl | a54 | r6 | 4-Cl |
| a31 | r1 | 4-Cl | a38 | r6 | 4-Cl | a55 | r6 | 4-Cl |
| a56 | r6 | 4-Cl | a35 | r6 | 4-iPr | a1 | r22 | 4-$CF_3$ |
| a57 | r6 | 4-Cl | a1 | r6 | 4-tBu | a1 | r43 | 4-$CF_3$ |
| a58 | r6 | 4-Cl | a2 | r6 | 4-tBu | a1 | r52 | 4-$CF_3$ |
| a59 | r6 | 4-Cl | a4 | r6 | 4-tBu | a2 | r1 | 4-$CF_3$ |
| a1 | r6 | 4-Br | a23 | r6 | 4-tBu | a2 | r6 | 4-$CF_3$ |
| a2 | r6 | 4-Br | a25 | r6 | 4-tBu | a2 | r22 | 4-$CF_3$ |
| a4 | r6 | 4-Br | a26 | r6 | 4-tBu | a2 | r43 | 4-$CF_3$ |

TABLE 1-continued

| | | | | | | | | |
|---|---|---|---|---|---|---|---|---|
| a23 | r6 | 4-Br | a35 | r6 | 4-tBu | a2 | r52 | 4-CF$_3$ |
| a25 | r6 | 4-Br | a1 | r6 | 4-nHex | a3 | r6 | 4-CF$_3$ |
| a26 | r6 | 4-Br | a2 | r6 | 4-nHex | a3 | r22 | 4-CF$_3$ |
| a35 | r6 | 4-Br | a4 | r6 | 4-nHex | a4 | r6 | 4-CF$_3$ |
| a1 | r6 | 4-I | a23 | r6 | 4-nHex | a4 | r22 | 4-CF$_3$ |
| a2 | r6 | 4-I | a25 | r6 | 4-nHex | a5 | r6 | 4-CF$_3$ |
| a4 | r6 | 4-I | a26 | r6 | 4-nHex | a5 | r22 | 4-CF$_3$ |
| a23 | r6 | 4-I | a35 | r6 | 4-nHex | a6 | r6 | 4-CF$_3$ |
| a25 | r6 | 4-I | a1 | r6 | 4-cPr | a7 | r6 | 4-CF$_3$ |
| a26 | r6 | 4-I | a2 | r6 | 4-cPr | a8 | r6 | 4-CF$_3$ |
| a35 | r6 | 4-I | a4 | r6 | 4-cPr | a9 | r6 | 4-CF$_3$ |
| a1 | r6 | 4-Me | a23 | r6 | 4-cPr | a10 | r6 | 4-CF$_3$ |
| a2 | r6 | 4-Me | a25 | r6 | 4-cPr | a11 | r6 | 4-CF$_3$ |
| a4 | r6 | 4-Me | a26 | r6 | 4-cPr | a12 | r6 | 4-CF$_3$ |
| a23 | r6 | 4-Me | a35 | r6 | 4-cPr | a13 | r6 | 4-CF$_3$ |
| a25 | r6 | 4-Me | a1 | r6 | 4-cHex | a14 | r6 | 4-CF$_3$ |
| a26 | r6 | 4-Me | a2 | r6 | 4-cHex | a15 | r6 | 4-CF$_3$ |
| a35 | r6 | 4-Me | a4 | r6 | 4-cHex | a16 | r6 | 4-CF$_3$ |
| a1 | r6 | 4-iPr | a23 | r6 | 4-cHex | a17 | r6 | 4-CF$_3$ |
| a2 | r6 | 4-iPr | a25 | r6 | 4-cHex | a18 | r6 | 4-CF$_3$ |
| a4 | r6 | 4-iPr | a26 | r6 | 4-cHex | a19 | r6 | 4-CF$_3$ |
| a23 | r6 | 4-iPr | a35 | r6 | 4-cHex | a20 | r6 | 4-CF$_3$ |
| a25 | r6 | 4-iPr | a1 | r1 | 4-CF$_3$ | a21 | r6 | 4-CF$_3$ |
| a26 | r6 | 4-iPr | a1 | r6 | 4-CF$_3$ | a22 | r6 | 4-CF$_3$ |
| a23 | r1 | 4-CF$_3$ | a25 | r22 | 4-CF$_3$ | a25 | r53 | 4-CF$_3$ |
| a23 | r6 | 4-CF$_3$ | a25 | r23 | 4-CF$_3$ | a25 | r54 | 4-CF$_3$ |
| a23 | r22 | 4-CF$_3$ | a25 | r24 | 4-CF$_3$ | a25 | r55 | 4-CF$_3$ |
| a23 | r43 | 4-CF$_3$ | a25 | r25 | 4-CF$_3$ | a25 | r56 | 4-CF$_3$ |
| a23 | r52 | 4-CF$_3$ | a25 | r26 | 4-CF$_3$ | a25 | r57 | 4-CF$_3$ |
| a24 | r1 | 4-CF$_3$ | a25 | r27 | 4-CF$_3$ | a25 | r58 | 4-CF$_3$ |
| a24 | r6 | 4-CF$_3$ | a25 | r28 | 4-CF$_3$ | a25 | r59 | 4-CF$_3$ |
| a24 | r22 | 4-CF$_3$ | a25 | r29 | 4-CF$_3$ | a25 | r60 | 4-CF$_3$ |
| a24 | r43 | 4-CF$_3$ | a25 | r30 | 4-CF$_3$ | a25 | r61 | 4-CF$_3$ |
| a24 | r52 | 4-CF$_3$ | a25 | r31 | 4-CF$_3$ | a25 | r62 | 4-CF$_3$ |
| a25 | r1 | 4-CF$_3$ | a25 | r32 | 4-CF$_3$ | a25 | r63 | 4-CF$_3$ |
| a25 | r2 | 4-CF$_3$ | a25 | r33 | 4-CF$_3$ | a25 | r64 | 4-CF$_3$ |
| a25 | r3 | 4-CF$_3$ | a25 | r34 | 4-CF$_3$ | a25 | r65 | 4-CF$_3$ |
| a25 | r4 | 4-CF$_3$ | a25 | r35 | 4-CF$_3$ | a25 | r66 | 4-CF$_3$ |
| a25 | r5 | 4-CF$_3$ | a25 | r36 | 4-CF$_3$ | a25 | r67 | 4-CF$_3$ |
| a25 | r6 | 4-CF$_3$ | a25 | r37 | 4-CF$_3$ | a25 | CH$_2$OEt | 4-CF$_3$ |
| a25 | r7 | 4-CF$_3$ | a25 | r38 | 4-CF$_3$ | a25 | CH$_2$SEt | 4-CF$_3$ |
| a25 | r8 | 4-CF$_3$ | a25 | r39 | 4-CF$_3$ | a25 | CH$_2$Ph | 4-CF$_3$ |
| a25 | r9 | 4-CF$_3$ | a25 | r40 | 4-CF$_3$ | a25 | Me | 4-CF$_3$ |
| a25 | r10 | 4-CF$_3$ | a25 | r41 | 4-CF$_3$ | a25 | nHex | 4-CF$_3$ |
| a25 | r1 | 4-CF$_3$ | a25 | r42 | 4-CF$_3$ | a26 | r1 | 4-CF$_3$ |
| a25 | n12 | 4-CF$_3$ | a25 | r43 | 4-CF$_3$ | a26 | r6 | 4-CF$_3$ |
| a25 | n13 | 4-CF$_3$ | a25 | r44 | 4-CF$_3$ | a26 | r22 | 4-CF$_3$ |
| a25 | n14 | 4-CF$_3$ | a25 | r45 | 4-CF$_3$ | a26 | r43 | 4-CF$_3$ |
| a25 | n15 | 4-CF$_3$ | a25 | r46 | 4-CF$_3$ | a26 | r52 | 4-CF$_3$ |
| a25 | r16 | 4-CF$_3$ | a25 | r47 | 4-CF$_3$ | a27 | r1 | 4-CF$_3$ |
| a25 | n17 | 4-CF$_3$ | a25 | r48 | 4-CF$_3$ | a27 | r6 | 4-CF$_3$ |
| a25 | n18 | 4-CF$_3$ | a25 | r49 | 4-CF$_3$ | a27 | r22 | 4-CF$_3$ |
| a25 | n19 | 4-CF$_3$ | a25 | r50 | 4-CF$_3$ | a27 | r43 | 4-CF$_3$ |
| a25 | r20 | 4-CF$_3$ | a25 | r51 | 4-CF$_3$ | a27 | r52 | 4-CF$_3$ |
| a25 | r21 | 4-CF$_3$ | a25 | r52 | 4-CF$_3$ | a28 | r1 | 4-CF$_3$ |
| a28 | r6 | 4-CF$_3$ | a34 | r43 | 4-CF$_3$ | a41 | r52 | 4-CF$_3$ |
| a28 | r22 | 4-CF$_3$ | a34 | r52 | 4-CF$_3$ | a42 | r6 | 4-CF$_3$ |
| a28 | r43 | 4-CF$_3$ | a35 | r1 | 4-CF$_3$ | a43 | r6 | 4-CF$_3$ |
| a28 | r52 | 4-CF$_3$ | a35 | r6 | 4-CF$_3$ | a44 | r6 | 4-CF$_3$ |
| a29 | r1 | 4-CF$_3$ | a35 | r22 | 4-CF$_3$ | a45 | r6 | 4-CF$_3$ |
| a29 | r6 | 4-CF$_3$ | a35 | r43 | 4-CF$_3$ | a46 | r6 | 4-CF$_3$ |
| a29 | r22 | 4-CF$_3$ | a35 | r52 | 4-CF$_3$ | a47 | r6 | 4-CF$_3$ |
| a29 | r43 | 4-CF$_3$ | a36 | r1 | 4-CF$_3$ | a48 | r6 | 4-CF$_3$ |
| a29 | r52 | 4-CF$_3$ | a36 | r6 | 4-CF$_3$ | a49 | r6 | 4-CF$_3$ |
| a30 | r1 | 4-CF$_3$ | a36 | r22 | 4-CF$_3$ | a50 | r6 | 4-CF$_3$ |
| a30 | r6 | 4-CF$_3$ | a36 | r43 | 4-CF$_3$ | a51 | r6 | 4-CF$_3$ |
| a30 | r22 | 4-CF$_3$ | a36 | r52 | 4-CF$_3$ | a52 | r6 | 4-CF$_3$ |
| a30 | r43 | 4-CF$_3$ | a37 | r6 | 4-CF$_3$ | a53 | r6 | 4-CF$_3$ |
| a30 | r52 | 4-CF$_3$ | a38 | r1 | 4-CF$_3$ | a54 | r6 | 4-CF$_3$ |
| a31 | r1 | 4-CF$_3$ | a38 | r6 | 4-CF$_3$ | a55 | r6 | 4-CF$_3$ |
| a31 | r6 | 4-CF$_3$ | a38 | r22 | 4-CF$_3$ | a56 | r6 | 4-CF$_3$ |
| a31 | r22 | 4-CF$_3$ | a38 | r43 | 4-CF$_3$ | a57 | r6 | 4-CF$_3$ |
| a31 | r43 | 4-CF$_3$ | a38 | r52 | 4-CF$_3$ | a58 | r6 | 4-CF$_3$ |
| a31 | r52 | 4-CF$_3$ | a39 | r1 | 4-CF$_3$ | a59 | r6 | 4-OMe |
| a32 | r1 | 4-CF$_3$ | a39 | r6 | 4-CF$_3$ | a1 | r6 | 4-OMe |
| a32 | r6 | 4-CF$_3$ | a39 | r22 | 4-CF$_3$ | a2 | r6 | 4-OMe |
| a32 | r22 | 4-CF$_3$ | a39 | r43 | 4-CF$_3$ | a4 | r6 | 4-OMe |
| a32 | r43 | 4-CF$_3$ | a39 | r52 | 4-CF$_3$ | a23 | r6 | 4-OMe |
| a32 | r52 | 4-CF$_3$ | a40 | r1 | 4-CF$_3$ | a25 | r6 | 4-OMe |

TABLE 1-continued

| | | | | | | | | |
|---|---|---|---|---|---|---|---|---|
| a33 | r1 | 4-CF$_3$ | a40 | r6 | 4-CF$_3$ | a26 | r6 | 4-OMe |
| a33 | r6 | 4-CF$_3$ | a40 | r22 | 4-CF$_3$ | a35 | r6 | 4-OMe |
| a33 | r22 | 4-CF$_3$ | a40 | r43 | 4-CF$_3$ | a1 | r6 | 4-OiPr |
| a33 | r43 | 4-CF$_3$ | a40 | r52 | 4-CF$_3$ | a2 | r6 | 4-OiPr |
| a33 | r52 | 4-CF$_3$ | a41 | r1 | 4-CF$_3$ | a4 | r6 | 4-OiPr |
| a34 | r1 | 4-CF$_3$ | a41 | r6 | 4-CF$_3$ | a23 | r6 | 4-OiPr |
| a34 | r6 | 4-CF$_3$ | a41 | r22 | 4-CF$_3$ | a25 | r6 | 4-OiPr |
| a34 | r22 | 4-CF$_3$ | a41 | r43 | 4-CF$_3$ | a26 | r6 | 4-OiPr |
| a35 | r6 | 4-OiPr | a25 | r6 | 4-COMe | a2 | r6 | 2-Cl |
| a1 | r6 | 4-OtBu | a35 | r6 | 4-COMe | a4 | r6 | 2-Cl |
| a2 | r6 | 4-OtBu | a25 | r6 | 4-COtBu | a23 | r6 | 2-Cl |
| a4 | r6 | 4-OtBu | a35 | r6 | 4-COtBu | a25 | r6 | 2-Cl |
| a23 | r6 | 4-OtBu | a25 | r6 | 4-CO$_2$Me | a26 | r6 | 2-Cl |
| a25 | r6 | 4-OtBu | a35 | r6 | 4-CO$_2$Me | a35 | r6 | 2-Cl |
| a26 | r6 | 4-OtBu | a25 | r6 | 4-CO$_2$tBu | a1 | r6 | 3-Cl |
| a35 | r6 | 4-OtBu | a35 | r6 | 4-CO$_2$tBu | a2 | r6 | 3-Cl |
| a1 | r6 | 4-OCF$_3$ | a25 | r6 | 4-CH$_2$Ph | a4 | r6 | 3-Cl |
| a2 | r6 | 4-OCF$_3$ | a35 | r6 | 4-CH$_2$Ph | a23 | r6 | 3-Cl |
| a4 | r6 | 4-OCF$_3$ | a25 | r6 | 4-OCH$_2$Ph | a25 | r6 | 3-Cl |
| a23 | r6 | 4-OCF$_3$ | a35 | r6 | 4-OCH$_{2Ph}$ | a26 | r6 | 3-Cl |
| a25 | r6 | 4-OCF$_3$ | a25 | r6 | 4-(2-thienyl) | a35 | r6 | 3-Cl |
| a26 | r6 | 4-OCF$_3$ | a35 | r6 | 4-(2-thienyl) | a1 | r6 | 2,4-F$_2$ |
| a35 | r6 | 4-OCF$_3$ | a25 | r6 | 4-(3-thienyl) | a2 | r6 | 2,4-F$_2$ |
| a25 | r6 | 4-SMe | a35 | r6 | 4-(3-thienyl) | a4 | r6 | 2,4-F$_2$ |
| a35 | r6 | 4-SMe | a25 | r6 | 4-(2-pyridyl) | a23 | r6 | 2,4-F$_2$ |
| a25 | r6 | 4-SOMe | a35 | r6 | 4-(2-pyridyl) | a25 | r6 | 2,4-F$_2$ |
| a35 | r6 | 4-SOMe | a25 | r6 | 4-(3-pyridyl) | a26 | r6 | 2,4-F$_2$ |
| a25 | r6 | 4-SO$_2$Me | a35 | r6 | 4-(3-pyridyl) | a35 | r6 | 2,4-F$_2$ |
| a35 | r6 | 4-SO$_2$Me | a25 | r6 | 4-(4-pyridyl) | a1 | r6 | 2,6-F$_2$ |
| a25 | r6 | 4-NHMe | a35 | r6 | 4-(4-pyridyl) | a2 | r6 | 2,6-F$_2$ |
| a35 | r6 | 4-NHMe | a25 | r6 | 4-Ph | a4 | r6 | 2,6-F$_2$ |
| a25 | r6 | 4-NMe$_2$ | a35 | r6 | 4-Ph | a23 | r6 | 2,6-F$_2$ |
| a35 | r6 | 4-NMe$_2$ | a25 | r6 | 4-(4-Cl-Ph) | a25 | r6 | 2,6-F$_2$ |
| a25 | r6 | 4-SiMe$_4$ | a35 | r6 | 4-(4-Cl-Ph) | a26 | r6 | 2,6-F$_2$ |
| a35 | r6 | 4-SiMe$_4$ | a25 | r6 | 4-(4-F-Ph) | a35 | r6 | 2,6-F$_2$ |
| a25 | r6 | 4-CH$_2$OEt | a35 | r6 | 4-(4-F-Ph) | al | r6 | 2,4-Cl$_2$ |
| a35 | r6 | 4-CH$_2$OEt | a25 | r6 | 4-OPh | a2 | r6 | 2,4-Cl$_2$ |
| a25 | r6 | 4-CH$_2$SEt | a35 | r6 | 4-OPh | a4 | r6 | 2,4-Cl$_2$ |
| a35 | r6 | 4-CH$_2$SEt | a1 | r6 | 2-Cl | a23 | r6 | 2,4-Cl$_2$ |
| a25 | r6 | 2,4-Cl$_2$ | a1 | r6 | 2-OEt-4-tBu | | | |
| a26 | r6 | 2,4-Cl$_2$ | a2 | r6 | 2-OEt-4-tBu | | | |
| a35 | r6 | 2,4-Cl$_2$ | a4 | r6 | 2-OEt-4-tBu | | | |
| a1 | r6 | 2,6-Cl$_2$ | a23 | r6 | 2-OEt-4-tBu | | | |
| a2 | r6 | 2,6-Cl$_2$ | a25 | r6 | 2-OEt-4-tBu | | | |
| a4 | r6 | 2,6-Cl$_2$ | a26 | r6 | 2-OEt-4-tBu | | | |
| a23 | r6 | 2,6-Cl$_2$ | a35 | r6 | 2-OEt-4-tBu | | | |
| a25 | r6 | 2,6-Cl$_2$ | a1 | r6 | 4-(4-OCF$_3$-Ph) | | | |
| a26 | r6 | 2,6-Cl$_2$ | a2 | r6 | 4-(4-OCF$_3$-Ph) | | | |
| a35 | r6 | 2,6-Cl$_2$ | a4 | r6 | 4-(4-OCF$_3$-Ph) | | | |
| a1 | r6 | 2,4,6-Cl$_3$ | a23 | r6 | 4-(4-OCF$_3$-Ph) | | | |
| a2 | r6 | 2,4,6-Cl$_3$ | a25 | r6 | 4-(4-OCF$_3$-Ph) | | | |
| a4 | r6 | 2,4,6-Cl$_3$ | a26 | r6 | 4-(4-OCF$_3$-Ph) | | | |
| a23 | r6 | 2,4,6-Cl$_3$ | a35 | r6 | 4-(4-OCF$_3$-Ph) | | | |
| a25 | r6 | 2,4,6-Cl$_3$ | a1 | r6 | 4-O-(2-pyridyl) | | | |
| a26 | r6 | 2,4,6-Cl$_3$ | a2 | r6 | 4-O-(2-pyridyl) | | | |
| a35 | r6 | 2,4,6-Cl$_3$ | a4 | r6 | 4-O-(2-pyridyl) | | | |
| a1 | r6 | 2,3,4,5,6-F$_5$ | a23 | r6 | 4-O-(2-pyridyl) | | | |
| a2 | r6 | 2,3,4,5,6-F$_5$ | a25 | r6 | 4-O-(2-pyridyl) | | | |
| a4 | r6 | 2,3,4,5,6-F$_5$ | a26 | r6 | 4-O-(2-pyridyl) | | | |
| a23 | r6 | 2,3,4,5,6-F$_5$ | a35 | r6 | 4-O-(2-pyridyl) | | | |
| a25 | r6 | 2,3,4,5,6-F$_5$ | a1 | r6 | 4-O-(3-Cl-5-CF$_3$-pyridine-2-yl)- | | | |
| a26 | r6 | 2,3,4,5,6-F$_5$ | a2 | r6 | 4-O-(3-Cl-5-CF$_3$-pyridine-2-yl)- | | | |
| a35 | r6 | 2,3,4,5,6-F$_5$ | a4 | r6 | 4-O-(3-Cl-5-CF$_3$-pyridine-2-yl)- | | | |
| a1 | r6 | 2,3,4,5,6-Cl$_5$ | a23 | r6 | 4-O-(3-Cl-5-CF$_3$-pyridine-2-yl)- | | | |
| a2 | r6 | 2,3,4,5,6-Cl$_5$ | a25 | r6 | 4-O-(3-Cl-5-CF$_3$-pyridine-2-yl)- | | | |
| a4 | r6 | 2,3,4,5,6-Cl$_5$ | a26 | r6 | 4-O-(3-Cl-5-CF$_3$-pyridine-2-yl)- | | | |
| a23 | r6 | 2,3,4,5,6-Cl$_5$ | a35 | r6 | 4-O-(3-Cl-5-CF$_3$-pyridine-2-yl)- | | | |
| a25 | r6 | 2,3,4,5,6-Cl$_5$ | | | | | | |
| a26 | r6 | 2,3,4,5,6-Cl$_5$ | | | | | | |
| a35 | r6 | 2,3,4,5,6-Cl$_5$ | | | | | | |
| a1 | r6 | 3-NO$_2$ | a7 | r6 | 3-F | a26 | r6 | 3-F |
| a2 | r6 | 3-NO$_2$ | a8 | r6 | 3-F | a25 | r7 | 3-F |
| a4 | r6 | 3-NO$_2$ | a9 | r6 | 3-F | a25 | r8 | 3-F |

TABLE 1-continued

| | | | | | | | | |
|---|---|---|---|---|---|---|---|---|
| a23 | r6 | 3-NO₂ | a10 | r6 | 3-F | a25 | r9 | 3-F |
| a25 | r6 | 3-NO₂ | a11 | r6 | 3-F | a25 | r10 | 3-F |
| a26 | r6 | 3-NO₂ | a12 | r6 | 3-F | a25 | r1 | 3-F |
| a35 | r6 | 3-NO₂ | a13 | r6 | 3-F | a25 | r12 | 3-F |
| a1 | r6 | 3-CN | a14 | r6 | 3-F | a25 | n13 | 3-F |
| a2 | r6 | 3-CN | a15 | r6 | 3-F | a25 | r14 | 3-F |
| a4 | r6 | 3-CN | a16 | r6 | 3-F | a25 | r15 | 3-F |
| a23 | r6 | 3-CN | a17 | r6 | 3-F | a25 | r16 | 3-F |
| a25 | r6 | 3-CN | a18 | r6 | 3-F | a25 | n17 | 3-F |
| a26 | r6 | 3-CN | a19 | r6 | 3-F | a25 | r18 | 3-F |
| a35 | r6 | 3-CN | a20 | r6 | 3-F | a25 | n19 | 3-F |
| a1 | r1 | 3-F | a21 | r6 | 3-F | a25 | r20 | 3-F |
| a1 | r6 | 3-F | a22 | r6 | 3-F | a25 | r21 | 3-F |
| a1 | r22 | 3-F | a23 | r1 | 3-F | a25 | r22 | 3-F |
| a1 | r43 | 3-F | a23 | r6 | 3-F | a25 | r23 | 3-F |
| a1 | r52 | 3-F | a23 | r22 | 3-F | a25 | r24 | 3-F |
| a2 | r1 | 3-F | a23 | r43 | 3-F | a25 | r25 | 3-F |
| a2 | r6 | 3-F | a23 | r52 | 3-F | a25 | r26 | 3-F |
| a2 | r22 | 3-F | a24 | r1 | 3-F | a25 | r27 | 3-F |
| a2 | r43 | 3-F | a24 | r6 | 3-F | a25 | r28 | 3-F |
| a2 | r52 | 3-F | a24 | r22 | 3-F | a25 | r29 | 3-F |
| a3 | r6 | 3-F | a24 | r43 | 3-F | a25 | r30 | 3-F |
| a3 | r22 | 3-F | a24 | r52 | 3-F | a25 | r31 | 3-F |
| a4 | r6 | 3-F | a25 | r1 | 3-F | a25 | r32 | 3-F |
| a4 | r22 | 3-F | a25 | r2 | 3-F | a25 | r33 | 3-F |
| a5 | r6 | 3-F | a25 | r3 | 3-F | a25 | r34 | 3-F |
| a5 | r22 | 3-F | a25 | r4 | 3-F | a25 | r35 | 3-F |
| a6 | r6 | 3-F | a25 | r5 | 3-F | a25 | r36 | 3-F |
| a25 | r37 | 3-F | a26 | r1 | 3-F | a32 | r6 | 3-F |
| a25 | r38 | 3-F | a26 | r6 | 3-F | a32 | r22 | 3-F |
| a25 | r39 | 3-F | a26 | r22 | 3-F | a32 | r43 | 3-F |
| a25 | r40 | 3-F | a26 | r43 | 3-F | a32 | r52 | 3-F |
| a25 | r41 | 3-F | a26 | r52 | 3-F | a33 | r1 | 3-F |
| a25 | r42 | 3-F | a27 | r1 | 3-F | a33 | r6 | 3-F |
| a25 | r43 | 3-F | a27 | r6 | 3-F | a33 | r22 | 3-F |
| a25 | r44 | 3-F | a27 | r22 | 3-F | a33 | r43 | 3-F |
| a25 | r45 | 3-F | a27 | r43 | 3-F | a33 | r52 | 3-F |
| a25 | r46 | 3-F | a27 | r52 | 3-F | a34 | r1 | 3-F |
| a25 | r47 | 3-F | a28 | r1 | 3-F | a34 | r6 | 3-F |
| a25 | r48 | 3-F | a28 | r6 | 3-F | a34 | r22 | 3-F |
| a25 | r49 | 3-F | a28 | r22 | 3-F | a34 | r43 | 3-F |
| a25 | r50 | 3-F | a28 | r43 | 3-F | a34 | r52 | 3-F |
| a25 | r51 | 3-F | a28 | r52 | 3-F | a35 | r1 | 3-F |
| a25 | r52 | 3-F | a29 | r1 | 3-F | a35 | r6 | 3-F |
| a25 | r53 | 3-F | a29 | r6 | 3-F | a35 | r22 | 3-F |
| a25 | r54 | 3-F | a29 | r22 | 3-F | a35 | r43 | 3-F |
| a25 | r55 | 3-F | a29 | r43 | 3-F | a35 | r52 | 3-F |
| a25 | r56 | 3-F | a29 | r52 | 3-F | a36 | r1 | 3-F |
| a25 | r57 | 3-F | a30 | r1 | 3-F | a36 | r6 | 3-F |
| a25 | r58 | 3-F | a30 | r6 | 3-F | a36 | r22 | 3-F |
| a25 | r59 | 3-F | a30 | r22 | 3-F | a36 | r43 | 3-F |
| a25 | r60 | 3-F | a30 | r43 | 3-F | a36 | r52 | 3-F |
| a25 | r61 | 3-F | a30 | r52 | 3-F | a37 | r6 | 3-F |
| a25 | r62 | 3-F | a31 | r1 | 3-F | a38 | r1 | 3-F |
| a25 | r63 | 3-F | a31 | r6 | 3-F | a38 | r6 | 3-F |
| a25 | r64 | 3-F | a31 | r22 | 3-F | a38 | r22 | 3-F |
| a25 | r65 | 3-F | a31 | r43 | 3-F | a38 | r43 | 3-F |
| a25 | r66 | 3-F | a31 | r52 | 3-F | a38 | r52 | 3-F |
| a25 | r67 | 3-F | a32 | r1 | 3-F | a39 | r1 | 3-F |
| a39 | r6 | 3-F | a1 | r1 | 3-Cl | a23 | r43 | 3-Cl |
| a39 | r22 | 3-F | a1 | r22 | 3-Cl | a23 | r52 | 3-Cl |
| a39 | r43 | 3-F | a1 | r43 | 3-Cl | a24 | r1 | 3-Cl |
| a39 | r52 | 3-F | a1 | r52 | 3-Cl | a24 | r6 | 3-Cl |
| a40 | r1 | 3-F | a2 | r1 | 3-Cl | a24 | r22 | 3-Cl |
| a40 | r6 | 3-F | a2 | r22 | 3-Cl | a24 | r43 | 3-Cl |
| a40 | r22 | 3-F | a2 | r43 | 3-Cl | a24 | r52 | 3-Cl |
| a40 | r43 | 3-F | a2 | r52 | 3-Cl | a25 | r1 | 3-Cl |
| a40 | r52 | 3-F | a3 | r6 | 3-Cl | a25 | r2 | 3-Cl |
| a41 | r1 | 3-F | a3 | r22 | 3-Cl | a25 | r3 | 3-Cl |
| a41 | r6 | 3-F | a4 | r22 | 3-Cl | a25 | r4 | 3-Cl |
| a41 | r22 | 3-F | a5 | r6 | 3-Cl | a25 | r5 | 3-Cl |
| a41 | r43 | 3-F | a5 | r22 | 3-Cl | a25 | r7 | 3-Cl |
| a41 | r52 | 3-F | a6 | r6 | 3-Cl | a25 | r8 | 3-Cl |
| a42 | r6 | 3-F | a7 | r6 | 3-Cl | a25 | r9 | 3-Cl |
| a43 | r6 | 3-F | a8 | r6 | 3-Cl | a25 | r10 | 3-Cl |
| a44 | r6 | 3-F | a9 | r6 | 3-Cl | a25 | r1 | 3-Cl |
| a45 | r6 | 3-F | a10 | r6 | 3-Cl | a25 | n12 | 3-Cl |
| a46 | r6 | 3-F | a11 | r6 | 3-Cl | a25 | r13 | 3-Cl |
| a47 | r6 | 3-F | a12 | r6 | 3-Cl | a25 | n14 | 3-Cl |

TABLE 1-continued

| | | | | | | | | |
|---|---|---|---|---|---|---|---|---|
| a48 | r6 | 3-F | a13 | r6 | 3-Cl | a25 | n15 | 3-Cl |
| a49 | r6 | 3-F | a14 | r6 | 3-Cl | a25 | n16 | 3-Cl |
| a50 | r6 | 3-F | a15 | r6 | 3-Cl | a25 | n17 | 3-Cl |
| a51 | r6 | 3-F | a16 | r6 | 3-Cl | a25 | n18 | 3-Cl |
| a52 | r6 | 3-F | a17 | r6 | 3-Cl | a25 | n19 | 3-Cl |
| a53 | r6 | 3-F | a18 | r6 | 3-Cl | a25 | r20 | 3-Cl |
| a54 | r6 | 3-F | a19 | r6 | 3-Cl | a25 | r21 | 3-Cl |
| a55 | r6 | 3-F | a20 | r6 | 3-Cl | a25 | r22 | 3-Cl |
| a56 | r6 | 3-F | a21 | r6 | 3-Cl | a25 | r23 | 3-Cl |
| a57 | r6 | 3-F | a22 | r6 | 3-Cl | a25 | r24 | 3-Cl |
| a58 | r6 | 3-F | a23 | r1 | 3-Cl | a25 | r25 | 3-Cl |
| a59 | r6 | 3-F | a23 | r22 | 3-Cl | a25 | r26 | 3-Cl |
| a25 | r27 | 3-Cl | a25 | r58 | 3-Cl | a30 | r22 | 3-Cl |
| a25 | r28 | 3-Cl | a25 | r59 | 3-Cl | a30 | r43 | 3-Cl |
| a25 | r29 | 3-Cl | a25 | r60 | 3-Cl | a30 | r52 | 3-Cl |
| a25 | r30 | 3-Cl | a25 | r61 | 3-Cl | a31 | r2 | 3-Cl |
| a25 | r31 | 3-Cl | a25 | r62 | 3-Cl | a31 | r6 | 3-Cl |
| a25 | r32 | 3-Cl | a25 | r63 | 3-Cl | a31 | r22 | 3-Cl |
| a25 | r33 | 3-Cl | a25 | r64 | 3-Cl | a31 | r43 | 3-Cl |
| a25 | r34 | 3-Cl | a25 | r65 | 3-Cl | a31 | r52 | 3-Cl |
| a25 | r35 | 3-Cl | a25 | r66 | 3-Cl | a32 | r1 | 3-Cl |
| a25 | r36 | 3-Cl | a25 | r67 | 3-Cl | a32 | r6 | 3-Cl |
| a25 | r37 | 3-Cl | a26 | r1 | 3-Cl | a32 | r22 | 3-Cl |
| a25 | r38 | 3-Cl | a26 | r22 | 3-Cl | a32 | r43 | 3-Cl |
| a25 | r39 | 3-Cl | a26 | r43 | 3-Cl | a32 | r52 | 3-Cl |
| a25 | r40 | 3-Cl | a26 | r52 | 3-Cl | a33 | r1 | 3-Cl |
| a25 | r41 | 3-Cl | a27 | r1 | 3-Cl | a33 | r6 | 3-Cl |
| a25 | r42 | 3-Cl | a27 | r6 | 3-Cl | a33 | r22 | 3-Cl |
| a25 | r43 | 3-Cl | a27 | r22 | 3-Cl | a33 | r43 | 3-Cl |
| a25 | r44 | 3-Cl | a27 | r43 | 3-Cl | a33 | r62 | 3-Cl |
| a25 | r45 | 3-Cl | a27 | r52 | 3-Cl | a34 | r1 | 3-Cl |
| a25 | r46 | 3-Cl | a28 | r1 | 3-Cl | a34 | r6 | 3-Cl |
| a25 | r47 | 3-Cl | a28 | r6 | 3-Cl | a34 | r22 | 3-Cl |
| a25 | r48 | 3-Cl | a28 | r22 | 3-Cl | a34 | r43 | 3-Cl |
| a26 | r49 | 3-Cl | a28 | r43 | 3-Cl | a34 | r52 | 3-Cl |
| a25 | r50 | 3-Cl | a28 | r52 | 3-Cl | a35 | r1 | 3-Cl |
| a25 | r51 | 3-Cl | a29 | r1 | 3-Cl | a35 | r22 | 3-Cl |
| a25 | r52 | 3-Cl | a29 | r6 | 3-Cl | a35 | r43 | 3-Cl |
| a25 | r53 | 3-Cl | a29 | r22 | 3-Cl | a35 | r52 | 3-Cl |
| a25 | r54 | 3-Cl | a29 | r43 | 3-Cl | a36 | r1 | 3-Cl |
| a25 | r55 | 3-Cl | a29 | r52 | 3-Cl | a36 | r6 | 3-Cl |
| a25 | r56 | 3-Cl | a30 | r1 | 3-Cl | a36 | r22 | 3-Cl |
| a25 | r57 | 3-Cl | a30 | r6 | 3-Cl | a36 | r43 | 3-Cl |
| a36 | r52 | 3-Cl | a52 | r6 | 3-Cl | a23 | r6 | 3-iPr |
| a37 | r6 | 3-Cl | a53 | r6 | 3-Cl | a25 | r6 | 3-iPr |
| a38 | r1 | 3-Cl | a54 | r6 | 3-Cl | a26 | r6 | 3-iPr |
| a38 | r6 | 3-Cl | a55 | r6 | 3-Cl | a35 | r6 | 3-iPr |
| a38 | r22 | 3-Cl | a56 | r6 | 3-Cl | a1 | r6 | 3-tBu |
| a38 | r43 | 3-Cl | a57 | r6 | 3-Cl | a2 | r6 | 3-tBu |
| a38 | r52 | 3-Cl | a58 | r6 | 3-Cl | a4 | r6 | 3-tBu |
| a39 | r1 | 3-Cl | a59 | r6 | 3-Cl | a23 | r6 | 3-tBu |
| a39 | r6 | 3-Cl | a1 | r6 | 3-Br | a25 | r6 | 3-tBu |
| a39 | r22 | 3-Cl | a2 | r6 | 3-Br | a26 | r6 | 3-tBu |
| a39 | r43 | 3-Cl | a4 | r6 | 3-Br | a35 | r6 | 3-tBu |
| a39 | r52 | 3-Cl | a23 | r6 | 3-Br | a1 | r6 | 3-nHex |
| a40 | r1 | 3-Cl | a25 | r6 | 3-Br | a2 | r6 | 3-nHex |
| a40 | r6 | 3-Cl | a26 | r6 | 3-Br | a4 | r6 | 3-nHex |
| a40 | r22 | 3-Cl | a35 | r6 | 3-Br | a23 | r6 | 3-nHex |
| a40 | r43 | 3-Cl | a1 | r6 | 3-I | a25 | r6 | 3-nHex |
| a40 | r52 | 3-Cl | a2 | r6 | 3-I | a26 | r6 | 3-nHex |
| a41 | r1 | 3-Cl | a4 | r6 | 3-I | a35 | r6 | 3-nHex |
| a41 | r6 | 3-Cl | a23 | r6 | 3-I | a1 | r6 | 3-cPr |
| a41 | r22 | 3-Cl | a25 | r6 | 3-I | a2 | r6 | 3-cPr |
| a41 | r43 | 3-Cl | a26 | r6 | 3-I | a4 | r6 | 3-cPr |
| a41 | r52 | 3-Cl | a35 | r6 | 3-I | a23 | r6 | 3-cPr |
| a42 | r6 | 3-Cl | a1 | r6 | 3-Me | a25 | r6 | 3-cPr |
| a43 | r6 | 3-Cl | a2 | r6 | 3-Me | a26 | r6 | 3-cPr |
| a44 | r6 | 3-Cl | a4 | r6 | 3-Me | a35 | r6 | 3-cPr |
| a45 | r6 | 3-Cl | a23 | r6 | 3-Me | a1 | r6 | 3-cHex |
| a46 | r6 | 3-Cl | a25 | r6 | 3-Me | a2 | r6 | 3-cHex |
| a47 | r6 | 3-Cl | a26 | r6 | 3-Me | a4 | r6 | 3-cHex |
| a48 | r6 | 3-Cl | a35 | r6 | 3-Me | a23 | r6 | 3-cHex |
| a49 | r6 | 3-Cl | a1 | r6 | 3-iPr | a25 | r6 | 3-cHex |
| a50 | r6 | 3-Cl | a2 | r6 | 3-iPr | a26 | r6 | 3-cHex |
| a51 | r6 | 3-Cl | a4 | r6 | 3-iPr | a35 | r6 | 3-cHex |
| a1 | r1 | 3-$CF_3$ | a21 | r6 | 3-$CF_3$ | a25 | r20 | 3-$CF_3$ |
| a1 | r6 | 3-$CF_3$ | a22 | r6 | 3-$CF_3$ | a25 | r21 | 3-$CF_3$ |
| a1 | r22 | 3-$CF_3$ | a23 | r1 | 3-$CF_3$ | a25 | r22 | 3-$CF_3$ |
| a1 | r43 | 3-$CF_3$ | a23 | r6 | 3-$CF_3$ | a25 | r23 | 3-$CF_3$ |

TABLE 1-continued

| | | | | | | | | |
|---|---|---|---|---|---|---|---|---|
| a1 | r52 | 3-CF₃ | a23 | r22 | 3-CF₃ | a25 | r24 | 3-CF₃ |
| a2 | r1 | 3-CF₃ | a23 | r43 | 3-CF₃ | a25 | r25 | 3-CF₃ |
| a2 | r6 | 3-CF₃ | a23 | r52 | 3-CF₃ | a25 | r26 | 3-CF₃ |
| a2 | r22 | 3-CF₃ | a24 | r1 | 3-CF₃ | a25 | r27 | 3-CF₃ |
| a2 | r43 | 3-CF₃ | a24 | r6 | 3-CF₃ | a25 | r28 | 3-CF₃ |
| a2 | r52 | 3-CF₃ | a24 | r22 | 3-CF₃ | a25 | r29 | 3-CF₃ |
| a3 | r6 | 3-CF₃ | a24 | r43 | 3-CF₃ | a25 | r30 | 3-CF₃ |
| a3 | r22 | 3-CF₃ | a24 | r52 | 3-CF₃ | a25 | r31 | 3-CF₃ |
| a4 | r6 | 3-CF₃ | a25 | r1 | 3-CF₃ | a25 | r32 | 3-CF₃ |
| a4 | r22 | 3-CF₃ | a25 | r2 | 3-CF₃ | a25 | r33 | 3-CF₃ |
| a5 | r6 | 3-CF₃ | a25 | r3 | 3-CF₃ | a25 | r34 | 3-CF₃ |
| a6 | r22 | 3-CF₃ | a25 | r4 | 3-CF₃ | a25 | r35 | 3-CF₃ |
| a6 | r6 | 3-CF₃ | a25 | r5 | 3-CF₃ | a25 | r36 | 3-CF₃ |
| a7 | r6 | 3-CF₃ | a25 | r6 | 3-CF₃ | a25 | r37 | 3-CF₃ |
| a8 | r6 | 3-CF₃ | a25 | r7 | 3-CF₃ | a25 | r38 | 3-CF₃ |
| a9 | r6 | 3-CF₃ | a25 | r8 | 3-CF₃ | a25 | r39 | 3-CF₃ |
| a10 | r6 | 3-CF₃ | a25 | r9 | 3-CF₃ | a25 | r40 | 3-CF₃ |
| a11 | r6 | 3-CF₃ | a25 | r10 | 3-CF₃ | a25 | r41 | 3-CF₃ |
| a12 | r6 | 3-CF₃ | a25 | r11 | 3-CF₃ | a25 | r42 | 3-CF₃ |
| a13 | r6 | 3-CF₃ | a25 | r12 | 3-CF₃ | a25 | r43 | 3-CF₃ |
| a14 | r6 | 3-CF₃ | a25 | r13 | 3-CF₃ | a25 | r44 | 3-CF₃ |
| a15 | r6 | 3-CF₃ | a25 | r14 | 3-CF₃ | a25 | r45 | 3-CF₃ |
| a16 | r6 | 3-CF₃ | a25 | r15 | 3-CF₃ | a25 | r46 | 3-CF₃ |
| a17 | r6 | 3-CF₃ | a25 | r16 | 3-CF₃ | a25 | r47 | 3-CF₃ |
| a18 | r6 | 3-CF₃ | a25 | r17 | 3-CF₃ | a25 | r48 | 3-CF₃ |
| a19 | r6 | 3-CF₃ | a25 | r18 | 3-CF₃ | a25 | r49 | 3-CF₃ |
| a20 | r6 | 3-CF₃ | a25 | r19 | 3-CF₃ | a25 | r50 | 3-CF₃ |
| a25 | r51 | 3-CF₃ | a29 | r1 | 3-CF₃ | a35 | r22 | 3-CF₃ |
| a25 | r52 | 3-CF₃ | a29 | r6 | 3-CF₃ | a36 | r43 | 3-CF₃ |
| a25 | r53 | 3-CF₃ | a29 | r22 | 3-CF₃ | a35 | r52 | 3-CF₃ |
| a25 | r54 | 3-CF₃ | a29 | r43 | 3-CF₃ | a36 | r1 | 3-CF₃ |
| a25 | r55 | 3-CF₃ | a29 | r52 | 3-CF₃ | a36 | r6 | 3-CF₃ |
| a25 | r56 | 3-CF₃ | a30 | r1 | 3-CF₃ | a36 | r22 | 3-CF₃ |
| a25 | r57 | 3-CF₃ | a30 | r6 | 3-CF₃ | a36 | r43 | 3-CF₃ |
| a25 | r58 | 3-CF₃ | a30 | r22 | 3-CF₃ | a36 | r52 | 3-CF₃ |
| a25 | r59 | 3-CF₃ | a30 | r43 | 3-CF₃ | a37 | r6 | 3-CF₃ |
| a25 | r60 | 3-CF₃ | a30 | r52 | 3-CF₃ | a38 | r1 | 3-CF₃ |
| a25 | r61 | 3-CF₃ | a31 | r1 | 3-CF₃ | a38 | r6 | 3-CF₃ |
| a25 | r62 | 3-CF₃ | a31 | r6 | 3-CF₃ | a38 | r22 | 3-CF₃ |
| a25 | r63 | 3-CF₃ | a31 | r22 | 3-CF₃ | a38 | r43 | 3-CF₃ |
| a25 | r64 | 3-CF₃ | a31 | r43 | 3-CF₃ | a38 | r52 | 3-CF₃ |
| a25 | r65 | 3-CF₃ | a31 | r52 | 3-CF₃ | a39 | r1 | 3-CF₃ |
| a25 | r66 | 3-CF₃ | a32 | r1 | 3-CF₃ | a39 | r6 | 3-CF₃ |
| a25 | r67 | 3-CF₃ | a32 | r6 | 3-CF₃ | a39 | r22 | 3-CF₃ |
| a26 | r1 | 3-CF₃ | a32 | r22 | 3-CF₃ | a39 | r43 | 3-CF₃ |
| a26 | r6 | 3-CF₃ | a32 | r43 | 3-CF₃ | a39 | r52 | 3-CF₃ |
| a26 | r22 | 3-CF₃ | a32 | r52 | 3-CF₃ | a40 | r1 | 3-CF₃ |
| a26 | r43 | 3-CF₃ | a33 | r1 | 3-CF₃ | a40 | r6 | 3-CF₃ |
| a26 | r52 | 3-CF₃ | a33 | r6 | 3-CF₃ | a40 | r22 | 3-CF₃ |
| a27 | r1 | 3-CF₃ | a33 | r22 | 3-CF₃ | a40 | r43 | 3-CF₃ |
| a27 | r6 | 3-CF₃ | a33 | r43 | 3-CF₃ | a40 | r52 | 3-CF₃ |
| a27 | r22 | 3-CF₃ | a33 | r52 | 3-CF₃ | a41 | r1 | 3-CF₃ |
| a27 | r43 | 3-CF₃ | a34 | r1 | 3-CF₃ | a41 | r6 | 3-CF₃ |
| a27 | r52 | 3-CF₃ | a34 | r6 | 3-CF₃ | a41 | r22 | 3-CF₃ |
| a28 | r1 | 3-CF₃ | a34 | r22 | 3-CF₃ | a41 | r43 | 3-CF₃ |
| a28 | r6 | 3-CF₃ | a34 | r43 | 3-CF₃ | a41 | r52 | 3-CF₃ |
| a28 | r22 | 3-CF₃ | a34 | r52 | 3-CF₃ | a42 | r6 | 3-CF₃ |
| a28 | r43 | 3-CF₃ | a35 | r1 | 3-CF₃ | a43 | r6 | 3-CF₃ |
| a28 | r52 | 4-CF₃ | a35 | r6 | 4-CF₃ | a44 | r6 | 4-CF₃ |
| a45 | r6 | 3-CF₃ | a23 | r6 | 3-OtBu | a35 | r6 | 3-CO₂Me |
| a46 | r6 | 3-CF₃ | a25 | r6 | 3-OtBu | a25 | r6 | 3-CO₂tBu |
| a47 | r6 | 3-CF₃ | a26 | r6 | 3-OtBu | a35 | r6 | 3-CO₂tBu |
| a48 | r6 | 3-CF₃ | a35 | r6 | 3-OtBu | a25 | r6 | 3-CH₂Ph |
| a49 | r6 | 3-CF₃ | a1 | r6 | 3-OCF₃ | a35 | r6 | 3-CH₂Ph |
| a50 | r6 | 3-CF₃ | a2 | r6 | 3-OCF₃ | a25 | r6 | 3-OCH₂Ph |
| a51 | r6 | 3-CF₃ | a4 | r6 | 3-OCF₃ | a35 | r6 | 3-OCH₂Ph |
| a52 | r6 | 3-CF₃ | a23 | r6 | 3-OCF₃ | a25 | r6 | 3-(2-thienyl) |
| a53 | r6 | 3-CF₃ | a25 | r6 | 3-OCF₃ | a35 | r6 | 3-(2-thienyl) |
| a54 | r6 | 3-CF₃ | a26 | r6 | 3-OCF₃ | a25 | r6 | 3-(3-thienyl) |
| a55 | r6 | 3-CF₃ | a35 | r6 | 3-OCF₃ | a35 | r6 | 3-(3-thienyl) |
| a56 | r6 | 3-CF₃ | a25 | r6 | 3-Sine | a25 | r6 | 3-(2-pyridyl) |
| a57 | r6 | 3-CF₃ | a35 | r6 | 3-Sine | a35 | r6 | 3-(2-pyridyl) |
| a58 | r6 | 3-CF₃ | a25 | r6 | 3-SOMe | a25 | r6 | 3-(3-pyridyl) |
| a59 | r6 | 3-CF₃ | a35 | r6 | 3-SOMe | a35 | r6 | 3-(3-pyridyl) |
| a1 | r6 | 3-OMe | a25 | r6 | 3-SO₂Me | a25 | r6 | 3-(4-pyridyl) |
| a2 | r6 | 3-OMe | a35 | r6 | 3-SO₂Me | a35 | r6 | 3-(4-pyridyl) |
| a4 | r6 | 3-OMe | a25 | r6 | 3-NHMe | a25 | r6 | 3-Ph |
| a23 | r6 | 3-OMe | a35 | r6 | 3-NHMe | a35 | r6 | 3-Ph |
| a25 | r6 | 3-OMe | a25 | r6 | 3-NMe₂ | a25 | r6 | 3-(4-Cl—Ph) |

TABLE 1-continued

| | | | | | | | | |
|---|---|---|---|---|---|---|---|---|
| a26 | r6 | 3-OMe | a35 | r6 | 3-NMe$_2$ | a35 | r6 | 3-(4-Cl—Ph) |
| a35 | r6 | 3-OMe | a25 | r6 | 3-SiMe$_4$ | a25 | r6 | 3-(4-F—Ph) |
| a1 | r6 | 3-OiPr | a35 | r6 | 3-SiMe$_4$ | a35 | r6 | 3-(4-F—Ph) |
| a2 | r6 | 3-OiPr | a25 | r6 | 3-CH$_2$OEt | a25 | r6 | 3-OPh |
| a4 | r6 | 3-OiPr | a35 | r6 | 3-CH$_2$OEt | a35 | r6 | 3-OPh |
| a23 | r6 | 3-OiPr | a25 | r6 | 3-CH$_2$Set | a1 | r1 | 3,5-Cl$_2$ |
| a25 | r6 | 3-OiPr | a35 | r6 | 3-CH$_2$Set | a1 | r6 | 3,5-Cl$_2$ |
| a26 | r6 | 3-OiPr | a25 | r6 | 3-COMe | a1 | r22 | 3,5-Cl$_2$ |
| a35 | r6 | 3-OiPr | a35 | r6 | 3-COMe | a1 | r43 | 3,5-Cl$_2$ |
| a1 | r6 | 3-OtBu | a25 | r6 | 3-CotBu | a1 | r52 | 3,5-Cl$_2$ |
| a2 | r6 | 3-OtBu | a35 | r6 | 3-CotBu | a2 | r1 | 3,5-Cl$_2$ |
| a4 | r6 | 3-OtBu | a25 | r6 | 3-CO$_2$Me | a2 | r6 | 3,5-Cl$_2$ |
| a2 | r22 | 3,5-Cl$_2$ | a24 | r1 | 3,5-Cl$_2$ | a25 | r27 | 3,5-Cl$_2$ |
| a2 | r43 | 3,5-Cl$_2$ | a24 | r6 | 3,5-Cl$_2$ | a25 | r28 | 3,5-Cl$_2$ |
| a2 | r52 | 3,5-Cl$_2$ | a24 | r22 | 3,5-Cl$_2$ | a25 | r29 | 3,5-Cl$_2$ |
| a3 | r6 | 3,5-Cl$_2$ | a24 | r43 | 3,5-Cl$_2$ | a25 | r30 | 3,5-Cl$_2$ |
| a3 | r22 | 3,5-Cl$_2$ | a24 | r52 | 3,5-Cl$_2$ | a25 | r31 | 3,5-Cl$_2$ |
| a4 | r6 | 3,5-Cl$_2$ | a25 | r1 | 3,5-Cl$_2$ | a25 | r32 | 3,5-Cl$_2$ |
| a4 | r22 | 3,5-Cl$_2$ | a25 | r2 | 3,5-Cl$_2$ | a25 | r33 | 3,5-Cl$_2$ |
| a5 | r6 | 3,5-Cl$_2$ | a25 | r3 | 3,5-Cl$_2$ | a25 | r34 | 3,5-Cl$_2$ |
| a6 | r22 | 3,5-Cl$_2$ | a25 | r4 | 3,5-Cl$_2$ | a25 | r35 | 3,5-Cl$_2$ |
| a6 | r6 | 3,5-Cl$_2$ | a25 | r5 | 3,5-Cl$_2$ | a25 | r36 | 3,5-Cl$_2$ |
| a7 | r6 | 3,5-Cl$_2$ | a25 | r6 | 3,5-Cl$_2$ | a25 | r37 | 3,5-Cl$_2$ |
| a8 | r6 | 3,5-Cl$_2$ | a25 | r7 | 3,5-Cl$_2$ | a25 | r38 | 3,5-Cl$_2$ |
| a9 | r6 | 3,5-Cl$_2$ | a25 | r8 | 3,5-Cl$_2$ | a25 | r39 | 3,5-Cl$_2$ |
| a10 | r6 | 3,5-Cl$_2$ | a25 | r9 | 3,5-Cl$_2$ | a25 | r40 | 3,5-Cl$_2$ |
| a11 | r6 | 3,5-Cl$_2$ | a25 | r10 | 3,5-Cl$_2$ | a25 | r41 | 3,5-Cl$_2$ |
| a12 | r6 | 3,5-Cl$_2$ | a25 | r1 | 3,5-Cl$_2$ | a25 | r42 | 3,5-Cl$_2$ |
| a13 | r6 | 3,5-Cl$_2$ | a25 | r12 | 3,5-Cl$_2$ | a25 | r43 | 3,5-Cl$_2$ |
| a14 | r6 | 3,5-Cl$_2$ | a25 | r13 | 3,5-Cl$_2$ | a25 | r44 | 3,5-Cl$_2$ |
| a15 | r6 | 3,5-Cl$_2$ | a25 | r14 | 3,5-Cl$_2$ | a25 | r45 | 3,5-Cl$_2$ |
| a16 | r6 | 3,5-Cl$_2$ | a25 | r15 | 3,5-Cl$_2$ | a25 | r46 | 3,5-Cl$_2$ |
| a17 | r6 | 3,5-Cl$_2$ | a25 | r16 | 3,5-Cl$_2$ | a25 | r47 | 3,5-Cl$_2$ |
| a18 | r6 | 3,5-Cl$_2$ | a25 | r17 | 3,5-Cl$_2$ | a25 | r48 | 3,5-Cl$_2$ |
| a19 | r6 | 3,5-Cl$_2$ | a25 | r18 | 3,5-Cl$_2$ | a25 | r49 | 3,5-Cl$_2$ |
| a20 | r6 | 3,5-Cl$_2$ | a25 | r19 | 3,5-Cl$_2$ | a25 | r50 | 3,5-Cl$_2$ |
| a21 | r6 | 3,5-Cl$_2$ | a25 | r20 | 3,5-Cl$_2$ | a25 | r51 | 3,5-Cl$_2$ |
| a22 | r6 | 3,5-Cl$_2$ | a25 | r21 | 3,5-Cl$_2$ | a25 | r52 | 3,5-Cl$_2$ |
| a23 | r1 | 3,5-Cl$_2$ | a25 | r22 | 3,5-Cl$_2$ | a25 | r53 | 3,5-Cl$_2$ |
| a23 | r6 | 3,5-Cl$_2$ | a25 | r23 | 3,5-Cl$_2$ | a25 | r54 | 3,5-Cl$_2$ |
| a23 | r22 | 3,5-Cl$_2$ | a25 | r24 | 3,5-Cl$_2$ | a25 | r55 | 3,5-Cl$_2$ |
| a23 | r43 | 3,5-Cl$_2$ | a25 | r25 | 3,5-Cl$_2$ | a25 | r56 | 3,5-Cl$_2$ |
| a23 | r52 | 3,5-Cl$_2$ | a25 | r26 | 3,5-Cl$_2$ | a25 | r57 | 3,5-Cl$_2$ |
| a25 | r58 | 3,5-Cl$_2$ | a30 | r22 | 3,5-Cl$_2$ | a36 | r52 | 3,5-Cl$_2$ |
| a25 | r59 | 3,5-Cl$_2$ | a30 | r43 | 3,5-Cl$_2$ | a37 | r6 | 3,5-Cl$_2$ |
| a25 | r60 | 3,5-Cl$_2$ | a30 | r52 | 3,5-Cl$_2$ | a38 | r1 | 3,5-Cl$_2$ |
| a25 | r61 | 3,5-Cl$_2$ | a31 | r1 | 3,5-Cl$_2$ | a38 | r6 | 3,5-Cl$_2$ |
| a25 | r62 | 3,5-Cl$_2$ | a31 | r6 | 3,5-Cl$_2$ | a38 | r22 | 3,5-Cl$_2$ |
| a25 | r63 | 3,5-Cl$_2$ | a31 | r22 | 3,5-Cl$_2$ | a38 | r43 | 3,5-Cl$_2$ |
| a25 | r64 | 3,5-Cl$_2$ | a31 | r43 | 3,5-Cl$_2$ | a38 | r52 | 3,5-Cl$_2$ |
| a25 | r65 | 3,5-Cl$_2$ | a31 | r52 | 3,5-Cl$_2$ | a39 | r1 | 3,5-Cl$_2$ |
| a25 | r66 | 3,5-Cl$_2$ | a32 | r1 | 3,5-Cl$_2$ | a39 | r6 | 3,5-Cl$_2$ |
| a25 | r67 | 3,5-Cl$_2$ | a32 | r6 | 3,5-Cl$_2$ | a39 | r22 | 3,5-Cl$_2$ |
| a26 | r1 | 3,5-Cl$_2$ | a32 | r22 | 3,5-Cl$_2$ | a39 | r43 | 3,5-Cl$_2$ |
| a26 | r6 | 3,5-Cl$_2$ | a32 | r43 | 3,5-Cl$_2$ | a39 | r52 | 3,5-Cl$_2$ |
| a26 | r22 | 3,5-Cl$_2$ | a32 | r52 | 3,5-Cl$_2$ | a40 | r1 | 3,5-Cl$_2$ |
| a26 | r43 | 3,5-Cl$_2$ | a33 | r1 | 3,5-Cl$_2$ | a40 | r6 | 3,5-Cl$_2$ |
| a26 | r52 | 3,5-Cl$_2$ | a33 | r6 | 3,5-Cl$_2$ | a40 | r22 | 3,5-Cl$_2$ |
| a27 | r1 | 3,5-Cl$_2$ | a33 | r22 | 3,5-Cl$_2$ | a40 | r43 | 3,5-Cl$_2$ |
| a27 | r6 | 3,5-Cl$_2$ | a33 | r43 | 3,5-Cl$_2$ | a40 | r52 | 3,5-Cl$_2$ |
| a27 | r22 | 3,5-Cl$_2$ | a33 | r52 | 3,5-Cl$_2$ | a41 | r1 | 3,5-Cl$_2$ |
| a27 | r43 | 3,5-Cl$_2$ | a34 | r1 | 3,5-Cl$_2$ | a41 | r6 | 3,5-Cl$_2$ |
| a27 | r52 | 3,5-Cl$_2$ | a34 | r6 | 3,5-Cl$_2$ | a41 | r22 | 3,5-Cl$_2$ |
| a28 | r1 | 3,5-Cl$_2$ | a34 | r22 | 3,5-Cl$_2$ | a41 | r43 | 3,5-Cl$_2$ |
| a28 | r6 | 3,5-Cl$_2$ | a34 | r43 | 3,5-Cl$_2$ | a41 | r52 | 3,5-Cl$_2$ |
| a28 | r22 | 3,5-Cl$_2$ | a34 | r52 | 3,5-Cl$_2$ | a42 | r6 | 3,5-Cl$_2$ |
| a28 | r43 | 3,5-Cl$_2$ | a35 | r1 | 3,5-Cl$_2$ | a43 | r6 | 3,5-Cl$_2$ |
| a28 | r52 | 3,5-Cl$_2$ | a35 | r6 | 3,5-Cl$_2$ | a44 | r6 | 3,5-Cl$_2$ |
| a29 | r1 | 3,5-Cl$_2$ | a35 | r22 | 3,5-Cl$_2$ | a45 | r6 | 3,5-Cl$_2$ |
| a29 | r6 | 3,5-Cl$_2$ | a35 | r43 | 3,5-Cl$_2$ | a46 | r6 | 3,5-Cl$_2$ |
| a29 | r22 | 3,5-Cl$_2$ | a35 | r52 | 3,5-Cl$_2$ | a47 | r6 | 3,5-Cl$_2$ |
| a29 | r43 | 3,5-Cl$_2$ | a36 | r1 | 3,5-Cl$_2$ | a48 | r6 | 3,5-Cl$_2$ |
| a29 | r52 | 3,5-Cl$_2$ | a36 | r6 | 3,5-Cl$_2$ | a49 | r6 | 3,5-Cl$_2$ |
| a30 | r1 | 3,5-Cl$_2$ | a36 | r22 | 3,5-Cl$_2$ | a50 | r6 | 3,5-Cl$_2$ |
| a52 | r6 | 3,5-Cl$_2$ | a14 | r6 | 3,5-F$_2$ | a25 | r14 | 3,5-F$_2$ |
| a53 | r6 | 3,5-Cl$_2$ | a15 | r6 | 3,5-F$_2$ | a25 | r15 | 3,5-F$_2$ |
| a54 | r6 | 3,5-Cl$_2$ | a16 | r6 | 3,5-F$_2$ | a25 | r16 | 3,5-F$_2$ |
| a55 | r6 | 3,5-Cl$_2$ | a17 | r6 | 3,5-F$_2$ | a25 | r17 | 3,5-F$_2$ |
| a56 | r6 | 3,5-Cl$_2$ | a18 | r6 | 3,5-F$_2$ | a25 | r18 | 3,5-F$_2$ |

TABLE 1-continued

| | | | | | | | | |
|---|---|---|---|---|---|---|---|---|
| a57 | r6 | 3,5-Cl$_2$ | a19 | r6 | 3,5-F$_2$ | a25 | r19 | 3,5-F$_2$ |
| a58 | r6 | 3,5-Cl$_2$ | a20 | r6 | 3,5-F$_2$ | a25 | r20 | 3,5-F$_2$ |
| a59 | r6 | 3,5-Cl$_2$ | a21 | r6 | 3,5-F$_2$ | a25 | r21 | 3,5-F$_2$ |
| a1 | r1 | 3,5-F$_2$ | a22 | r6 | 3,5-F$_2$ | a25 | r22 | 3,5-F$_2$ |
| a1 | r6 | 3,5-F$_2$ | a23 | r1 | 3,5-F$_2$ | a25 | r23 | 3,5-F$_2$ |
| a1 | r22 | 3,5-F$_2$ | a23 | r6 | 3,5-F$_2$ | a25 | r24 | 3,5-F$_2$ |
| a1 | r43 | 3,5-F$_2$ | a23 | r22 | 3,5-F$_2$ | a25 | r25 | 3,5-F$_2$ |
| a1 | r52 | 3,5-F$_2$ | a23 | r43 | 3,5-F$_2$ | a25 | r26 | 3,5-F$_2$ |
| a2 | r1 | 3,5-F$_2$ | a23 | r52 | 3,5-F$_2$ | a25 | r27 | 3,5-F$_2$ |
| a2 | r6 | 3,5-F$_2$ | a24 | r1 | 3,5-F$_2$ | a25 | r28 | 3,5-F$_2$ |
| a2 | r22 | 3,5-F$_2$ | a24 | r6 | 3,5-F$_2$ | a25 | r29 | 3,5-F$_2$ |
| a2 | r43 | 3,5-F$_2$ | a24 | r22 | 3,5-F$_2$ | a25 | r30 | 3,5-F$_2$ |
| a2 | r52 | 3,5-F$_2$ | a24 | r43 | 3,5-F$_2$ | a25 | r31 | 3,5-F$_2$ |
| a3 | r6 | 3,5-F$_2$ | a24 | r52 | 3,5-F$_2$ | a25 | r32 | 3,5-F$_2$ |
| a3 | r22 | 3,5-F$_2$ | a25 | r1 | 3,5-F$_2$ | a25 | r33 | 3,5-F$_2$ |
| a4 | r6 | 3,5-F$_2$ | a25 | r2 | 3,5-F$_2$ | a25 | r34 | 3,5-F$_2$ |
| a4 | r22 | 3,5-F$_2$ | a25 | r3 | 3,5-F$_2$ | a25 | r35 | 3,5-F$_2$ |
| a5 | r6 | 3,5-F$_2$ | a25 | r4 | 3,5-F$_2$ | a25 | r36 | 3,5-F$_2$ |
| a5 | r22 | 3,5-F$_2$ | a25 | r5 | 3,5-F$_2$ | a25 | r37 | 3,5-F$_2$ |
| a6 | r6 | 3,5-F$_2$ | a25 | r6 | 3,5-F$_2$ | a25 | r38 | 3,5-F$_2$ |
| a7 | r6 | 3,5-F$_2$ | a25 | r7 | 3,5-F$_2$ | a25 | r39 | 3,5-F$_2$ |
| a8 | r6 | 3,5-F$_2$ | a25 | r8 | 3,5-F$_2$ | a25 | r40 | 3,5-F$_2$ |
| a9 | r6 | 3,5-F$_2$ | a25 | r9 | 3,5-F$_2$ | a25 | r41 | 3,5-F$_2$ |
| a10 | r6 | 3,5-F$_2$ | a25 | r10 | 3,5-F$_2$ | a25 | r42 | 3,5-F$_2$ |
| a11 | r6 | 3,5-F$_2$ | a25 | r1 | 3,5-F$_2$ | a25 | r43 | 3,5-F$_2$ |
| a12 | r6 | 3,5-F$_2$ | a25 | r12 | 3,5-F$_2$ | a25 | r44 | 3,5-F$_2$ |
| a13 | r6 | 3,5-F$_2$ | a25 | r13 | 3,5-F$_2$ | a25 | r45 | 3,5-F$_2$ |
| a25 | r46 | 3,5-F$_2$ | a28 | r1 | 3,5-F$_2$ | a34 | r22 | 3,5-F$_2$ |
| a25 | r47 | 3,5-F$_2$ | a28 | r6 | 3,5-F$_2$ | a34 | r43 | 3,5-F$_2$ |
| a25 | r48 | 3,5-F$_2$ | a28 | r22 | 3,5-F$_2$ | a34 | r52 | 3,5-F$_2$ |
| a25 | r49 | 3,5-F$_2$ | a28 | r43 | 3,5-F$_2$ | a35 | r1 | 3,5-F$_2$ |
| a25 | r50 | 3,5-F$_2$ | a28 | r52 | 3,5-F$_2$ | a35 | r6 | 3,5-F$_2$ |
| a25 | r51 | 3,5-F$_2$ | a29 | r1 | 3,5-F$_2$ | a35 | r22 | 3,5-F$_2$ |
| a25 | r52 | 3,5-F$_2$ | a29 | r6 | 3,5-F$_2$ | a35 | r43 | 3,5-F$_2$ |
| a25 | r53 | 3,5-F$_2$ | a29 | r22 | 3,5-F$_2$ | a35 | r52 | 3,5-F$_2$ |
| a25 | r54 | 3,5-F$_2$ | a29 | r43 | 3,5-F$_2$ | a36 | r1 | 3,5-F$_2$ |
| a25 | r55 | 3,5-F$_2$ | a29 | r52 | 3,5-F$_2$ | a36 | r6 | 3,5-F$_2$ |
| a25 | r56 | 3,5-F$_2$ | a30 | r1 | 3,5-F$_2$ | a36 | r22 | 3,5-F$_2$ |
| a25 | r57 | 3,5-F$_2$ | a30 | r6 | 3,5-F$_2$ | a36 | r43 | 3,5-F$_2$ |
| a25 | r58 | 3,5-F$_2$ | a30 | r22 | 3,5-F$_2$ | a36 | r52 | 3,5-F$_2$ |
| a25 | r59 | 3,5-F$_2$ | a30 | r43 | 3,5-F$_2$ | a37 | r6 | 3,5-F$_2$ |
| a25 | r60 | 3,5-F$_2$ | a30 | r52 | 3,5-F$_2$ | a38 | r1 | 3,5-F$_2$ |
| a25 | r61 | 3,5-F$_2$ | a31 | r1 | 3,5-F$_2$ | a38 | r6 | 3,5-F$_2$ |
| a25 | r62 | 3,5-F$_2$ | a31 | r6 | 3,5-F$_2$ | a38 | r22 | 3,5-F$_2$ |
| a25 | r63 | 3,5-F$_2$ | a31 | r22 | 3,5-F$_2$ | a38 | r43 | 3,5-F$_2$ |
| a25 | r64 | 3,5-F$_2$ | a31 | r43 | 3,5-F$_2$ | a38 | r52 | 3,5-F$_2$ |
| a25 | r65 | 3,5-F$_2$ | a31 | r52 | 3,5-F$_2$ | a39 | r1 | 3,5-F$_2$ |
| a25 | r66 | 3,5-F$_2$ | a32 | r1 | 3,5-F$_2$ | a39 | r6 | 3,5-F$_2$ |
| a25 | r67 | 3,5-F$_2$ | a32 | r6 | 3,5-F$_2$ | a39 | r22 | 3,5-F$_2$ |
| a26 | r1 | 3,5-F$_2$ | a32 | r22 | 3,5-F$_2$ | a39 | r43 | 3,5-F$_2$ |
| a26 | r6 | 3,5-F$_2$ | a32 | r43 | 3,5-F$_2$ | a39 | r52 | 3,5-F$_2$ |
| a26 | r22 | 3,5-F$_2$ | a32 | r52 | 3,5-F$_2$ | a40 | r1 | 3,5-F$_2$ |
| a26 | r43 | 3,5-F$_2$ | a33 | r1 | 3,5-F$_2$ | a40 | r6 | 3,5-F$_2$ |
| a26 | r52 | 3,5-F$_2$ | a33 | r6 | 3,5-F$_2$ | a40 | r22 | 3,5-F$_2$ |
| a27 | r1 | 3,5-F$_2$ | a33 | r22 | 3,5-F$_2$ | a40 | r43 | 3,5-F$_2$ |
| a27 | r6 | 3,5-F$_2$ | a33 | r43 | 3,5-F$_2$ | a40 | r52 | 3,5-F$_2$ |
| a27 | r22 | 3,5-F$_2$ | a33 | r52 | 3,5-F$_2$ | a41 | r1 | 3,5-F$_2$ |
| a27 | r43 | 3,5-F$_2$ | a34 | r1 | 3,5-F$_2$ | a41 | r6 | 3,5-F$_2$ |
| a27 | r52 | 3,5-F$_2$ | a34 | r6 | 3,5-F$_2$ | a41 | r22 | 3,5-F$_2$ |
| a41 | r43 | 3,5-F$_2$ | a4 | r6 | 3,5-Me$_2$ | a25 | r2 | 3,5-Me$_2$ |
| a41 | r52 | 3,5-F$_2$ | a4 | r22 | 3,5-Me$_2$ | a25 | r3 | 3,5-Me$_2$ |
| a42 | r6 | 3,5-F$_2$ | a5 | r6 | 3,5-Me$_2$ | a25 | r4 | 3,5-Me$_2$ |
| a43 | r6 | 3,5-F$_2$ | a5 | r22 | 3,5-Me$_2$ | a25 | r5 | 3,5-Me$_2$ |
| a44 | r6 | 3,5-F$_2$ | a6 | r6 | 3,5-Me$_2$ | a25 | r6 | 3,5-Me$_2$ |
| a45 | r6 | 3,5-F$_2$ | a7 | r6 | 3,5-Me$_2$ | a25 | r7 | 3,5-Me$_2$ |
| a46 | r6 | 3,5-F$_2$ | a8 | r6 | 3,5-Me$_2$ | a25 | r8 | 3,5-Me$_2$ |
| a47 | r6 | 3,5-F$_2$ | a9 | r6 | 3,5-Me$_2$ | a25 | r9 | 3,5-Me$_2$ |
| a48 | r6 | 3,5-F$_2$ | a10 | r6 | 3,5-Me$_2$ | a25 | r10 | 3,5-Me$_2$ |
| a49 | r6 | 3,5-F$_2$ | a11 | r6 | 3,5-Me$_2$ | a25 | r1 | 3,5-Me$_2$ |
| a50 | r6 | 3,5-F$_2$ | a12 | r6 | 3,5-Me$_2$ | a25 | r12 | 3,5-Me$_2$ |
| a51 | r6 | 3,5-F$_2$ | a13 | r6 | 3,5-Me$_2$ | a25 | r13 | 3,5-Me$_2$ |
| a52 | r6 | 3,5-F$_2$ | a14 | r6 | 3,5-Me$_2$ | a25 | n14 | 3,5-Me$_2$ |
| a53 | r6 | 3,5-F$_2$ | a15 | r6 | 3,5-Me$_2$ | a25 | n15 | 3,5-Me$_2$ |
| a54 | r6 | 3,5-F$_2$ | a16 | r6 | 3,5-Me$_2$ | a25 | r16 | 3,5-Me$_2$ |
| a55 | r6 | 3,5-F$_2$ | a17 | r6 | 3,5-Me$_2$ | a25 | r17 | 3,5-Me$_2$ |
| a56 | r6 | 3,5-F$_2$ | a18 | r6 | 3,5-Me$_2$ | a25 | r18 | 3,5-Me$_2$ |
| a57 | r6 | 3,5-F$_2$ | a19 | r6 | 3,5-Me$_2$ | a25 | r19 | 3,5-Me$_2$ |
| a58 | r6 | 3,5-F$_2$ | a20 | r6 | 3,5-Me$_2$ | a25 | r20 | 3,5-Me$_2$ |
| a59 | r6 | 3,5-F$_2$ | a21 | r6 | 3,5-Me$_2$ | a25 | r21 | 3,5-Me$_2$ |

TABLE 1-continued

| | | | | | | | | |
|---|---|---|---|---|---|---|---|---|
| a1 | r1 | 3,5-Me$_2$ | a22 | r6 | 3,5-Me$_2$ | a25 | r22 | 3,5-Me$_2$ |
| a1 | r6 | 3,5-Me$_2$ | a23 | r1 | 3,5-Me$_2$ | a25 | r23 | 3,5-Me$_2$ |
| a1 | r22 | 3,5-Me$_2$ | a23 | r6 | 3,5-Me$_2$ | a25 | r24 | 3,5-Me$_2$ |
| a1 | r43 | 3,5-Me$_2$ | a23 | r22 | 3,5-Me$_2$ | a25 | r25 | 3,5-Me$_2$ |
| a1 | r52 | 3,5-Me$_2$ | a23 | r43 | 3,5-Me$_2$ | a25 | r26 | 3,5-Me$_2$ |
| a2 | r1 | 3,5-Me$_2$ | a23 | r52 | 3,5-Me$_2$ | a25 | r27 | 3,5-Me$_2$ |
| a2 | r6 | 3,5-Me$_2$ | a24 | r1 | 3,5-Me$_2$ | a25 | r28 | 3,5-Me$_2$ |
| a2 | r22 | 3,5-Me$_2$ | a24 | r6 | 3,5-Me$_2$ | a25 | r29 | 3,5-Me$_2$ |
| a2 | r43 | 3,5-Me$_2$ | a24 | r22 | 3,5-Me$_2$ | a25 | r30 | 3,5-Me$_2$ |
| a2 | r52 | 3,5-Me$_2$ | a24 | r43 | 3,5-Me$_2$ | a25 | r31 | 3,5-Me$_2$ |
| a3 | r6 | 3,5-Me$_2$ | a24 | r52 | 3,5-Me$_2$ | a25 | r32 | 3,5-Me$_2$ |
| a3 | r22 | 3,5-Me$_2$ | a25 | r1 | 3,5-Me$_2$ | a25 | r33 | 3,5-Me$_2$ |
| a25 | r34 | 3,5-Me$_2$ | a25 | r66 | 3,5-Me$_2$ | a32 | r1 | 3,5-Me$_2$ |
| a25 | r35 | 3,5-Me$_2$ | a25 | r67 | 3,5-Me$_2$ | a32 | r6 | 3,5-Me$_2$ |
| a25 | r36 | 3,5-Me$_2$ | a26 | r1 | 3,5-Me$_2$ | a32 | r22 | 3,5-Me$_2$ |
| a25 | r37 | 3,5-Me$_2$ | a26 | r6 | 3,5-Me$_2$ | a32 | r43 | 3,5-Me$_2$ |
| a25 | r38 | 3,5-Me$_2$ | a26 | r22 | 3,5-Me$_2$ | a32 | r52 | 3,5-Me$_2$ |
| a25 | r39 | 3,5-Me$_2$ | a26 | r43 | 3,5-Me$_2$ | a33 | r1 | 3,5-Me$_2$ |
| a25 | r40 | 3,5-Me$_2$ | a26 | r52 | 3,5-Me$_2$ | a33 | r6 | 3,5-Me$_2$ |
| a25 | r41 | 3,5-Me$_2$ | a27 | r1 | 3,5-Me$_2$ | a33 | r22 | 3,5-Me$_2$ |
| a25 | r42 | 3,5-Me$_2$ | a27 | r6 | 3,5-Me$_2$ | a33 | r43 | 3,5-Me$_2$ |
| a25 | r43 | 3,5-Me$_2$ | a27 | r22 | 3,5-Me$_2$ | a33 | r52 | 3,5-Me$_2$ |
| a25 | r44 | 3,5-Me$_2$ | a27 | r43 | 3,5-Me$_2$ | a34 | r1 | 3,5-Me$_2$ |
| a25 | r45 | 3,5-Me$_2$ | a27 | r52 | 3,5-Me$_2$ | a34 | r6 | 3,5-Me$_2$ |
| a25 | r46 | 3,5-Me$_2$ | a28 | r1 | 3,5-Me$_2$ | a34 | r22 | 3,5-Me$_2$ |
| a25 | r47 | 3,5-Me$_2$ | a28 | r6 | 3,5-Me$_2$ | a34 | r43 | 3,5-Me$_2$ |
| a25 | r48 | 3,5-Me$_2$ | a28 | r22 | 3,5-Me$_2$ | a34 | r52 | 3,5-Me$_2$ |
| a25 | r49 | 3,5-Me$_2$ | a28 | r43 | 3,5-Me$_2$ | a35 | r1 | 3,5-Me$_2$ |
| a25 | r50 | 3,5-Me$_2$ | a28 | r52 | 3,5-Me$_2$ | a35 | r6 | 3,5-Me$_2$ |
| a25 | r51 | 3,5-Me$_2$ | a29 | r1 | 3,5-Me$_2$ | a35 | r22 | 3,5-Me$_2$ |
| a25 | r52 | 3,5-Me$_2$ | a29 | r6 | 3,5-Me$_2$ | a35 | r43 | 3,5-Me$_2$ |
| a25 | r53 | 3,5-Me$_2$ | a29 | r22 | 3,5-Me$_2$ | a35 | r52 | 3,5-Me$_2$ |
| a25 | r54 | 3,5-Me$_2$ | a29 | r43 | 3,5-Me$_2$ | a36 | r1 | 3,5-Me$_2$ |
| a25 | r55 | 3,5-Me$_2$ | a29 | r52 | 3,5-Me$_2$ | a36 | r6 | 3,5-Me$_2$ |
| a25 | r56 | 3,5-Me$_2$ | a30 | r1 | 3,5-Me$_2$ | a36 | r22 | 3,5-Me$_2$ |
| a25 | r57 | 3,5-Me$_2$ | a30 | r6 | 3,5-Me$_2$ | a36 | r43 | 3,5-Me$_2$ |
| a25 | r58 | 3,5-Me$_2$ | a30 | r22 | 3,5-Me$_2$ | a36 | r52 | 3,5-Me$_2$ |
| a25 | r59 | 3,5-Me$_2$ | a30 | r43 | 3,5-Me$_2$ | a37 | r6 | 3,5-Me$_2$ |
| a25 | r60 | 3,5-Me$_2$ | a30 | r52 | 3,5-Me$_2$ | a38 | r1 | 3,5-Me$_2$ |
| a25 | r61 | 3,5-Me$_2$ | a31 | r1 | 3,5-Me$_2$ | a38 | r6 | 3,5-Me$_2$ |
| a25 | r62 | 3,5-Me$_2$ | a31 | r6 | 3,5-Me$_2$ | a38 | r22 | 3,5-Me$_2$ |
| a25 | r63 | 3,5-Me$_2$ | a31 | r22 | 3,5-Me$_2$ | a38 | r43 | 3,5-Me$_2$ |
| a25 | r64 | 3,5-Me$_2$ | a31 | r43 | 3,5-Me$_2$ | a38 | r52 | 3,5-Me$_2$ |
| a25 | r65 | 3,5-Me$_2$ | a31 | r52 | 3,5-Me$_2$ | a39 | r1 | 3,5-Me$_2$ |
| a39 | r6 | 3,5-Me$_2$ | a1 | H | a12 | H | 4-F | |
| a39 | r22 | 3,5-Me$_2$ | a2 | H | a13 | H | 4-F | |
| a39 | r43 | 3,5-Me$_2$ | a4 | H | a14 | H | 4-F | |
| a39 | r52 | 3,5-Me$_2$ | a23 | H | a15 | H | 4-F | |
| a40 | r1 | 3,5-Me$_2$ | a25 | H | a16 | H | 4-F | |
| a40 | r6 | 3,5-Me$_2$ | a26 | H | a17 | H | 4-F | |
| a40 | r22 | 3,5-Me$_2$ | a35 | H | a18 | H | 4-F | |
| a40 | r43 | 3,5-Me$_2$ | a1 | H | 4-NO$_2$ | a19 | H | 4-F |
| a40 | r52 | 3,5-Me$_2$ | a2 | H | 4-NO$_2$ | a20 | H | 4-F |
| a41 | r1 | 3,5-Me$_2$ | a4 | H | 4-NO$_2$ | a21 | H | 4-F |
| a41 | r6 | 3,5-Me$_2$ | a23 | H | 4-NO$_2$ | a22 | H | 4-F |
| a41 | r22 | 3,5-Me$_2$ | a25 | H | 4-NO$_2$ | a23 | H | 4-F |
| a41 | r43 | 3,5-Me$_2$ | a26 | H | 4-NO$_2$ | a24 | H | 4-F |
| a41 | r52 | 3,5-Me$_2$ | a35 | H | 4-NO$_2$ | a25 | H | 4-F |
| a42 | r6 | 3,5-Me$_2$ | a1 | H | 4-CN | a26 | H | 4-F |
| a43 | r6 | 3,5-Me$_2$ | a2 | H | 4-CN | a27 | H | 4-F |
| a44 | r6 | 3,5-Me$_2$ | a4 | H | 4-CN | a28 | H | 4-F |
| a45 | r6 | 3,5-Me$_2$ | a23 | H | 4-CN | a29 | H | 4-F |
| a46 | r6 | 3,5-Me$_2$ | a25 | H | 4-CN | a30 | H | 4-F |
| a47 | r6 | 3,5-Me$_2$ | a26 | H | 4-CN | a31 | H | 4-F |
| a48 | r6 | 3,5-Me$_2$ | a35 | H | 4-CN | a32 | H | 4-F |
| a49 | r6 | 3,5-Me$_2$ | a1 | H | 4-F | a33 | H | 4-F |
| a50 | r6 | 3,5-Me$_2$ | a2 | H | 4-F | a34 | H | 4-F |
| a51 | r6 | 3,5-Me$_2$ | a3 | H | 4-F | a35 | H | 4-F |
| a52 | r6 | 3,5-Me$_2$ | a4 | H | 4-F | a36 | H | 4-F |
| a53 | r6 | 3,5-Me$_2$ | a5 | H | 4-F | a37 | H | 4-F |
| a54 | r6 | 3,5-Me$_2$ | a6 | H | 4-F | a38 | H | 4-F |
| a55 | r6 | 3,5-Me$_2$ | a7 | H | 4-F | a39 | H | 4-F |
| a56 | r6 | 3,5-Me$_2$ | a8 | H | 4-F | a40 | H | 4-F |
| a57 | r6 | 3,5-Me$_2$ | a9 | H | 4-F | a41 | H | 4-F |
| a58 | r6 | 3,5-Me$_2$ | a10 | H | 4-F | a42 | H | 4-F |
| a59 | r6 | 3,5-Me$_2$ | a11 | H | 4-F | a43 | H | 4-F |
| a44 | H | 4-F | a16 | H | 4-Cl | a47 | H | 4-Cl |
| a45 | H | 4-F | a17 | H | 4-Cl | a48 | H | 4-Cl |
| a46 | H | 4-F | a18 | H | 4-Cl | a49 | H | 4-Cl |

TABLE 1-continued

| | | | | | | | | |
|---|---|---|---|---|---|---|---|---|
| a47 | H | 4-F | a19 | H | 4-Cl | a50 | H | 4-Cl |
| a48 | H | 4-F | a20 | H | 4-Cl | a51 | H | 4-Cl |
| a49 | H | 4-F | a21 | H | 4-Cl | a52 | H | 4-Cl |
| a50 | H | 4-F | a22 | H | 4-Cl | a53 | H | 4-Cl |
| a51 | H | 4-F | a23 | H | 4-Cl | a54 | H | 4-Cl |
| a52 | H | 4-F | a24 | H | 4-Cl | a55 | H | 4-Cl |
| a53 | H | 4-F | a25 | H | 4-Cl | a56 | H | 4-Cl |
| a54 | H | 4-F | a26 | H | 4-Cl | a57 | H | 4-Cl |
| a55 | H | 4-F | a27 | H | 4-Cl | a58 | H | 4-Cl |
| a56 | H | 4-F | a28 | H | 4-Cl | a59 | H | 4-Cl |
| a57 | H | 4-F | a29 | H | 4-Cl | a1 | H | 4-Br |
| a58 | H | 4-F | a30 | H | 4-Cl | a2 | H | 4-Br |
| a59 | H | 4-F | a31 | H | 4-Cl | a4 | H | 4-Br |
| a1 | H | 4-Cl | a32 | H | 4-Cl | a23 | H | 4-Br |
| a2 | H | 4-Cl | a33 | H | 4-Cl | a25 | H | 4-Br |
| a3 | H | 4-Cl | a34 | H | 4-Cl | a26 | H | 4-Br |
| a4 | H | 4-Cl | a35 | H | 4-Cl | a35 | H | 4-Br |
| a5 | H | 4-Cl | a36 | H | 4-Cl | a1 | H | 4-I |
| a6 | H | 4-Cl | a37 | H | 4-Cl | a2 | H | 4-I |
| a7 | H | 4-Cl | a38 | H | 4-Cl | a4 | H | 4-I |
| a8 | H | 4-Cl | a39 | H | 4-Cl | a23 | H | 4-I |
| a9 | H | 4-Cl | a40 | H | 4-Cl | a25 | H | 4-I |
| a10 | H | 4-Cl | a41 | H | 4-Cl | a26 | H | 4-I |
| a11 | H | 4-Cl | a42 | H | 4-Cl | a35 | H | 4-I |
| a12 | H | 4-Cl | a43 | H | 4-Cl | a1 | H | 4-Me |
| a13 | H | 4-Cl | a44 | H | 4-Cl | a2 | H | 4-Me |
| a14 | H | 4-Cl | a45 | H | 4-Cl | a4 | H | 4-Me |
| a15 | H | 4-Cl | a46 | H | 4-Cl | a23 | H | 4-Me |
| a25 | H | 4-Me | a1 | H | 4-cHex | a25 | H | 4-CF$_3$ |
| a26 | H | 4-Me | a2 | H | 4-cHex | a26 | H | 4-CF$_3$ |
| a35 | H | 4-Me | a4 | H | 4-cHex | a27 | H | 4-CF$_3$ |
| a1 | H | 4-iPr | a23 | H | 4-cHex | a28 | H | 4-CF$_3$ |
| a2 | H | 4-iPr | a25 | H | 4-cHex | a29 | H | 4-CF$_3$ |
| a4 | H | 4-iPr | a26 | H | 4-cHex | a30 | H | 4-CF$_3$ |
| a23 | H | 4-iPr | a35 | H | 4-cHex | a31 | H | 4-CF$_3$ |
| a25 | H | 4-iPr | a1 | H | 4-CF$_3$ | a32 | H | 4-CF$_3$ |
| a26 | H | 4-iPr | a2 | H | 4-CF$_3$ | a33 | H | 4-CF$_3$ |
| a35 | H | 4-iPr | a3 | H | 4-CF$_3$ | a34 | H | 4-CF$_3$ |
| a1 | H | 4-tBu | a4 | H | 4-CF$_3$ | a35 | H | 4-CF$_3$ |
| a2 | H | 4-tBu | a5 | H | 4-CF$_3$ | a36 | H | 4-CF$_3$ |
| a4 | H | 4-tBu | a6 | H | 4-CF$_3$ | a37 | H | 4-CF$_3$ |
| a23 | H | 4-tBu | a7 | H | 4-CF$_3$ | a38 | H | 4-CF$_3$ |
| a25 | H | 4-tBu | a8 | H | 4-CF$_3$ | a39 | H | 4-CF$_3$ |
| a26 | H | 4-tBu | a9 | H | 4-CF$_3$ | a40 | H | 4-CF$_3$ |
| a35 | H | 4-tBu | a10 | H | 4-CF$_3$ | a41 | H | 4-CF$_3$ |
| a1 | H | 4-nHex | a11 | H | 4-CF$_3$ | a42 | H | 4-CF$_3$ |
| a2 | H | 4-nHex | a12 | H | 4-CF$_3$ | a43 | H | 4-CF$_3$ |
| a4 | H | 4-nHex | a13 | H | 4-CF$_3$ | a44 | H | 4-CF$_3$ |
| a23 | H | 4-nHex | a14 | H | 4-CF$_3$ | a45 | H | 4-CF$_3$ |
| a25 | H | 4-nHex | a15 | H | 4-CF$_3$ | a46 | H | 4-CF$_3$ |
| a26 | H | 4-nHex | a16 | H | 4-CF$_3$ | a47 | H | 4-CF$_3$ |
| a35 | H | 4-nHex | a17 | H | 4-CF$_3$ | a48 | H | 4-CF$_3$ |
| a1 | H | 4-cPr | a18 | H | 4-CF$_3$ | a49 | H | 4-CF$_3$ |
| a2 | H | 4-cPr | a19 | H | 4-CF$_3$ | a50 | H | 4-CF$_3$ |
| a4 | H | 4-cPr | a20 | H | 4-CF$_3$ | a51 | H | 4-CF$_3$ |
| a23 | H | 4-cPr | a21 | H | 4-CF$_3$ | a52 | | H 4-CF$_3$ |
| a25 | H | 4-cPr | a22 | H | 4-CF$_3$ | a53 | | 4-CF$_3$ |
| a26 | H | 4-cPr | a23 | H | 4-CF$_3$ | a54 | H | 4-CF$_3$ |
| a35 | H | 4-cPr | a24 | H | 4-CF$_3$ | a55 | H | 4-CF$_3$ |
| a56 | H | 4-CF$_3$ | a35 | H | 4-OCF$_3$ | a25 | H | 4-(3-thienyl) |
| a57 | H | 4-CF$_3$ | a25 | H | 4-Sme | a35 | H | 4-(3-thienyl) |
| a58 | H | 4-CF$_3$ | a35 | H | 4-Sme | a25 | H | 4-(2-pyridyl) |
| a59 | H | 4-CF$_3$ | a25 | H | 4-SOMe | a35 | H | 4-(2-pyridyl) |
| a1 | H | 4-OMe | a35 | H | 4-SOMe | a25 | H | 4-(3-pyridyl) |
| a2 | H | 4-OMe | a25 | H | 4-SO$_2$Me | a35 | H | 4-(3-pyridyl) |
| a4 | H | 4-OMe | a35 | H | 4-SO$_2$Me | a25 | H | 4-(4-pyridyl) |
| a23 | H | 4-OMe | a25 | H | 4-NHMe | a35 | H | 4-(4-pyridyl) |
| a25 | H | 4-OMe | a35 | H | 4-NHMe | a25 | H | 4-Ph |
| a26 | H | 4-OMe | a25 | H | 4-NMe$_2$ | a35 | H | 4-Ph |
| a35 | H | 4-OMe | a35 | H | 4-NMe$_2$ | a25 | H | 4-(4-Cl—Ph) |
| a1 | H | 4-OiPr | a25 | H | 4-SiMe$_4$ | a35 | H | 4-(4-Cl—Ph) |
| a2 | H | 4-OiPr | a35 | H | 4-SiMe$_4$ | a25 | H | 4-(4-F—Ph) |
| a4 | H | 4-OiPr | a25 | H | 4-CH$_2$OEt | a35 | H | 4-(4-F—Ph) |
| a23 | H | 4-OiPr | a35 | H | 4-CH$_2$OEt | a25 | H | 4-OPh |
| a25 | H | 4-OiPr | a25 | H | 4-CH$_2$Set | a35 | H | 4-OPh |
| a26 | H | 4-OiPr | a35 | H | 4-CH$_2$Set | a1 | H | 2-Cl |
| a35 | H | 4-OiPr | a25 | H | 4-COMe | a2 | H | 2-Cl |
| a1 | H | 4-OtBu | a35 | H | 4-COMe | a4 | H | 2-Cl |
| a2 | H | 4-OtBu | a25 | H | 4-CotBu | a23 | H | 2-Cl |

TABLE 1-continued

| | | | | | | | | |
|---|---|---|---|---|---|---|---|---|
| a4 | H | 4-OtBu | a35 | H | 4-CotBu | a25 | H | 2-Cl |
| a23 | H | 4-OtBu | a25 | H | 4-CO$_2$Me | a26 | H | 2-Cl |
| a25 | H | 4-OtBu | a35 | H | 4-CO$_2$Me | a35 | H | 2-Cl |
| a26 | H | 4-OtBu | a25 | H | 4-CO$_2$tBu | a1 | H | 2,4-F$_2$ |
| a35 | H | 4-OtBu | a35 | H | 4-CO$_2$tBu | a2 | H | 2,4-F$_2$ |
| a1 | H | 4-OCF$_3$ | a25 | H | 4-CH$_2$Ph | a4 | H | 2,4-F$_2$ |
| a2 | H | 4-OCF$_3$ | a35 | H | 4-CH$_2$Ph | a23 | H | 2,4-F$_2$ |
| a4 | H | 4-OCF$_3$ | a25 | H | 4-OCH$_2$Ph | a25 | H | 2,4-F$_2$ |
| a23 | H | 4-OCF$_3$ | a35 | H | 4-OCH$_2$Ph | a26 | H | 2,4-F$_2$ |
| a25 | H | 4-OCF$_3$ | a25 | H | 4-(2-thienyl) | a35 | H | 2,4-F$_2$ |
| a2 | H | 2,6-F$_2$ | a25 | H | 2,3,4,5,6-F$_5$ | a8 | H | 3-F |
| a4 | H | 2,6-F$_2$ | a26 | H | 2,3,4,5,6-F$_5$ | a9 | H | 3-F |
| a23 | H | 2,6-F$_2$ | a35 | H | 2,3,4,5,6-F$_5$ | a10 | H | 3-F |
| a25 | H | 2,6-F$_2$ | a1 | H | 2,3,4,5,6-Cl$_5$ | a11 | H | 3-F |
| a26 | H | 2,6-F$_2$ | a2 | H | 2,3,4,5,6-Cl$_5$ | a12 | H | 3-F |
| a35 | H | 2,6-F$_2$ | a4 | H | 2,3,4,5,6-Cl$_5$ | a13 | H | 3-F |
| a1 | H | 2,4-Cl$_2$ | a23 | H | 2,3,4,5,6-Cl$_5$ | a14 | H | 3-F |
| a2 | H | 2,4-Cl$_2$ | a25 | H | 2,3,4,5,6-Cl$_5$ | a15 | H | 3-F |
| a4 | H | 2,4-Cl$_2$ | a26 | H | 2,3,4,5,6-Cl$_5$ | a16 | H | 3-F |
| a23 | H | 2,4-Cl$_2$ | a35 | H | 2,3,4,5,6-Cl$_5$ | a17 | H | 3-F |
| a25 | H | 2,4-Cl$_2$ | a1 | H | 3-NO$_2$ | a18 | H | 3-F |
| a26 | H | 2,4-Cl$_2$ | a2 | H | 3-NO$_2$ | a19 | H | 3-F |
| a35 | H | 2,4-Cl$_2$ | a4 | H | 3-NO$_2$ | a20 | H | 3-F |
| a1 | H | 2,6-Cl$_2$ | a23 | H | 3-NO$_2$ | a21 | H | 3-F |
| a2 | H | 2,6-Cl$_2$ | a25 | H | 3-NO$_2$ | a22 | H | 3-F |
| a4 | H | 2,6-Cl$_2$ | a26 | H | 3-NO$_2$ | a23 | H | 3-F |
| a23 | H | 2,6-Cl$_2$ | a35 | H | 3-NO$_2$ | a24 | H | 3-F |
| a25 | H | 2,6-Cl$_2$ | a1 | H | 3-CN | a25 | H | 3-F |
| a26 | H | 2,6-Cl$_2$ | a2 | H | 3-CN | a26 | H | 3-F |
| a35 | H | 2,6-Cl$_2$ | a4 | H | 3-CN | a27 | H | 3-F |
| a1 | H | 2,4,6-Cl$_3$ | a23 | H | 3-CN | a28 | H | 3-F |
| a2 | H | 2,4,6-Cl$_3$ | a25 | H | 3-CN | a29 | H | 3-F |
| a4 | H | 2,4,6-Cl$_3$ | a26 | H | 3-CN | a30 | H | 3-F |
| a23 | H | 2,4,6-Cl$_3$ | a35 | H | 3-CN | a31 | H | 3-F |
| a25 | H | 2,4,6-Cl$_3$ | a1 | H | 3-F | a32 | H | 3-F |
| a26 | H | 2,4,6-Cl$_3$ | a2 | H | 3-F | a33 | H | 3-F |
| a35 | H | 2,4,6-Cl$_3$ | a3 | H | 3-F | a34 | H | 3-F |
| a1 | H | 2,3,4,5,6-F$_5$ | a4 | H | 3-F | a35 | H | 3-F |
| a2 | H | 2,3,4,5,6-F$_5$ | a5 | H | 3-F | a36 | H | 3-F |
| a4 | H | 2,3,4,5,6-F$_5$ | a6 | H | 3-F | a37 | H | 3-F |
| a23 | H | 2,3,4,5,6-F$_5$ | a7 | H | 3-F | a38 | H | 3-F |
| a39 | H | 3-F | a11 | H | 3-Cl | a42 | H | 3-Cl |
| a40 | H | 3-F | a12 | H | 3-Cl | a43 | H | 3-Cl |
| a41 | H | 3-F | a13 | H | 3-Cl | a44 | H | 3-Cl |
| a42 | H | 3-F | a14 | H | 3-Cl | a45 | H | 3-Cl |
| a43 | H | 3-F | a15 | H | 3-Cl | a46 | H | 3-Cl |
| a44 | H | 3-F | a16 | H | 3-Cl | a47 | H | 3-Cl |
| a45 | H | 3-F | a17 | H | 3-Cl | a48 | H | 3-Cl |
| a46 | H | 3-F | a18 | H | 3-Cl | a49 | H | 3-Cl |
| a47 | H | 3-F | a19 | H | 3-Cl | a50 | H | 3-Cl |
| a48 | H | 3-F | a20 | H | 3-Cl | a51 | H | 3-Cl |
| a49 | H | 3-F | a21 | H | 3-Cl | a52 | H | 3-Cl |
| a50 | H | 3-F | a22 | H | 3-Cl | a53 | H | 3-Cl |
| a51 | H | 3-F | a23 | H | 3-Cl | a54 | H | 3-Cl |
| a52 | H | 3-F | a24 | H | 3-Cl | a55 | H | 3-Cl |
| a53 | H | 3-F | a25 | H | 3-Cl | a56 | H | 3-Cl |
| a54 | H | 3-F | a26 | H | 3-Cl | a57 | H | 3-Cl |
| a55 | H | 3-F | a27 | H | 3-Cl | a58 | H | 3-Cl |
| a56 | H | 3-F | a28 | H | 3-Cl | a59 | H | 3-Cl |
| a57 | H | 3-F | a29 | H | 3-Cl | a1 | H | 3-Br |
| a58 | H | 3-F | a30 | H | 3-Cl | a2 | H | 3-Br |
| a59 | H | 3-F | a31 | H | 3-Cl | a4 | H | 3-Br |
| a1 | H | 3-Cl | a32 | H | 3-Cl | a23 | H | 3-Br |
| a2 | H | 3-Cl | a33 | H | 3-Cl | a25 | H | 3-Br |
| a3 | H | 3-Cl | a34 | H | 3-Cl | a26 | H | 3-Br |
| a4 | H | 3-Cl | a35 | H | 3-Cl | a35 | H | 3-Br |
| a5 | H | 3-Cl | a36 | H | 3-Cl | a1 | H | 3-I |
| a6 | H | 3-Cl | a37 | H | 3-Cl | a2 | H | 3-I |
| a7 | H | 3-Cl | a38 | H | 3-Cl | a4 | H | 3-I |
| a8 | H | 3-Cl | a39 | H | 3-Cl | a23 | H | 3-I |
| a9 | H | 3-Cl | a40 | H | 3-Cl | a25 | H | 3-I |
| a10 | H | 3-Cl | a41 | H | 3-Cl | a26 | H | 3-I |
| a35 | H | 3-I | a4 | H | 3-cPr | a20 | H | 3-CF$_3$ |
| a1 | H | 3-Me | a23 | H | 3-cPr | a21 | H | 3-CF$_3$ |
| a2 | H | 3-Me | a25 | H | 3-cPr | a22 | H | 3-CF$_3$ |
| a4 | H | 3-Me | a26 | H | 3-cPr | a23 | H | 3-CF$_3$ |
| a23 | H | 3-Me | a35 | H | 3-cPr | a24 | H | 3-CF$_3$ |
| a25 | H | 3-Me | a1 | H | 3-cHex | a25 | H | 3-CF$_3$ |
| a26 | H | 3-Me | a2 | H | 3-cHex | a26 | H | 3-CF$_3$ |

TABLE 1-continued

| | | | | | | | | |
|---|---|---|---|---|---|---|---|---|
| a35 | H | 3-Me | a4 | H | 3-cHex | a27 | H | 3-CF$_3$ |
| a1 | H | 3-iPr | a23 | H | 3-cHex | a28 | H | 3-CF$_3$ |
| a2 | H | 3-iPr | a25 | H | 3-cHex | a29 | H | 3-CF$_3$ |
| a4 | H | 3-iPr | a26 | H | 3-cHex | a30 | H | 3-CF$_3$ |
| a23 | H | 3-iPr | a35 | H | 3-cHex | a31 | H | 3-CF$_3$ |
| a26 | H | 3-iPr | a1 | H | 3-CF$_3$ | a32 | H | 3-CF$_3$ |
| a26 | H | 3-iPr | a2 | H | 3-CF$_3$ | a33 | H | 3-CF$_3$ |
| a35 | H | 3-iPr | a3 | H | 3-CF$_3$ | a34 | H | 3-CF$_3$ |
| a1 | H | 3-tBu | a4 | H | 3-CF$_3$ | a35 | H | 4-CF$_3$ |
| a2 | H | 3-tBu | a5 | H | 3-CF$_3$ | a36 | H | 3-CF$_3$ |
| a4 | H | 3-tBu | a6 | H | 3-CF$_3$ | a37 | H | 3-CF$_3$ |
| a23 | H | 3-tBu | a7 | H | 3-CF$_3$ | a38 | H | 3-CF$_3$ |
| a25 | H | 3-tBu | a8 | H | 3-CF$_3$ | a39 | H | 3-CF$_3$ |
| a26 | H | 3-tBu | a9 | H | 3-CF$_3$ | a40 | H | 4-CF$_3$ |
| a35 | H | 3-tBu | a10 | H | 3-CF$_3$ | a41 | H | 3-CF$_3$ |
| a1 | H | 3-nHex | a11 | H | 3-CF$_3$ | a42 | H | 3-CF$_3$ |
| a2 | H | 3-nHex | a12 | H | 3-CF$_3$ | a43 | H | 3-CF$_3$ |
| a4 | H | 3-nHex | a13 | H | 3-CF$_3$ | a44 | H | 4-CF$_3$ |
| a23 | H | 3-nHex | a14 | H | 3-CF$_3$ | a45 | H | 3-CF$_3$ |
| a25 | H | 3-nHex | a15 | H | 3-CF$_3$ | a46 | H | 3-CF$_3$ |
| a26 | H | 3-nHex | a16 | H | 3-CF$_3$ | a47 | H | 3-CF$_3$ |
| a35 | H | 3-nHex | a17 | H | 3-CF$_3$ | a48 | H | 3-CF$_3$ |
| a1 | H | 3-cPr | a18 | H | 3-CF$_3$ | a49 | H | 3-CF$_3$ |
| a2 | H | 3-cPr | a19 | H | 3-CF$_3$ | a50 | H | 3-CF$_3$ |
| a51 | H | 3-CF$_3$ | a2 | H | 3-OCF$_3$ | a35 | H | 3-CH$_2$Ph |
| a52 | H | 3-CF$_3$ | a4 | H | 3-OCF$_3$ | a25 | r6 | 3-OCH$_2$Ph |
| a53 | H | 3-CF$_3$ | a23 | H | 3-OCF$_3$ | a35 | H | 3-OCH$_2$Ph |
| a54 | H | 3-CF$_3$ | a25 | H | 3-OCF$_3$ | a25 | H | 3-(2-thienyl) |
| a55 | H | 3-CF$_3$ | a26 | H | 3-OCF$_3$ | a35 | H | 3-(2-thienyl) |
| a56 | H | 3-CF$_3$ | a35 | H | 3-OCF$_3$ | a25 | H | 3-(3-thienyl) |
| a57 | H | 3-CF$_3$ | a25 | H | 3-Sine | a35 | H | 3-(3-thienyl) |
| a58 | H | 3-CF$_3$ | a35 | H | 3-Sine | a25 | H | 3-(2-pyridyl) |
| a59 | H | 3-CF$_3$ | a25 | H | 3-SOMe | a35 | H | 3-(2-pyridyl) |
| a1 | H | 3-OMe | a35 | H | 3-SOMe | a25 | H | 3-(3-pyridyl) |
| a2 | H | 3-OMe | a25 | H | 3-SO$_{2Me}$ | a35 | H | 3-(3-pyridyl) |
| a4 | H | 3-OMe | a35 | H | 3-SO$_{2Me}$ | a25 | H | 3-(4-pyridyl) |
| a23 | H | 3-OMe | a25 | H | 3-NHMe | a35 | H | 3-(4-pyridyl) |
| a25 | H | 3-OMe | a35 | H | 3-NHMe | a25 | H | 3-Ph |
| a26 | H | 3-OMe | a25 | H | 3-NMe$_2$ | a35 | H | 3-Ph |
| a35 | H | 3-OMe | a35 | H | 3-NMe$_2$ | a25 | H | 3-(4-Cl-Ph) |
| a1 | H | 3-OiPr | a25 | H | 3-SiMe$_4$ | a35 | H | 3-(4-Cl-Ph) |
| a2 | H | 3-OiPr | a35 | H | 3-SiMe$_4$ | a25 | H | 3-(4-F-Ph) |
| a4 | H | 3-OiPr | a25 | H | 3-CH$_2$OEt | a35 | H | 3-(4-F-Ph) |
| a23 | H | 3-OiPr | a35 | H | 3-CH$_2$OEt | a25 | H | 3-OPh |
| a25 | H | 3-OiPr | a25 | H | 3-CH$_2$Set | a35 | H | 3-OPh |
| a26 | H | 3-OiPr | a35 | H | 3-CH$_2$Set | a1 | H | 3,5-Cl$_2$ |
| a35 | H | 3-OiPr | a25 | H | 3-COMe | a2 | H | 3,5-Cl$_2$ |
| a1 | H | 3-OtBu | a35 | H | 3-COMe | a3 | H | 3,5-Cl$_2$ |
| a2 | H | 3-OtBu | a25 | H | 3-CotBu | a4 | H | 3,5-Cl$_2$ |
| a4 | H | 3-OtBu | a35 | H | 3-CotBu | a5 | H | 3,5-Cl$_2$ |
| a23 | H | 3-OtBu | a25 | H | 3-CO$_2$Me | a6 | H | 3,5-Cl$_2$ |
| a25 | H | 3-OtBu | a35 | H | 3-CO$_2$Me | a7 | H | 3,5-Cl$_2$ |
| a26 | H | 3-OtBu | a25 | H | 3-CO$_2$tBu | a8 | H | 3,5-Cl$_2$ |
| a35 | H | 3-OtBu | a35 | H | 3-CO$_2$tBu | a9 | H | 3,5-Cl$_2$ |
| a1 | H | 3-OCF$_3$ | a25 | H | 3-CH$_2$Ph | a10 | H | 3,5-Cl$_2$ |
| a11 | H | 3,5-Cl$_2$ | a42 | H | 3,5-Cl$_2$ | a14 | H | 3,5-F$_2$ |
| a12 | H | 3,5-Cl$_2$ | a43 | H | 3,5-Cl$_2$ | a15 | H | 3,5-F$_2$ |
| a13 | H | 3,5-Cl$_2$ | a44 | H | 3,5-Cl$_2$ | a16 | H | 3,5-F$_2$ |
| a14 | H | 3,5-Cl$_2$ | a45 | H | 3,5-Cl$_2$ | a17 | H | 3,5-F$_2$ |
| a15 | H | 3,5-Cl$_2$ | a46 | H | 3,5-Cl$_2$ | a18 | H | 3,5-F$_2$ |
| a16 | H | 3,5-Cl$_2$ | a47 | H | 3,5-Cl$_2$ | a19 | H | 3,5-F$_2$ |
| a17 | H | 3,5-Cl$_2$ | a48 | H | 3,5-Cl$_2$ | a20 | H | 3,5-F$_2$ |
| a18 | H | 3,5-Cl$_2$ | a49 | H | 3,5-Cl$_2$ | a21 | H | 3,5-F$_2$ |
| a19 | H | 3,5-Cl$_2$ | a50 | H | 3,5-Cl$_2$ | a22 | H | 3,5-F$_2$ |
| a20 | H | 3,5-Cl$_2$ | a51 | H | 3,5-Cl$_2$ | a23 | H | 3,5-F$_2$ |
| a21 | H | 3,5-Cl$_2$ | a52 | H | 3,5-Cl$_2$ | a24 | H | 3,5-F$_2$ |
| a22 | H | 3,5-Cl$_2$ | a53 | H | 3,5-Cl$_2$ | a25 | H | 3,5-F$_2$ |
| a23 | H | 3,5-Cl$_2$ | a54 | H | 3,5-Cl$_2$ | a26 | H | 3,5-F$_2$ |
| a24 | H | 3,5-Cl$_2$ | a55 | H | 3,5-Cl$_2$ | a27 | H | 3,5-F$_2$ |
| a25 | H | 3,5-Cl$_2$ | a56 | H | 3,5-Cl$_2$ | a28 | H | 3,5-F$_2$ |
| a26 | H | 3,5-Cl$_2$ | a57 | H | 3,5-Cl$_2$ | a29 | H | 3,5-F$_2$ |
| a27 | H | 3,5-Cl$_2$ | a58 | H | 3,5-Cl$_2$ | a30 | H | 3,5-F$_2$ |
| a28 | H | 3,5-Cl$_2$ | a59 | H | 3,5-Cl$_2$ | a31 | H | 3,5-F$_2$ |
| a29 | H | 3,5-Cl$_2$ | a1 | H | 3,5-F$_2$ | a32 | H | 3,5-F$_2$ |
| a30 | H | 3,5-Cl$_2$ | a2 | H | 3,5-F$_2$ | a33 | H | 3,5-F$_2$ |
| a31 | H | 3,5-Cl$_2$ | a3 | H | 3,5-F$_2$ | a34 | H | 3,5-F$_2$ |
| a32 | H | 3,5-Cl$_2$ | a4 | H | 3,5-F$_2$ | a35 | H | 3,5-F$_2$ |
| a33 | H | 3,5-Cl$_2$ | a5 | H | 3,5-F$_2$ | a36 | H | 3,5-F$_2$ |
| a34 | H | 3,5-Cl$_2$ | a6 | H | 3,5-F$_2$ | a37 | H | 3,5-F$_2$ |

TABLE 1-continued

| | | | | | | | | |
|---|---|---|---|---|---|---|---|---|
| a35 | H | 3,5-Cl$_2$ | a7 | H | 3,5-F$_2$ | a38 | H | 3,S-F$_2$ |
| a36 | H | 3,5-Cl$_2$ | a8 | H | 3,S-F$_2$ | a39 | H | 3,S-F$_2$ |
| a37 | H | 3,5-Cl$_2$ | a9 | H | 3,5-F$_2$ | a40 | H | 3,S-F$_2$ |
| a38 | H | 3,5-Cl$_2$ | a19 | H | 3,S-F$_2$ | a41 | H | 3,S-F$_2$ |
| a39 | H | 3,5-Cl$_2$ | a11 | H | 3,5-F$_2$ | a42 | H | 3,S-F$_2$ |
| a40 | H | 3,5-Cl$_2$ | a12 | H | 3,5-F$_2$ | a43 | H | 3,S-F$_2$ |
| a41 | H | 3,5-Cl$_2$ | a13 | H | 3,5-F$_2$ | a44 | H | 3,5-F$_2$ |
| a45 | H | 3,5-F$_9$ | a17 | H | 3,5-Me$_9$ | a48 | H | 3,5-Me$_9$ |
| a46 | H | 3,5-F$_2$ | a18 | H | 3,5-Me$_2$ | a49 | H | 3,5-Me$_2$ |
| a47 | H | 3,5-F$_2$ | a19 | H | 3,5-Me$_2$ | a50 | H | 3,5-Me$_2$ |
| a48 | H | 3,5-F$_2$ | a20 | H | 3,5-Me$_2$ | a51 | H | 3,5-Me$_2$ |
| a49 | H | 3,5-F$_2$ | a21 | H | 3,5-Me$_2$ | a52 | H | 3,5-Me$_2$ |
| a50 | H | 3,5-F$_2$ | a22 | H | 3,5-Me$_2$ | a53 | H | 3,5-Me$_2$ |
| a51 | H | 3,5-F$_2$ | a23 | H | 3,5-Me$_2$ | a54 | H | 3,5-Me$_2$ |
| a52 | H | 3,5-F$_2$ | a24 | H | 3,5-Me$_2$ | aSS | H | 3,5-Me$_2$ |
| a53 | H | 3,5-F$_2$ | a25 | H | 3,5-Me$_2$ | a56 | H | 3,5-Me$_2$ |
| a54 | H | 3,5-F$_2$ | a26 | H | 3,5-Me$_2$ | a57 | H | 3,5-Me$_2$ |
| a55 | H | 3,5-F$_2$ | a27 | H | 3,5-Me$_2$ | a58 | H | 3,5-Me$_2$ |
| a56 | H | 3,5-F$_2$ | a28 | H | 3,5-Me$_2$ | a59 | H | 3,5-Me$_2$ |
| a57 | H | 3,5-F$_2$ | a29 | H | 3,5-Me$_2$ | a60 | H | — |
| a58 | H | 3,5-F$_2$ | a30 | H | 3,5-Me$_2$ | a60 | H | 4-F |
| a59 | H | 3,5-F$_2$ | a31 | H | 3,5-Me$_2$ | a60 | H | 4-Cl |
| a1 | H | 3,5-Me$_2$ | a32 | H | 3,5-Me$_2$ | a60 | H | 4-iPr |
| a2 | H | 3,5-Me$_2$ | a33 | H | 3,5-Me$_2$ | a60 | H | 4-tBu |
| a3 | H | 3,5-Me$_2$ | a34 | H | 3,5-Me$_2$ | a60 | H | 4-CF$_3$ |
| a4 | H | 3,5-Me$_2$ | a35 | H | 3,5-Me$_2$ | a60 | H | 3-F |
| a5 | H | 3,5-Me$_2$ | a36 | H | 3,5-Me$_2$ | a60 | H | 3-Cl |
| a6 | H | 3,5-Me$_2$ | a37 | H | 3,5-Me$_2$ | a60 | H | 3-iPr |
| a7 | H | 3,5-Me$_2$ | a38 | H | 3,5-Me$_2$ | a60 | H | 3-tBu |
| a8 | H | 3,5-Me$_2$ | a39 | H | 3,5-Me$_2$ | a60 | H | 3-CF$_3$ |
| a9 | H | 3,5-Me$_2$ | a40 | H | 3,5-Me$_2$ | a60 | H | 3,5-F$_2$ |
| a10 | H | 3,5-Me$_2$ | a41 | H | 3,5-Me$_2$ | a60 | H | 3,S-Cl$_2$ |
| a11 | H | 3,5-Me$_2$ | a42 | H | 3,5-Me$_2$ | a60 | H | 3,5-Me |
| a12 | H | 3,5-Me$_2$ | a43 | H | 3,5-Me$_2$ | a60 | H | 3,5-OMe$_2$ |
| a13 | H | 3,5-Me$_2$ | a44 | H | 3,5-Me$_2$ | | | |
| a14 | H | 3,5-Me$_2$ | a45 | H | 3,5-Me$_2$ | | | |
| a15 | H | 3,5-Me$_2$ | a46 | H | 3,5-Me$_2$ | | | |
| a16 | H | 3,5-Me$_2$ | a47 | H | 3,5-Me$_2$ | | | |

TABLE 2

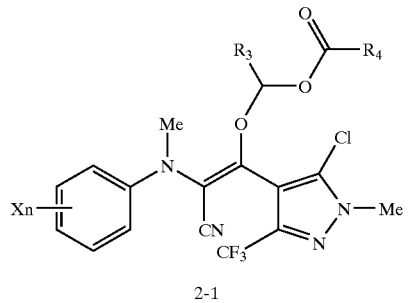

2-1

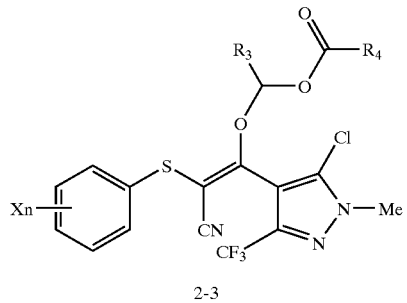

2-3

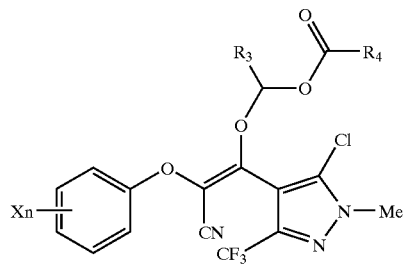

2-2

TABLE 2-continued

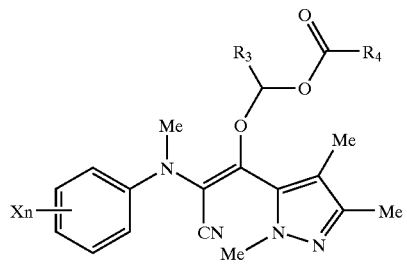

2-4

TABLE 2-continued
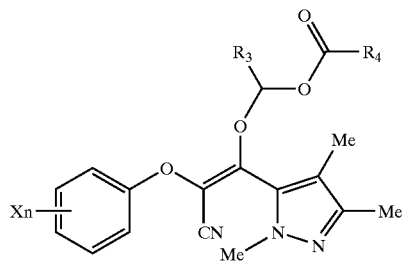
2-5
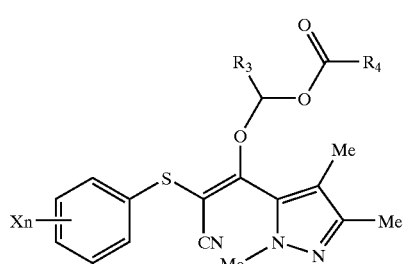
2-6
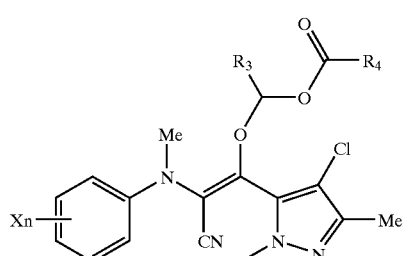
2-7
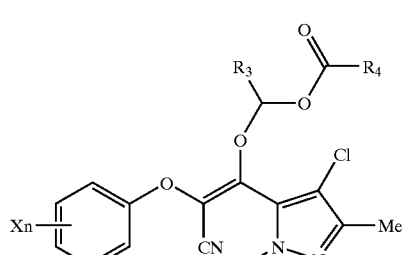
2-8
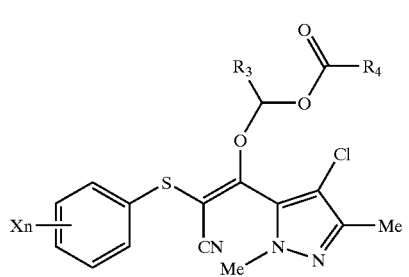
2-9
TABLE 2-continued
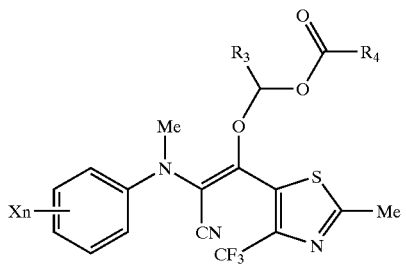
2-10
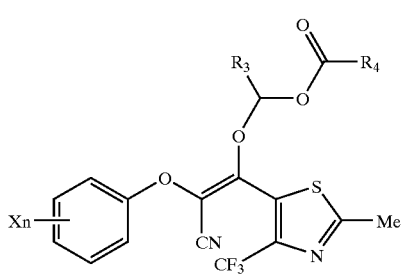
2-11
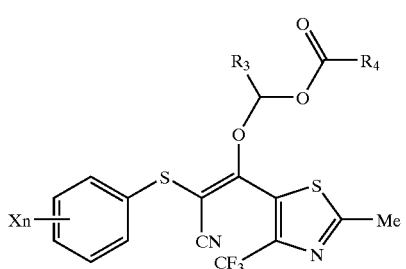
2-12
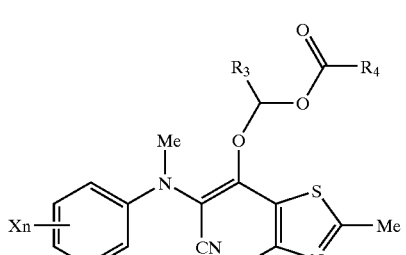
2-13
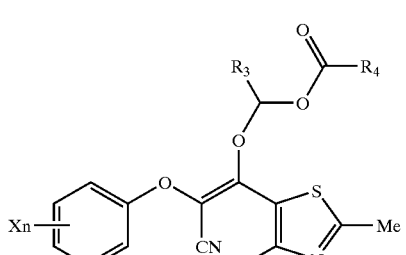
2-14

TABLE 2-continued

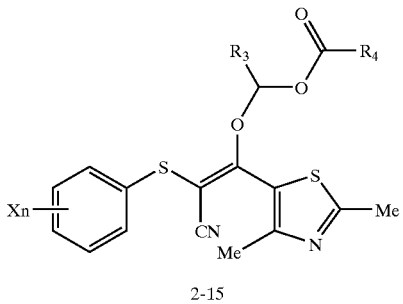

2-15

Combinations of $R_3$, $R_4$ and Xn of all compounds represented in the above formula 2-1 through 2-15 are exemplified in the following tables.

| $R_3$ | $R_4$ | Xn | $R_3$ | $R_4$ | Xn |
|---|---|---|---|---|---|
| Me | Me | 4-F | Me | cHex | 4-Cl |
| Me | Et | 4-F | Me | OMe | 4-Cl |
| Me | nPr | 4-F | Me | OEt | 4-Cl |
| Me | iPr | 4-F | Me | OnPr | 4-Cl |
| Me | nBu | 4-F | Me | OiPr | 4-Cl |
| Me | iBu | 4-F | Me | OnBu | 4-Cl |
| Me | nPen | 4-F | Me | OiBu | 4-Cl |
| Me | nHex | 4-F | Me | OnPen | 4-Cl |
| Me | cPr | 4-F | Me | OnHex | 4-Cl |
| Me | cBu | 4-F | Me | Ph | 4-Cl |
| Me | cPen | 4-F | Me | Me | 4-tBu |
| Me | cHex | 4-F | Me | Et | 4-tBu |
| Me | OMe | 4-F | Me | nPr | 4-tBu |
| Me | OEt | 4-F | Me | iPr | 4-tBu |
| Me | OnPr | 4-F | Me | nBu | 4-tBu |
| Me | OiPr | 4-F | Me | iBu | 4-tBu |
| Me | OnBu | 4-F | Me | nPen | 4-tBu |
| Me | OiBu | 4-F | Me | nHex | 4-tBu |
| Me | OnPen | 4-F | Me | cPr | 4-tBu |
| Me | OnHex | 4-F | Me | cBu | 4-tBu |
| Me | Ph | 4-F | Me | cPen | 4-tBu |
| Me | Me | 4-Cl | Me | cHex | 4-tBu |
| Me | Et | 4-Cl | Me | OMe | 4-tBu |
| Me | nPr | 4-Cl | Me | OEt | 4-tBu |
| Me | iPr | 4-Cl | Me | OnPr | 4-tBu |
| Me | nBu | 4-Cl | Me | OiPr | 4-tBu |
| Me | iBu | 4-Cl | Me | OnBu | 4-tBu |
| Me | nPen | 4-Cl | Me | OiBu | 4-tBu |
| Me | nHex | 4-Cl | Me | OnPen | 4-tBu |
| Me | cPr | 4-Cl | Me | OnHex | 4-tBu |
| Me | cBu | 4-Cl | Me | Ph | 4-tBu |
| Me | cPen | 4-Cl | Me | Me | 4-$CF_3$ |
| Me | Et | 4-$CF_3$ | Me | OMe | 3-F |
| Me | Et | 4-$CF_3$ | Me | OEt | 3-F |
| Me | iPr | 4-$CF_3$ | Me | OnPr | 3-F |
| Me | nBu | 4-$CF_3$ | Me | OiPr | 3-F |
| Me | iBu | 4-$CF_3$ | Me | OnBu | 3-F |
| Me | nPen | 4-$CF_3$ | Me | OiBu | 3-F |
| Me | nHex | 4-$CF_3$ | Me | OnPen | 3-F |
| Me | cPr | 4-$CF_3$ | Me | OnHex | 3-F |
| Me | cBu | 4-$CF_3$ | Me | Ph | 3-F |
| Me | cPen | 4-$CF_3$ | Me | Me | 3-Cl |
| Me | cHex | 4-$CF_3$ | Me | Et | 3-Cl |
| Me | OMe | 4-$CF_3$ | Me | nPr | 3-Cl |
| Me | OEt | 4-$CF_3$ | Me | iPr | 3-Cl |
| Me | OnPr | 4-$CF_3$ | Me | nBu | 3-Cl |
| Me | OiPr | 4-$CF_3$ | Me | iBu | 3-Cl |
| Me | OnBu | 4-$CF_3$ | Me | cPen | 3-Cl |
| Me | OiBu | 4-$CF_3$ | Me | nHex | 3-Cl |
| Me | OnPen | 4-$CF_3$ | Me | cPr | 3-Cl |
| Me | OnHex | 4-$CF_3$ | Me | cBu | 3-Cl |
| Me | Ph | 4-$CF_3$ | Me | cPen | 3-Cl |
| Me | Me | 3-F | Me | cHex | 3-Cl |
| Me | Et | 3-F | Me | OMe | 3-Cl |
| Me | nPr | 3-F | Me | OEt | 3-Cl |
| Me | iPr | 3-F | Me | OnPr | 3-Cl |
| Me | nBu | 3-F | Me | OiPr | 3-Cl |
| Me | iBu | 3-F | Me | OnBu | 3-Cl |
| Me | nPen | 3-F | Me | OiBu | 3-Cl |
| Me | nHex | 3-F | Me | OnPen | 3-Cl |
| Me | cPr | 3-F | Me | OnHex | 3-Cl |
| Me | cBu | 3-F | Me | Ph | 3-Cl |
| Me | cPen | 3-F | Me | Me | 3-tBu |
| Me | cHex | 3-F | Me | Et | 3-tBu |
| Me | nPr | 3-tBu | Me | OEt | 3,5-$F_2$ |
| Me | iPr | 3-tBu | Me | OnPr | 3,5-$F_2$ |
| Me | nBu | 3-tBu | Me | OiPr | 3,5-$F_2$ |
| Me | iBu | 3-tBu | Me | OnBu | 3,5-$F_2$ |
| Me | nPen | 3-tBu | Me | OiBu | 3,5-$F_2$ |
| Me | nHex | 3-tBu | Me | OnPen | 3,5-$F_2$ |
| Me | cPr | 3-tBu | Me | OnHex | 3,5-$F_2$ |
| Me | cBu | 3-tBu | Me | Ph | 3,5-$F_2$ |
| Me | cPen | 3-tBu | Me | Me | 3,5-$Cl_2$ |
| Me | cHex | 3-tBu | Me | Et | 3,5-$Cl_2$ |
| Me | OMe | 3-tBu | Me | nPr | 3,5-$Cl_2$ |
| Me | OEt | 3-tBu | Me | iPr | 3,5-$Cl_2$ |
| Me | OnPr | 3-tBu | Me | nBu | 3,5-$Cl_2$ |
| Me | OiPr | 3-tBu | Me | iBu | 3,5-$Cl_2$ |
| Me | OnBu | 3-tBu | Me | nPen | 3,5-$Cl_2$ |
| Me | OiBu | 3-tBu | Me | nHex | 3,5-$Cl_2$ |
| Me | OnPen | 3-tBu | Me | cPr | 3,5-$Cl_2$ |
| Me | OnHex | 3-tBu | Me | cBu | 3,5-$Cl_2$ |
| Me | Ph | 3-tBu | Me | cPen | 3,5-$Cl_2$ |
| Me | Me | 3,5-$F_2$ | Me | cHex | 3,5-$Cl_2$ |
| Me | Et | 3,5-$F_2$ | Me | OMe | 3,5-$Cl_2$ |
| Me | nPr | 3,5-$F_2$ | Me | OEt | 3,5-$Cl_2$ |
| Me | iPr | 3,5-$F_2$ | Me | OnPr | 3,5-$Cl_2$ |
| Me | nBu | 3,5-$F_2$ | Me | OiPr | 3,5-$Cl_2$ |
| Me | iBu | 3,5-$F_2$ | Me | OnBu | 3,5-$Cl_2$ |
| Me | nPen | 3,5-$F_2$ | Me | OiBu | 3,5-$Cl_2$ |
| Me | nHex | 3,5-$F_2$ | Me | OnPen | 3,5-$Cl_2$ |
| Me | cPr | 3,5-$F_2$ | Me | OnHex | 3,5-$Cl_2$ |
| Me | cBu | 3,5-$F_2$ | Me | Ph | 3,5-$Cl_2$ |
| Me | cPen | 3,5-$F_2$ | Me | Me | 3,5-$Cl_2$ |
| Me | cHex | 3,5-$F_2$ | Me | Et | 3,5-$Cl_2$ |
| Me | OMe | 3,5-$F_2$ | Me | nPr | 3,5-$Cl_2$ |
| Me | iPr | 3,5-$Cl_2$ | Me | OnPr | 3,5-$Me_2$ |
| Me | nBu | 3,5-$Cl_2$ | Me | OiPr | 3,5-$Me_2$ |
| Me | iBu | 3,5-$Cl_2$ | Me | OnBu | 3,5-$Me_2$ |
| Me | nPen | 3,5-$Cl_2$ | Me | OiBu | 3,5-$Me_2$ |
| Me | nHex | 3,5-$Cl_2$ | Me | OnPen | 3,5-$Me_2$ |
| Me | cPr | 3,5-$Cl_2$ | Me | OnHex | 3,5-$Me_2$ |
| Me | cBu | 3,5-$Cl_2$ | Me | Ph | 3,5-$Me_2$ |
| Me | cPen | 3,5-$Cl_2$ | Et | nPr | 4-F |
| Me | cHex | 3,5-$Cl_2$ | Et | tBu | 4-F |
| Me | OMe | 3,5-$Cl_2$ | Et | cPr | 4-F |
| Me | OEt | 3,5-$Cl_2$ | Et | OEt | 4-F |
| Me | OnPr | 3,5-$Cl_2$ | Et | nPr | 4-Cl |
| Me | OiPr | 3,5-$Cl_2$ | Et | tBu | 4-Cl |
| Me | OnBu | 3,5-$Cl_2$ | Et | cPr | 4-Cl |
| Me | OiBu | 3,5-$Cl_2$ | Et | OEt | 4-Cl |
| Me | OnPen | 3,5-$Cl_2$ | Et | nPr | 4-tBu |
| Me | OnHex | 3,5-$Cl_2$ | Et | tBu | 4-tBu |
| Me | Ph | 3,5-$Cl_2$ | Et | cPr | 4-tBu |
| Me | Me | 3,5-$Me_2$ | Et | OEt | 4-tBu |
| Me | Et | 3,5-$Me_2$ | Et | nPr | 4-$CF_3$ |
| Me | nPr | 3,5-$Me_2$ | Et | tBu | 4-$CF_3$ |
| Me | iPr | 3,5-$Me_2$ | Et | cPr | 4-$CF_3$ |
| Me | nBu | 3,5-$Me_2$ | Et | OEt | 4-$CF_3$ |
| Me | tBu | 3,5-$Me_2$ | Et | nPr | 3-Cl |
| Me | nPen | 3,5-$Me_2$ | Et | tBu | 3-Cl |
| Me | nHex | 3,5-$Me_2$ | Et | cPr | 3-Cl |
| Me | cPr | 3,5-$Me_2$ | Et | OEt | 3-Cl |
| Me | cBu | 3,5-$Me_2$ | Et | nPr | 3-tBu |
| Me | cPen | 3,5-$Me_2$ | Et | tBu | 3-tBu |
| Me | cHex | 3,5-$Me_2$ | Et | cPr | 3-tBu |
| Me | OMe | 3,5-$Me_2$ | Et | OEt | 3-tBu |
| Me | OEt | 3,5-$Me_2$ | Et | nPr | 3,5-$Cl_2$ |
| Et | tBu | 3,5-$Cl_2$ | nPr | tBu | 3,5-$Cl_2$ |
| Et | cPr | 3,5-$Cl_2$ | nPr | cPr | 3,5-$Cl_2$ |
| Et | OEt | 3,5-$Cl_2$ | nPr | OEt | 3,5-$Cl_2$ |
| Et | nPr | 3,5-$Me_2$ | nPr | nPr | 3,5-$Me_2$ |
| Et | tBu | 3,5-$Me_2$ | nPr | tBu | 3,5-$Me_2$ |
| Et | cPr | 3,5-$Me_2$ | nPr | cPr | 3,5-$Me_2$ |
| Et | OEt | 3,5-$Me_2$ | nPr | OEt | 3,5-$Me_2$ |
| nPr | nPr | 4-F | iPr | nPr | 4-F |

TABLE 2-continued

| | | | | | |
|---|---|---|---|---|---|
| nPr | tBu | 4-F | iPr | tBu | 4-F |
| nPr | cPr | 4-F | iPr | cPr | 4-F |
| nPr | OEt | 4-F | iPr | OEt | 4-F |
| nPr | nPr | 4-Cl | iPr | nPr | 4-Cl |
| nPr | tBu | 4-Cl | iPr | tBu | 4-Cl |
| nPr | cPr | 4-Cl | iPr | cPr | 4-Cl |
| nPr | OEt | 4-Cl | iPr | OEt | 4-Cl |
| nPr | nPr | 4-tBu | iPr | nPr | 4-tBu |
| nPr | tBu | 4-tBu | iPr | tBu | 4-tBu |
| nPr | cPr | 4-tBu | iPr | cPr | 4-tBu |
| nPr | OEt | 4-tBu | iPr | OEt | 4-tBu |
| nPr | nPr | 4-$CF_3$ | iPr | nPr | 4-$CF_3$ |
| nPr | tBu | 4-$CF_3$ | iPr | tBu | 4-$CF_3$ |
| nPr | cPr | 4-$CF_3$ | iPr | cPr | 4-$CF_3$ |
| nPr | OEt | 4-$CF_3$ | iPr | OEt | 4-$CF_3$ |
| nPr | nPr | 3-Cl | iPr | nPr | 3-Cl |
| nPr | tBu | 3-Cl | iPr | tBu | 3-Cl |
| nPr | cPr | 3-Cl | iPr | cPr | 3-Cl |
| nPr | OEt | 3-Cl | iPr | OEt | 3-Cl |
| nPr | nPr | 3-tBu | iPr | nPr | 3-tBu |
| nPr | tBu | 3-tBu | iPr | tBu | 3-tBu |
| nPr | cPr | 3-tBu | iPr | cPr | 3-tBu |
| nPr | OEt | 3-tBu | iPr | OEt | 3-tBu |
| nPr | nPr | 3,5-$Cl_2$ | iPr | nPr | 3,5-$Cl_2$ |
| iPr | tBu | 3,5-$Cl_2$ | nBu | tBu | 3,5-$Cl_2$ |
| iPr | cPr | 3,5-$Cl_2$ | nBu | cPr | 3,5-$Cl_2$ |
| iPr | OEt | 3,5-$Cl_2$ | nBu | OEt | 3,5-$Cl_2$ |
| iPr | nPr | 3,5-$Me_2$ | nBu | nPr | 3,5-$Me_2$ |
| iPr | tBu | 3,5-$Me_2$ | nBu | tBu | 3,5-$Me_2$ |
| iPr | cPr | 3,5-$Me_2$ | nBu | cPr | 3,5-$Me_2$ |
| iPr | OEt | 3,5-$Me_2$ | nBu | OEt | 3,5-$Me_2$ |
| nBu | nPr | 4-F | tBu | nPr | 4-F |
| nBu | tBu | 4-F | tBu | tBu | 4-F |
| nBu | cPr | 4-F | tBu | cPr | 4-F |
| nBu | OEt | 4-F | tBu | OEt | 4-F |
| nBu | nPr | 4-Cl | tBu | nPr | 4-Cl |
| nBu | tBu | 4-Cl | tBu | tBu | 4-Cl |
| nBu | cPr | 4-Cl | tBu | cPr | 4-Cl |
| nBu | OEt | 4-Cl | tBu | OEt | 4-Cl |
| nBu | nPr | 4-tBu | tBu | nPr | 4-tBu |
| nBu | tBu | 4-tBu | tBu | tBu | 4-tBu |
| nBu | cPr | 4-tBu | tBu | cPr | 4-tBu |
| nBu | OEt | 4-tBu | tBu | OEt | 4-tBu |
| nBu | nPr | 4-$CF_3$ | tBu | nPr | 4-$CF_3$ |
| nBu | tBu | 4-$CF_3$ | tBu | tBu | 4-$CF_3$ |
| nBu | cPr | 4-$CF_3$ | tBu | cPr | 4-$CF_3$ |
| nBu | OEt | 4-$CF_3$ | tBu | OEt | 4-$CF_3$ |
| nBu | nPr | 3-Cl | tBu | nPr | 3-Cl |
| nBu | tBu | 3-Cl | tBu | tBu | 3-Cl |
| nBu | cPr | 3-Cl | tBu | cPr | 3-Cl |
| nBu | OEt | 3-Cl | tBu | OEt | 3-Cl |
| nBu | nPr | 3-tBu | tBu | nPr | 3-tBu |
| nBu | tBu | 3-tBu | tBu | tBu | 3-tBu |
| nBu | cPr | 3-tBu | tBu | cPr | 3-tBu |
| nBu | OEt | 3-tBu | tBu | OEt | 3-tBu |
| nBu | nPr | 3,5-$Cl_2$ | nPen | tBu | 4-Cl |

(Pest Controlling Agent)

The compounds of the present invention are useful as active ingredients for pest controlling agents, particularly as agricultural and horticultural insecticides, acaricides, sanitary pest controlling agents and anti-fouling agents for aqueous adhesive organisms. It is particularly preferable to apply compositions containing the compounds of the present invention as agricultural and horticultural insecticides and acaricides.

The compounds of the present invention can be used in their pure form without adding other ingredients, when they are actually applied as agricultural and horticultural insecticides or acaricides. When applied as agrochemicals, they may be used in forms that general agrochemicals can take, such as wettable powders, granules, dusts, emulsifiable concentrates, water soluble powders, flowable concentrates and flowables.

In order to make solid formulations, vegetable powders such as soybean flour and wheat flour, fine mineral powders such as diatomaceous earth, apatite, gypsum, talc, bentonite, pyrophylite and clay: and organic and inorganic compounds such as sodium benzoate, urea and Glauber's salt can be used as additives and carriers. When the purpose is to prepare liquid formulations, petroleum fractions such as kerosene, xylene and solvent naphtha, cyclohexane, cyclohexanone, N,N-dimethylformamide, dimethylsulfoxide, alcohol, acetone, methyl isobutyl ketone, mineral oils, vegetable oils, water and the like can be used as solvents.

It is possible to further add surfactant, if required, to make these formulations homogeneous and stable forms. There is no particular restriction on which surfactant can be used. Their examples include nonionic surfactant such as polyoxyethylene-added alkyl ethers, polyoxyethylene-added higher fatty acid esters, polyoxyethylene-added sorbitan higher fatty acid esters and polyoxyethylene-added tristylylphenyl ethers; polyoxyethylene-added alkylphenyl ether sulfates, alkylnaphthalene sulfonates, polycarboxylic acid salts, lignin sulfonates, condensation products of alkylnaphthalene sulfonates with formaldehyde, and copolymers of isobutylene and maleic anhydride.

An amount of the active ingredient in a formulation is preferably 0.01 to 90% by weight, more preferably about 0.05 to 85% by weight. The obtained wettable powders, emulsifiable concentrates, flowable concentrates and flowables are diluted with water to specified concentrations to use as suspensions or emulsions. The dusts and granules are used as they are to directly spray on plants or soil.

It goes without saying that the compounds of the present invention are sufficiently effective by themselves. They can be used, however, by mixing with one or more of various fungicides, insecticides, acaricides or synergists.

Representative examples of said fungicides, insecticides, acaricides and plant growth regulators that can be used to mix with the compounds of the present invention are recited in the following:

Fungicides:

Captan, Forpet, Thiuram, Ziram, Zineb, Maneb, Mancozeb, Propineb, Polycarbamate, Chlorothalonil, Quintozene, Captafol, Iprodione, Procymidone, Vinclozolin, Fluorimide, Cymoxanil, Mepronil, Flutolanil, Pencycuron, Oxycarboxine, Fosetyl aluminium, Propamocarb, Triadimefon, Triadimenol, Propiconazole, Diclobutrazol, Bitertanol, Hexaconazol, Microbutanil, Flusilazole, Etaconazole, Fluotrimazole, Flutriafen, Penconazole, Diniconazole, Cyproconazole, Fenarimol, Triflumizole, Prochloraz, Imazalyl, Pefurazoate, Tridemorph, Fenpropimorph, Triforine, Buthiobate, Pyrifenox, Anilazine, Polyoxins, Metalaxyl, Oxadixyl, Furalaxyl, Isoprothiolane, Probenazole, Pyrrolenitrine, Blastocidin-S, Kasugamycin, Balidamycin, Dihydrostreptomycin sulfate, Benomyl, Carbendazim, Thiophanate methyl, Hymexazol, Basic copper chloride, Basic copper sulfate, Fentin acetate, Triphenyltin hydroxide, Diethofencarb, Metasulfocarb, Quinomethionate, Binapacryl, Lecithin, Sodium hydrogencarbonate, Dithianone, Dinocap, Fenaminosulf, Diclomezine, Guazatine, Dodine, IBP, Edifenphos, Mepanipyrim, Ferimzone, Trichlamide, Metasulfocarb, Fluazinam, Ethoquinolac, Dimetomorph, Pyroquilon, Tecloftalam, Fthalide, Fenazine oxide, Thiabedazole, Tricyclazole, Vinclozolin, Cymoxanil, Cyclobutanil, Guaztine, Propamocarb hydrochloride, Oxolinic acid:
Insecticide/Acaricide
Organophosphorous and Carbamate Insecticides:

Fenthion, Fenitrothion, Diazinon, Chlorpyrifos, ESP, Bamidothion, Fenthoate, Dimethoate, Formothion, Malathon, Trichlorfon, Thiometon, Phosmet, Dichlorvos, Acephate, EPBP, Methyl parathion, Oxydimeton methyl, Ethion, Salithion, Cyanophos, Isoxathione, Pyridafenthion, Phosalone, Methidathion, Sulprofos, Chlorfevinphos, Tetrachlorvinphos, Dimethylvinphos, Propaphos, Isofenphos, Ethyl thiometon, Profenophos, Pyraclofos, Monocrotophos, Azinphos methyl, Aldicarb, Methomyl, Dithiocarb, Carbofuran, Carbosulfan, Benfuracarb, Furathiocarb, Propoxur, BPMC, MTMC, MIPC, carbaryl, Pyrimicarb, Ethiofencarb, Fenoxycarb, cartap, thiocyclam, bensultap, etc.
Pyrethroid insecticides:

Permethrin, Cypermethrin, Deltamethrin, Fenvalerate, Fenpropathrin, Pyrethrin, Allethrin, Tetramethrin, Resmethrin, Dimethrin, Propathrin, Fenothrin, Prothrin, Fluvarinate, Cyfluthrin, Cyhalothrin, Flucythrinate, Ethofenprox, Cycloprothrin, Tralomethrin, Silafluofen, Brofenprox, Acrinathrin, etc.
Benzoyl Urea and other Insecticides:

Diflubenzuron, Chlorfluazuron, Hexaflumuron, Triflumuron, Tetrabenzuron, Fulfenoxuron, Flucycloxuron, Buprofezin, Pyriproxyfen, Methoprene, Benzoepin, Diafenthiuron, Imidacloprid, Fipronyl, Nicotin sulfate, Rotenone, Metaldehyde, Machine oil, Microbial insecticides such as BT and insect-pathogenic viruses, etc.
Nematicides:

Fenamiphos, Fosthiazate, etc.
Acaricides:

Chlorbenzilate, Fenisobromolate, Dicofol, Amitraz, BPPS, Benzomate, Hexythiazox, Fenbutatin oxide, Polynactin, Quinomethionate, CPCBS, Tetradifon, Avermectin, Milbemectin, Clofentezin, Cyhexatin, Pyridaben, Fenproxymate, Tebufenpyrad, Pyrimidifen, Fenothiocarb, Dienochlor, etc.
Plant Growth Regulators:

Gibberellins (e.g., Gibberellin A3, Gibberellin A4, Gibberellin A7), IAA, NAA, etc.

The compound of the present invention can be used to control agricultural pests, sanitary insect pests, stored grain insect pests, cloth insect pests, house insect pests and the like, and have activities of killing adults, nymphs, larvae and eggs. Their representative examples are shown in the following.

Examples of Lepidopterous pest insects include cotton leafworm, cabbage armyworm, black cutworm, common cabbageworm, cabbage looper, diamond-back moth, smaller tea tortrix, tea leaf roller, peach fruit moth, oriental fruit moth, citrus leaf miner, tea leaf roller, apple leaf miner, gypsy moth, tea tussock moth, rice stem borer, grass leaf roller, European corn borer, fall webworm, almond moth, *Heliothis* sp., *Helicoverpa* sp., *Agrotis* sp., casemaking clothes moth, codling moth and cotton bollworm.

Examples of Hemipterous pest insects include green peach aphis, cotton aphid, turnip aphid, grain aphid, bean bug, common green stink bug, arrowhead scale, mulberry mealy scale, greenhouse whitefly, tobacco whitefly, pear psylla, Japanese pear lace bug, brown planthopper, small brown planthopper, white-backed planthopper and green rice leafhopper.

Examples of Coleopterous pest insects include striped flea beetle, cucurbit leaf beetle, Colorado potato beetle, rice water weevil, rice weevil, adzuki bean weevil, Japanese beetle, soybean beetle, *Diabrotica* sp., cigarette beetle, powder post beetle, pine sawyer, white-spotted longicom beetle, *Agriotis* sp., 28-spotted lady beetle, rust-red flour beetle and cotton boll weevil.

Examples of Dipterous pest insects include housefly, *Calliphora lata, Boettcherisca peregrina*, cucurbit fruit fly, citrus fruit fly, seed maggot, rice leaf miner, yellow drosophila, *Stomoxys calcitrans, Culex tritaeniarhynchus, Aedes aegypti* and *Anopheles hyrcanus*.

Examples of Thysanopterous pest insects include *Thrips palmi* and tea thrips.

Examples of Hymenopterous pest insects include *Monomorium pharaonis*, yellow hamet and cabbage sawfly.

Examples of Orhtopterous pest insects include grasshopper, German cockroach, American cockroach and Japanese cockroach.

Examples of Isopterous pest insects include Formosan subterranean termite and *Reticulitermes speratus* Kolbe.

Examples of Aphanipterous pest insects include human flea.

Examples of Anoplurous pest insects include human louse.

Examples of mites include two-spotted spider mite, Kanzawa spider mite, citrus red mite, European red mite, citrus rust mite, apple rust mite, *Tarsonemus* sp., *Brevipalpus* sp., *Eotetranychus* sp., Robin bulb mite, common grain mite, *Desmatophagoides farinae, Boophilus microplus* and *Haemaphysallis bispinosa*.

Examples of plant-parasitic nematodes include southern root-knot nematode, root lesion nematode, soybean cyst nematode, rice white-tip nematode, and pine wood nematode.

Among the pest insects as recited above, Lepidopterous pest insects, Hemipterous pest insects, Coleopterous pest insects, Thysanopterous pest insects, and mites are preferable targets for the compounds of the present invention, and particularly, Lepidopterous and Coleopterous pest insects and mites are the most preferable targets.

In recent times, various pest insects, such as diamondback moths, planthoppers, leafhoppers, aphids, phytophagous mites have developed resistance against organophosphorous insecticides, carbamate insecticides and acaricides. Therefore, the foresaid insecticides and acaricides have lost their efficacy against pest insects and mites that have developed resistance against them. Accordingly, there has been a desire for chemicals that are effective on pest insects and mites of the resistance strains. The compounds of the present invention are chemicals having excellent insecticidal and acaricidal effects on pest insects resistant to organophosphorous pesticides, carbamate insecticides or pyrethroid pesticides and mites resistant to acaricides, as well as those of sensitive strains.

The compounds of the present invention induce very slight phytotoxicity on plants, have low toxicity on fishes and warm-blood animals, and are highly safe.

Further, the compounds of the present invention can be used also as an anti-fouling agent that prevents aqueous adhesive organisms from adhering to structures situated in water such as the bottom of a vessel, fishing nets and the like.

BEST MODES TO IMPLEMENT THE INVENTION

The present invention is further described in detail with reference to the following Examples.

EXAMPLE 1

Preparation of α-(4-tert-butyl-N-methylanilino)-β-hydroxy-(2-trifluoromethylphenyl)acrylonitrile (Compound No. 3—3)

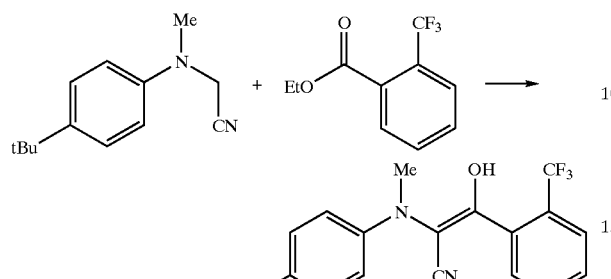

To a suspension of 1.16 g of 2-trifluoromethylbenzoic acid and 1.13 g of potassium hydroxide (oily state) in 30 ml of tetrahydrofuran (THF) was added dropwise 0.85 g of 4-tert-butyl-N-cyanomethyl-N-methylaniline in THF solution under cooling in an ice-bath, and the mixture obtained was stirred for 3 hours at room temperature. To the reacted solution was added saturated aqueous solution of ammonium chloride, and the solution was then extracted with diethyl ether. The organic layer was washed with water and was then evaporated under diminished pressure. The mixture obtained was purified by chromatography on silica-gel column (ethyl acetate/n-hexane=1/4, as an eluent) to give 1.02 g of the title compound. Yield: 65%. Melting point: 170–171° C.

EXAMPLE 2

Preparation of β-(5-chloro-1-methyl-3-trifluoromethylpyrazole-4-yl)-α-(4-chlorophenoxy)-β-hydroxyacrylonitrile (Compound No. 3-8)

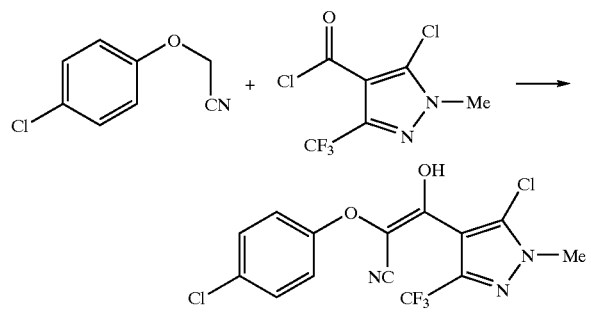

In 4 ml of THF was dissolved 0.4 g of 4-chlorophenoxyacetonitrile. To the solution obtained were added 3 ml of 1.6M n-butyl lithium and 0.59 g of 5-chloro-1-methyl-3-trifluoromethylpyrazole-4-carboxylic chloride, successively, at −78° C. and then left to stand overnight at room temperature. The reaction mixture was poured into ice-water, acidified with conc. hydrochloric acid, and then, extracted with ethyl acetate. The organic layer was evaporated under diminished pressure to give 0.62 g of the title compound. Yield: 69%. Melting point: 126–128° C.

EXAMPLE 3

Preparation of β-(5-chloro-1-methyl-3-trifluoromethylpyrazole-4-yl)-α-(4-chlorophenoxy)-β-pivaloyloxyacrylonitrile (Compound No. 3-9)

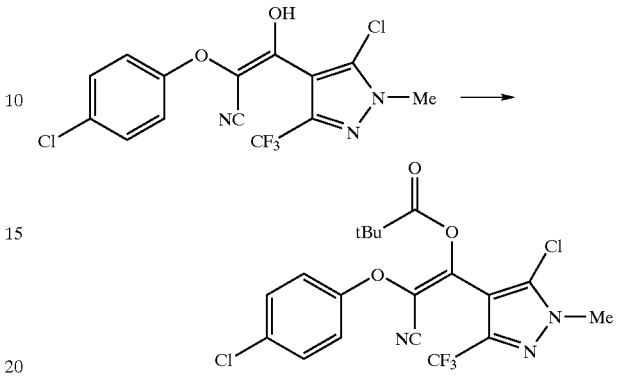

In 5 ml of acetonitrile was dissolved 0.30 g of β-(5-chloro-1-methyl-3-trifluoromethylpyrazole-4-yl)-α-(4-chlorophenoxy)-β-hydroxyacrylonitrile. To the solution obtained were added 0.10 g of triethylamine and 0.12 g of pivaloyl chloride, successively, at 0° C. The mixture obtained was stirred for 5 hours at room temperature. The insoluble material was filtered off, and the filtrate was evaporated under diminished pressure. The mixture obtained was purified by chromatography on silica-gel column (ethyl acetate/n-hexane=3/1, as an eluent) to give 0.28 g of the title compound. Yield: 72%. Refractive index: $n_D^{25.1}$ 1.5058

The compounds prepared in such a way as described above as well as the compounds disclosed in the above Examples were shown in Tables 3 and 4. Similarly, the NMR data of oily substances and others are shown in Table 5.

TABLE 3

| Compound No. | A | R | Xn | Y | Physical Constant (m.p.) |
|---|---|---|---|---|---|
| 3-1 | a1 | H | — | NMe | [102–104] |
| 3-2 | a1 | H | 4-Cl | NMe | [160–162] |
| 3-3 | a1 | H | 4-tBu | NMe | [170–171] |
| 3-4 | a23 | H | — | NMe | [117] |
| 3-5 | a25 | H | — | NMe | [151] |
| 3-6 | a1 | H | 4-Cl | O | NMR |
| 3-7 | a1 | r6 | 4-Cl | O | $n_D^{25.1}$1.5157 |
| 3-8 | a25 | H | 4-Cl | O | [126–128] |
| 3-9 | a25 | r6 | 4-Cl | O | $n_D^{25.1}$1.5058 |
| 3-10 | a1 | H | 4-Cl | S | NMR |
| 3-11 | a1 | r6 | 4-Cl | S | $n_D^{24.5}$1.5333 |
| 3-12 | a25 | H | 4-Cl | S | NMR |
| 3-13 | a25 | r6 | 4-Cl | S | $n_D^{25.1}$1.5369 |
| 3-14 | a25 | H | — | SO$_2$ | [161–163] |
| 3-15 | a25 | r6 | — | SO$_2$ | NMR (b) |
| 3-16 | a25 | H | — | O | NMR |
| 3-17 | a25 | r6 | — | O | $n_D^{25.1}$1.5100 |
| 3-18 | a25 | r6 | — | O | $n_D^{25.2}$1.4980 (c) |
| 3-19 | a25 | H | 2-Cl | O | NMR |
| 3-20 | a25 | r6 | 2-Cl | O | [121–122] |
| 3-21 | a25 | H | 3-Cl | O | NMR |

TABLE 3-continued

| Compound No. | A | R | Xn | Y | Physical Constant (m.p.) |
|---|---|---|---|---|---|
| 3-22 | a25 | r6 | 3-Cl | O | $n_D^{23.9}1.5081$ |
| 3-23 | a25 | r22 | 4-Cl | O | $n_D^{22.9}1.5230$ |
| 3-24 | a25 | r24 | 4-Cl | O | $n_D^{23.0}1.5282$ |
| 3-25 | a25 | H | 2,6-Cl$_2$ | O | NMR |
| 3-26 | a25 | r6 | 2,6-Cl$_2$ | O | $n_D^{22.7}1.5071$ |
| 3-27 | a25 | H | 3,5-Cl$_2$ | O | NMR |
| 3-28 | a25 | r6 | 3,5-Cl$_2$ | O | $n_D^{24.0}1.5151$ |
| 3-29 | a25 | H | 4-F | O | [134–136] |
| 3-30 | a25 | r6 | 4-F | O | $n_D^{23.2}1.4863$ |
| 3-31 | a25 | r22 | 4-F | O | $n_D^{22.7}1.5248$ |
| 3-32 | a25 | H | 3-tBu | O | [228–230] |
| 3-33 | a25 | r6 | 3-tBu | O | $n_D^{22.4}1.4900$ |
| 3-34 | a25 | r22 | 3-tBu | O | $n_D^{22.4}1.5063$ |
| 3-35 | a25 | H | 4-tBu | O | [115–118] |
| 3-36 | a25 | r6 | 4-tBu | O | $n_D^{22.4}1.4946$ |
| 3-37 | a25 | r22 | 4-tBu | O | $n_D^{22.4}1.5250$ |
| 3-38 | a25 | H | 3,5-Me$_2$ | O | [135–136] |
| 3-39 | a25 | r6 | 3,5-Me$_2$ | O | $n_D^{23.3}1.4892$ |
| 3-40 | a25 | H | 4-CF$_3$ | O | [118–119] |
| 3-41 | a25 | r6 | 4-CF$_3$ | O | $n_D^{22.7}1.4719$ |
| 3-42 | a25 | r22 | 4-CF$_3$ | O | $n_D^{23.0}1.5022$ |
| 3-43 | a29 | H | 4-CF$_3$ | O | NMR |
| 3-44 | a29 | r6 | 4-CF$_3$ | O | $n_D^{22.6}1.4902$ |
| 3-44 | a29 | r6 | 4-CF$_3$ | O | $n_D^{22.6}1.4902$ |
| 3-45 | a35 | H | 4-CF$_3$ | O | NMR |
| 3-46 | a35 | r6 | 4-CF$_3$ | O | $n_D^{22.6}1.4890$ |
| 3-47 | a60 | H | 4-CF$_3$ | O | NMR |
| 3-48 | a60 | r6 | 4-CF$_3$ | O | $n_D^{22.6}1.5167$ |
| 3-49 | a25 | r49 | 4-CF$_3$ | O | $n_D^{22.1}1.4808$ |
| 3-50 | a29 | r49 | 4-CF$_3$ | O | $n_D^{22.2}1.5104$ |
| 3-51 | a60 | H | 4-Cl | O | NMR |
| 3-52 | a25 | H | 4-OPh | O | NMR |
| 3-53 | a25 | r6 | 4-OPh | O | $n_D^{23.8}1.5282$ |
| 3-54 | a25 | r6 | 4-OPh | O | $n_D^{23.8}1.5250$ (d) |
| 3-55 | a25 | H | 3-Ph | O | NMR |
| 3-56 | a25 | r6 | 3-Ph | O | $n_D^{22.8}1.5338$ |
| 3-57 | a25 | r6 | 3-Ph | O | $n_D^{22.8}1.5498$ (e) |
| 3-58 | a25 | H | 3-Br | O | NMR |
| 3-59 | a25 | r6 | 3-Br | O | $n_D^{22.8}1.5152$ |
| 3-60 | a25 | H | 3-I | O | NMR |
| 3-61 | a25 | r6 | 3-I | O | $n_D^{24.0}1.4958$ |
| 3-62 | a25 | H | 3-OPh | O | NMR |
| 3-63 | a25 | r6 | 3-OPh | O | $n_D^{24.1}1.5220$ |
| 3-64 | a25 | H | 3-iPr | O | NMR |
| 3-65 | a25 | r6 | 3-iPr | O | $n_D^{23.4}1.5008$ |
| 3-66 | a25 | r6 | 3-iPr | O | $n_D^{23.4}1.4920$ (f) |
| 3-67 | a25 | H | 3-Me | O | NMR |
| 3-68 | a25 | r6 | 3-Me | O | NMR |
| 3-69 | a25 | H | 2,3-Me$_2$ | O | NMR |
| 3-70 | a25 | r6 | 2,3-Me$_2$ | O | $n_D^{24.0}1.4843$ |
| 3-71 | a25 | H | 3-OMe | O | NMR |
| 3-72 | a25 | r6 | 3-OMe | O | $n_D^{23.9}1.4885$ |
| 3-73 | a36 | H | 4-tBu | O | NMR |
| 3-74 | a25 | H | 3,4-Me$_2$ | O | NMR |
| 3-75 | a25 | H | 4-CN | O | NMR |
| 3-76 | a25 | H | 4-CN | O | NMR |

*[ ]: melting point ° C., $n_D$: refractive index
NMR: $^1$H-NMR data are shown on table 5.
(b): mixture of isomers Others are an isomer.
(c): isomer of 3–17
(d): an isomer of 3-52,
(e): an isomer of 3-56,
(f): an isomer of 3-65

TABLE 4

| Compound No. | A | R$_1$ | R$_2$ | Xn | Physical Constant (m.p.) |
|---|---|---|---|---|---|
| 4-1 | a25 | Me | nPr | 4-F | $n_D^{23.9}1.4892$ |
| 4-2 | a25 | Me | tBu | 4-F | $n_D^{23.9}1.4480$ |
| 4-3 | a25 | Me | cPr | 4-F | $n_D^{24.0}1.4958$ |
| 4-4 | a25 | Me | OEt | 4-F | $n_D^{24.0}1.4869$ |
| 4-5 | a25 | Me | nPr | 2-Cl | $n_D^{22.5}1.5130$ |
| 4-6 | a25 | Me | nPr | 2-Cl | $n_D^{22.6}1.5081$ (g) |
| 4-7 | a25 | Me | nPr | 3-Cl | $n_D^{24.0}1.5117$ |
| 4-8 | a25 | Me | nPr | 4-Cl | $n_D^{25.3}1.5042$ |
| 4-9 | a25 | Me | tBu | 4-Cl | $n_D^{25.3}1.4942$ |
| 4-10 | a25 | Me | cPr | 4-Cl | $n_D^{25.4}1.5115$ |
| 4-11 | a25 | Me | OEt | 4-Cl | $n_D^{25.4}1.4994$ |
| 4-12 | a60 | Me | nPr | 4-Cl | $n_D^{23.0}1.5531$ |
| 4-13 | a25 | Me | nPr | 2,6-Cl$_2$ | $n_D^{22.5}1.5152$ |
| 4-14 | a25 | Me | nPr | 3,5-Cl$_2$ | $n_D^{22.3}1.5049$ |
| 4-15 | a25 | Me | nPr | 4-tBu | $n_D^{22.3}1.4817$ |
| 4-16 | a25 | Me | tBu | 4-tBu | $n_D^{22.3}1.4834$ |
| 4-17 | a25 | Me | cPr | 4-tBu | $n_D^{22.3}1.4978$ |
| 4-18 | a25 | Me | OEt | 4-tBu | $n_D^{22.3}1.4875$ |
| 4-19 | a25 | Me | nPr | 3,5-Me$_2$ | $n_D^{23.0}1.5011$ |
| 4-20 | a25 | Me | nPr | — | $n_D^{25.1}1.4988$ |
| 4-21 | a25 | Me | nPr | 4-CF$_3$ | $n_D^{22.3}1.4775$ |
| 4-22 | a60 | Me | nPr | 4-CF$_3$ | $n_D^{25.0}1.5178$ |
| 4-23 | a25 | Me | nPr | 4-OPh | $n_D^{21.7}1.5300$ |
| 4-24 | a25 | Me | nPr | 3-Ph | $n_D^{23.5}1.5411$ |
| 4-25 | a25 | Me | nPr | 3-Ph | $n_D^{23.5}1.5365$ (h) |
| 4-26 | a25 | Me | nPr | 3-Br | $n_D^{22.7}1.5140$ |
| 4-27 | a25 | Me | nPr | 3-I | $n_D^{23.5}1.5030$ |
| 4-28 | a25 | Me | nPr | 3-OPh | $n_D^{23.5}1.5242$ |
| 4-29 | a25 | Me | nPr | 3-iPr | $n_D^{23.2}1.4952$ |
| 4-30 | a25 | Me | nPr | 3-Me | $n_D^{23.6}1.5000$ |
| 4-31 | a25 | Me | nPr | 2,3-Me$_2$ | $n_D^{24.0}1.4773$ |
| 4-32 | a25 | Me | nPr | 3-OMe | $n_D^{23.9}1.4916$ |
| 4-33 | a36 | Me | nPr | 4-tBu | $n_D^{21.0}1.5136$ |
| 4-34 | a36 | Me | tBu | 4-tBu | Viscous oil |
| 4-35 | a36 | Me | cPr | 4-tBu | $n_D^{17.4}1.5329$ |
| 4-36 | a36 | Me | OEt | 4-tBu | $n_D^{20.7}1.5013$ |
| 4-37 | a25 | Me | OEt | 3-tBu | $n_D^{22.4}1.4820$ |
| 4-38 | a36 | Me | nPr | 3-tBu | $n_D^{22.7}1.5177$ |
| 4-39 | a36 | Me | tBu | 3-tBu | $n_D^{22.4}1.4912$ |
| 4-40 | a36 | Me | OEt | 3-tBu | $n_D^{20.0}1.5069$ |
| 4-41 | a25 | Me | nPr | 3,4-Me$_2$ | $n_D^{22.7}1.5049$ |
| 4-42 | a25 | Me | tBu | 3,4-Me$_2$ | $n_D^{22.7}1.5064$ |
| 4-43 | a25 | Me | tBu | 3,4-Me$_2$ | $n_D^{22.7}1.5046$ (i) |
| 4-44 | a25 | Me | nPr | 4-CN | $n_D^{22.7}1.5141$ |

(g): an isomer of 4-5
(h): an isomer of 4-24,
(i): an isomer of 4-42

TABLE 5

NMR data

| Compound No. | $^1$H-NMR (CDCl$_3$) |
|---|---|
| 3-6 | 7.08 (d, 2H), 7.35 (d, 2H), 7.63–7.89 (m, 5H) |
| 3-10 | 7.34 (s, 4H), 7.59–7.85 (m, 5H) |
| 3-12 | 3.98 (s, 3H), 7.28–7.54 (m, 4H) |
| 3-15 | 2.37 and 2.40 (2s, total 3H), 3.96 and 3.99 (2s, total 3H), 7.36–7.89 (m) and 8.06 (d) (total 5H) (a) |
| 3-16 | 3.94 (s, 3H), 6.89–7.28 (m, 5H) |
| 3-19 | 3.98 (s, 3H), 7.12–7.50 (m, 4H) |

TABLE 5-continued

NMR data

| Compound No. | $^1$H-NMR (CDCl$_3$) |
|---|---|
| 3-21 | 3.96 (s, 3H), 6.84–7.18 (m, 4H) |
| 3-25 | 3.95 (s, 3H), 6.82 (t, 2H), 7.26 (d, 1H) |
| 3-27 | 3.91 (s, 3H), 6.74 (s, 2H), 7.00 (s, 1H) |
| 3-43 | 2.38 (s, 3H), 2.48 (s, 3H), 3.82 (s, 3H), 7.09 (d, 2H), 7.61 (d, 2H) |
| 3-45 | 2.22 (s, 3H), 2.25 (s, 3H), 4.11 (s, 3H), 7.14 (d, 2H), 7.67 (d, 2H) |
| 3-47 | 2.74 (s, 3H), 2.79 (s, 3H), 7.17 (d, 2H), 7.68 (d, 2H) |
| 3-51 | 2.74 (s, 3H), 2.79 (s, 3H), 7.03 (d, 2H), 7.43 (d, 2H) |
| 3-52 | 3.98 (s, 3H), 6.98–7.38 (m, 9H) |
| 3-55 | 3.98 (s, 3H), 6.96–7.63 (m, 9H) |
| 3-58 | 3.98 (s, 3H), 6.99–7.42 (m, 4H) |
| 3-60 | 3.98 (s, 3H), 7.06–7.45 (m, 4H) |
| 3-62 | 3.95 (s, 3H), 6.65–7.44 (m, 9H) |
| 3-64 | 1.23 (d, 3H), 2.82–2.98 (m, 1H), 3.95 (s, 3H), 6.75–7.06 (m, 3H), 7.25– |
| 3-67 | 2.35 (s, 3H), 3.95 (s, 3H), 6.80–7.01 (m, 3H), 7.22–7.30 (m, 1H) |
| 3-69 | 2.18 (s, 3H), 2.30 (s, 3H), 3.95 (s, 3H), 6.75–7.15 (m, 3H) |
| 3-71 | 4.75 (s, 3H), 3.95 (s, 3H), 6.52–6.72 (m, 3H), 7.21–7.30 (m, 1H) |
| 3-74 | 1.28 (s, 9H), 2.23 (s, 3H), 3.83 (s, 3H), 7.03 (d, 2H), 7.34 (d. 2H) |
| 3-75 | 2.23 (s, 3H), 2.28 (2, 3H), 3.98 (s, 3H), 6.53–7.15 (m, 3H) |
| 3-76 | 3.99 (s, 3H), 6.90 (d, 2H), 7.20 (d, 2H) |
| 3-77 | 1.11 (s, 9H), 4.00 (s, 3H), 7.20 (d, 2H), 7.72 (d, 2H) |
| 4-34 | 1.11 (s, 9H), 1.32 (s, 9H), 1.48 (d, 3H), 2.28 (s, 3H), 3.94 (s, 3H), 6.01–6.13 (m, 1H) 7.03 (d, 2H), 7.39 (d, 2H) |

(a): data of mixture of isomers

A few examples of compositions of the present invention are described below. Additives and addition ratios are not limited to those in the examples, and can be changed in a wide range. The "parts" used in the formulation examples are parts by weight.

EXAMPLE 4

Wettable Powder

| | |
|---|---|
| A compound of the present invention | 40 parts |
| Diatomaceous earth | 53 parts |
| Higher alcohol sulfate | 4 parts |
| Alkylnaphthalene sulfonate | 3 parts |

The above compounds were mixed uniformly and pulverized finely to give a wettable powder containing 40% of the active ingredient.

EXAMPLE 5

Emulsifiable Concentrate

| | |
|---|---|
| A compound of the present invention | 30 parts |
| Xylene | 33 parts |
| N,N-dimethylformamide | 30 parts |
| Polyoxyethylene alkylallyl ether | 7 parts |

The above compounds were mixed and solved to give an emulsifiable concentrate containing 30% of the active ingredient.

EXAMPLE 6

Dust

| | |
|---|---|
| A compound of the present invention | 10 parts |
| Talc | 89 parts |
| Polyoxyethylene alkylallyl ether | 1 part |

The above compounds were mixed uniformly and pulverized finely to give a dust containing 10% of the active ingredient.

EXAMPLE 7

Granules

| | |
|---|---|
| A compound of the present invention | 5 parts |
| Clay | 73 parts |
| Bentonite | 20 parts |
| Sodium dioctylsulfosuccinate | 1 part |
| Sodium phosphate | 1 part |

The above compounds were sufficiently pulverized and mixed. To the obtained mixture was added water, followed by thorough kneading, granulation and drying to give granules containing 5% of the active ingredient.

EXAMPLE 8

Flowable Concentrate

| | |
|---|---|
| A compound of the present invention | 10 parts |
| Sodium lignin sulfonate | 4 parts |
| Sodium dodecylbenzenesulfonate | 1 part |
| Xanthane gum | 0.2 parts |
| Water | 84.8 parts |

The above compounds were mixed and wet pulverized until the granule size became smaller than 1 μm to give a flowable concentrate containing 10% of the active ingredient.

Availability in Industry

Examples are shown below that formulations containing the compounds of the present invention, which were prepared according to such ways as described above, were applied as an insecticidal/acaricidal agent for controlling pest insects and mites.

TEST EXAMPLE 1

Efficacy on Cotton Aphids

Adult cotton aphids were put onto leaves of cucumbers at the stage of 10 days after germination, planted in a pot with a diameter of c.a. 10 cm. On the following day, all of the adult aphids on the leaves were removed to thereby obtain cucumber leaves infested with the 1st instar nymphs. An emulsifiable concentrate formulation prepared according to the Example 8 was diluted with water so that the concentration of the compound became 125 ppm, followed by spraying thereof over the aphids. Then, the aphids subjected to the spraying were placed in a thermostatic chamber where temperature is maintained at 25° C. and relative humidity was maintained at 65%. Five days later, the aphids were checked to determine their percentage mortality. The test was carried out in duplicate.

As a result of the tests, the compounds listed below revealed 100% percentage mortality.

Note that pyrimicarb provided as a check product has showed a percentage mortality of 9%.

Compound Nos. 3-7, 3-9, 3-17, 3-20, 3-22, 3-23, 3-24, 3-28, 3-30, 3-31, 3-36, 3-41, 3-42, 3-44, 3-46, 3-48, 3-49, 3-56, 3-59, 3-61, 4-5, 4-6, 4-7, 4-8, 4-10, 4-11, 4-14, 4-21, 4-22, 4-24, 4-26

TEST EXAMPLE 2

Effects on Two-Spotted Spider Mite

Fifteen adult females of two-spotted spider mite having acquired resistance to organophosphorous insecticides were put onto the first true leaves of a French bean at the stage of 7–10 days after the germination, planted in a pot with a diameter of c.a. 10 cm. A wettable powder formulation prepared according to the Example 4 was diluted with water so that the concentration of the compound became 125 ppm, followed by spraying thereof over the mites. Then, the mites on the plants were placed in a thermostatic room wherein temperature is maintained at 25° C. and relative humidity is maintained at 65%. Three days later, the mites were checked for their percentage mortality. The test was carried out in duplicate.

As a result of the tests, it was noted that the compounds listed below revealed 100% percentage mortality on the third day after the spraying.

Note that chlordimeform used as a check product has showed a percentage mortality of 13%.

Compound Nos. 3-7, 3-8, 3-9, 3-13, 3-17, 3-18, 3-20, 3-22, 3-23, 3-24, 3-26, 3-28, 3-29, 3-30, 3-31, 3-33, 3-34, 3-36, 3-37, 3-38, 3-39, 3-40, 3-41, 3-42, 3-44, 3-46, 3-48, 3-49, 3-50, 3-54, 3-56, 3-57, 3-59, 3-61, 3-63, 3-65, 3-66, 3-68, 3-70, 3-72, 4-1, 4-2, 4-3, 4-4, 4-5, 4-6, 4-7, 4-8, 4-9, 4-10, 4-11, 4-12, 4-13, 4-14, 4-15, 4-16, 4-17, 4-18, 4-19, 4-20, 4-21, 4-22, 4-23, 4-24, 4-25, 4-26, 4-27, 4-28, 4-29, 4-30, 4-31, 4-32

TEST EXAMPLE 3

Effects on Citrus Red Mite

Eight adult females of susceptible Citrus red mite were inoculated on the surface of Citrus leaf placed in a glass Petridish. A wettable powder formulation prepared according to the Example 4 was diluted with water so that the concentration of the compound became 125 ppm. The solution was sprayed on the mites using a rotary spraying tower up to the fixed volume. Then, the mites on the leaf were placed in the thermostatic room wherein temperature is maintained at 25° C. and relative humidity is maintained at 65%. Three days later, the mites were checked for their percentage mortality. The test was carried out in duplicate. As a result of the tests, it was noted that the compounds listed below revealed 100% percentage mortality on the third day after the spraying.

Note that chlordimeform used as a chek product has showed a percentage mortality of 13%.

Compound Nos.: 3-7, 3-9, 3-13, 3-17, 3-18, 3-20, 3-22, 3-23, 3-24, 3-26, 3-28, 3-29, 3-30, 3-31, 3-33, 3-34, 3-36, 3-37, 3-39, 3-40, 3-41, 3-42, 3-44, 3-46, 3-48, 3-49, 3-50, 3-54, 3-56, 3-57, 3-59, 3-61, 3-63, 3-65, 3-66, 3-68, 3-70, 3-72, 4-1, 4-2, 4-3, 4-4, 4-5, 4-6, 4-7, 4-8, 4-9, 4-10, 4-11, 4-12, 4-13, 4-14, 4-15, 4-16, 4-17, 4-18, 4-19, 4-20, 4-21, 4-22, 4-23, 4-24, 4-25, 4-26, 4-27, 4-28, 4-29, 4-30, 4-31, 4-32

What is claimed is:

1. Compounds represented by Formula (1);

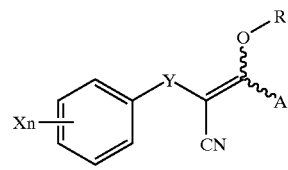

wherein A is phenyl substituted by W or a heterocyclic group substituted by W;

wherein W is nitro, cyano, halogeno, $C_{1-6}$ alkyl, $C_{3-8}$ cycloalkyl, $C_{1-6}$ haloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, $C_{1-6}$ alkylamino, di-$C_{1-6}$ alkylamino, $C_{1-6}$ alkylcarbonyl, $C_{1-6}$ alkcoxycarbonyl, phenyl optionally substituted by $G_1$, or phenoxy optionally substituted by $G_1$;

wherein $G^1$ is nitro, cyano, halogeno, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, $C_{1-6}$ alkylamino, di-$C_{1-6}$ alkylamino, $C_{1-6}$ alkylcarbonyl, or $C_{1-6}$ alkoxycarbonyl;

said heteroyclic group is a 5- or 6-membered heterocyclic group that contains at least one heteroatom selected from a group consisting of oxygen, sulfur and nitrogen;

when either of said phenyl or said heterocyclic group contains 2 or more substituents W, said W may be same or different from each other;

R is hydrogen, $C_{1-6}$ alkyl, $C_{1-6}$ alkoxy $C_{1-6}$ alkyl, $C_{1-6}$ alkylcarbonyloxy $C_{1-6}$ alkyl, $C_{3-6}$ cycloalkylcarbonyloxy $C_{1-6}$ alkyl, $C_{1-6}$ alkoxycarbonyloxy $C_{1-6}$ alkyl, optionally substituted phenylcarbonyloxy $C_{1-6}$ alkyl, $C_{1-6}$ alkylthio $C_{1-6}$ alkyl, $C_{1-6}$ alkylcarbonylthio $C_{1-6}$ alkyl, $C_{3-6}$ cycloalkylcarbonylthio $C_{1-6}$ alkyl, $C_{1-6}$ alkoxycarbonylthio $C_{1-6}$ alkyl, optionally substituted phenylcarbonylthio $C_{1-6}$ alkyl, optionally substituted phenyl $C_{1-6}$ alkyl, a group represented by a formula of $COR_1$, a group represented by a formula of $CSR_1$, or a group represented by a formula of $SO_2R_2$;

wherein $R_1$ is $C_{1-12}$ alkyl, $C_{3-6}$ cycloalkyl, $C_{1-6}$ haloalkyl, $C_{1-6}$ alkoxy, $C_{1-6}$ alkylthio, $C_{1-6}$ alkylamino, di-$C_{1-6}$ alkylamino, optionally substituted phenyl $C_{1-6}$ alkyl, optionally substituted phenyl $C_{1-6}$ alkoxy, or optionally substituted phenyl, and $R_2$ is $C_{1-12}$ alkyl or optionally substituted phenyl;

X is nitro, cyano, halogeno, $C_{1-6}$ alkyl, $C_{2-6}$ alkenyl, $C_{2-6}$ alkynyl, $C_{3-8}$ cycloalkyl, $C_{1-6}$ haloalkyl, $C_{2-6}$ aloalkenyl, $C_{1-6}$ alkoxy, $C_{1-6}$ haloalkoxy, $C_{2-6}$ halkenyloxy, $C_{2-6}$ haloalkenyloxy, $C_{2-6}$ alkynyloxy, $C_{1-6}$ alkylthio, $C_{1-6}$ alkylsulfinyl, $C_{1-6}$ alkylsulfonyl, $C_{1-6}$ alkylamino, di-$C_{1-6}$ alkylamino, tri-$C_{1-6}$ alkylsilyl, $C_{1-6}$ alkoxy $C_{1-6}$ alkyl, $C_{1-6}$ alkylthio $C_{1-6}$ alkyl, $C_{1-6}$ alkylsulfinyl $C_{1-6}$ alkyl, $C_{1-6}$ alkylsulfonyl $C_{1-6}$ alkyl, $C_{1-6}$ alkylcarbonyl, $C_{1-6}$ alkcoxycarbonyl, phenyl $C_{1-6}$ alkyl optionally substituted by $G_2$, phenyl $C_{1-6}$ alkoxy optionally substituted by $G_2$, thienyl optionally substi tuted by $G_3$, pyridyl optionally substituted by $G_2$, pyridyloxy optionally substituted by $G_2$, phenyl optionally substituted by $G_4$, or phenoxy optionally substituted by $G_4$;

wherein $G_2$ is $C_{1-6}$ alkyl, halogeno, $C_{1-6}$ haloalkyl, or $C_{1-6}$ haloalkoxy, $G_3$ is $C_{1-6}$ alkyl or halogeno, and $G_4$ is nitro cyano, halogeno, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, $C_{1-6}$ alkylamino, di-$C_{1-6}$ alkylamino, $C_{1-6}$ alkylcarbonyl or $C_{1-6}$ alkoxycarbonyl;

n is 0, or integer of 1 to 5, with the proviso that when A is substituted phenyl, n is not 0, and when n is 2 or more, the above X may be same or different from each other; and Y is oxygen, sulfur, or nitrogen substituted by either hydrogen or $C_{1-6}$ alkyl, and the salts thereof.

2. An insecticide or acaricide composition characterized by comprising one or ore of compounds represented by Formula (1);

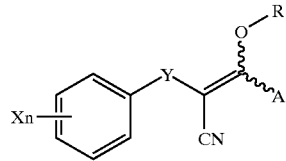

wherein A, R, X, Y and n are as defined in claim 1 and the salts thereof as the active ingredients.

* * * * *